(12) United States Patent
Ohashi et al.

(10) Patent No.: US 8,323,536 B2
(45) Date of Patent: Dec. 4, 2012

(54) NEAR-INFRARED ABSORBING DYE, NEAR-INFRARED ABSORPTIVE FILM-FORMING COMPOSITION, AND NEAR-INFRARED ABSORPTIVE FILM

(75) Inventors: Masaki Ohashi, Joetsu (JP); Takeshi Kinsho, Joetsu (JP); Kazumi Noda, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/108,534

(22) Filed: May 16, 2011

(65) Prior Publication Data

US 2012/0119171 A1 May 17, 2012

(30) Foreign Application Priority Data

Nov. 12, 2010 (JP) ................. 2010-253448

(51) Int. Cl.
*F21V 9/04* (2006.01)
*F21V 9/06* (2006.01)
*G02B 5/22* (2006.01)
*G02B 5/26* (2006.01)
*G03C 1/00* (2006.01)
*G03F 7/00* (2006.01)

(52) U.S. Cl. .......... 252/587; 428/64.8; 430/270.1; 430/281.1; 430/285.1; 430/286.1; 430/944; 548/427; 548/436; 548/455

(58) Field of Classification Search .......... 252/587; 428/64.8; 430/285.1, 270.1, 286.1, 325, 430/313, 323, 30, 327, 395, 494, 944, 281.1; 522/25, 29, 31; 528/402; 544/300, 301; 546/102; 549/511, 13, 428; 548/427, 455, 548/436; 558/418, 419; 560/151, 200; 568/615, 568/620

See application file for complete search history.

(56) References Cited

U.S. PATENT DOCUMENTS

| 4,558,949 | A | 12/1985 | Uehara et al. |
| 4,962,318 | A | 10/1990 | Nishi |
| 5,380,621 | A | 1/1995 | Dichiara et al. |
| 5,412,214 | A | 5/1995 | Suzuki et al. |
| 5,541,235 | A | 7/1996 | Busman et al. |
| 5,632,910 | A | 5/1997 | Nagayama et al. |
| 5,643,700 | A | 7/1997 | Otsuka |
| 5,650,483 | A | 7/1997 | Malik et al. |
| 6,008,350 | A * | 12/1999 | Roschger et al. ............ 544/300 |
| 6,025,117 | A | 2/2000 | Nakano et al. |
| 6,312,867 | B1 | 11/2001 | Kinsho et al. |
| 6,329,125 | B2 | 12/2001 | Takechi et al. |
| 6,475,590 | B1 | 11/2002 | Kitayama et al. |
| 6,503,692 | B2 | 1/2003 | Angelopoulos et al. |
| 7,163,778 | B2 | 1/2007 | Hatakeyama et al. |
| 7,510,820 | B2 | 3/2009 | Hatakeyama et al. |
| 7,531,289 | B2 | 5/2009 | Kinsho et al. |
| 7,771,913 | B2 | 8/2010 | Kaneko et al. |
| 7,868,199 | B2 | 1/2011 | Hasegawa et al. |
| 2007/0238300 | A1 | 10/2007 | Ogihara et al. |
| 2008/0008955 | A1 | 1/2008 | Brodsky et al. |
| 2008/0038662 | A1 | 2/2008 | Hatakeyama et al. |
| 2008/0048155 | A1 * | 2/2008 | Toriniwa et al. ............ 252/587 |
| 2008/0318160 | A1 * | 12/2008 | Ohsawa et al. ............ 430/285.1 |
| 2009/0087799 | A1 | 4/2009 | Tachibana et al. |
| 2009/0136869 | A1 | 5/2009 | Ogihara et al. |
| 2009/0208865 | A1 | 8/2009 | Brunner et al. |
| 2009/0246694 | A1 | 10/2009 | Ohsawa et al. |

FOREIGN PATENT DOCUMENTS

| JP | 58-113706 A | 7/1983 |
| JP | 2-54103 A | 2/1990 |
| JP | 5-291208 A | 11/1993 |
| JP | 6-29186 A | 2/1994 |
| JP | 6-84789 A | 3/1994 |
| JP | 7-146551 A | 6/1995 |
| JP | 7-181688 A | 7/1995 |
| JP | 7-183194 A | 7/1995 |
| JP | 8-253705 A | 10/1996 |
| JP | 9-73173 A | 3/1997 |
| JP | 10-60409 A | 3/1998 |
| JP | 11-23837 A | 1/1999 |
| JP | 11-60735 A | 3/1999 |
| JP | 2000-81511 A | 3/2000 |

(Continued)

OTHER PUBLICATIONS

Narayanan et al., "A New Method for the Synthesis of Heptamethine Cyanine Dyes: Synthesis of New Near-Infrared Fluorescent Labels", Journal of Organic Chemistry, vol. 60, No. 8, 1995, pp. 2391-2395.
Rubingh, R. et al. "Lithographic Performance of a Dual Stage, 0.93NA ArF Step & Scan System", Proc. of SPIE, vol. 5754, p. 681-692.

(Continued)

*Primary Examiner* — Bijan Ahvazi
(74) *Attorney, Agent, or Firm* — Birch, Stewart, Kolasch & Birch, LLP

(57) ABSTRACT

A near-infrared absorbing dye has an anion of formula (1) wherein $A^1$ is H or $CF_3$, $R^0$ is OH or —OC(=O)—R', and R' is a monovalent hydrocarbon group. The dye has excellent solvent solubility as well as good optical properties and heat resistance, offering the advantages of easy coating and effective working during film formation. The dye free of heavy metal in its structure is advantageously used in the process of fabricating semiconductor devices.

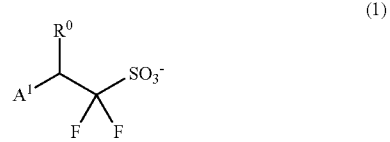

(1)

8 Claims, 20 Drawing Sheets

FOREIGN PATENT DOCUMENTS

| | | |
|---|---|---|
| JP | 2000-336121 A | 12/2000 |
| JP | 2004-310019 A | 11/2004 |
| JP | 2005-15532 A | 1/2005 |
| JP | 2005-520354 A | 7/2005 |
| JP | 2005-250434 A | 9/2005 |
| JP | 2006-152255 A | 6/2006 |
| JP | 2007-145797 A | 6/2007 |
| JP | 2007-171895 A | 7/2007 |
| JP | 2007-204385 A | 8/2007 |
| JP | 2007-297590 A | 11/2007 |
| JP | 2007-302873 A | 11/2007 |
| JP | 2008-65303 A | 3/2008 |
| JP | 2008-83668 A | 4/2008 |
| JP | 2008-88426 A | 4/2008 |
| JP | 2009-98639 A | 5/2009 |
| JP | 2009-126940 A | 6/2009 |
| JP | 2009-258695 A | 11/2009 |
| JP | 2010-253448 A | 11/2010 |
| WO | 2006/006573 A1 | 1/2006 |

* cited by examiner

NEAR-INFRARED ABSORBING DYE, NEAR-INFRARED ABSORPTIVE FILM-FORMING COMPOSITION, AND NEAR-INFRARED ABSORPTIVE FILM

CROSS-REFERENCE TO RELATED APPLICATION

This non-provisional application claims priority under 35 U.S.C. §119(a) on Patent Application No. 2010-253448 filed in Japan on Nov. 12, 2010, the entire contents of which are hereby incorporated by reference.

TECHNICAL FIELD

This invention relates to novel near-infrared absorbing dyes, near-infrared absorptive film-forming compositions comprising the dyes, and near-infrared absorptive films formed from the compositions, which are useful as optical filters or in micropatterning in the process of fabricating semiconductor devices and the like.

BACKGROUND ART

Nowadays near-infrared (NIR) absorbing dyes find use in many applications, typically in electronic materials and the demand for these dyes are increasing. They are useful in many industrial fields. Specifically they cover widely varying applications including filter dyes in optical filters and heat-absorbing filters, additives to image-forming materials using infrared-sensitive coating and solder resists, sensitizers for photo-polymerization and photo-crosslinking reaction, and optical recording materials for optical discs.

While plasma display panels (PDP) are attractive as the large-size flat display, electromagnetic waves and NIR light inevitably generate in principle. The PDPs need means for shutting out interference, for example, electromagnetic wave shields and NIR absorbing filters. These means ameliorate imaging failures and prevent malfunction of remote controllers by infrared interference. JP-A 2000-81511 discloses NIR absorbing dyes which are intended for use in optical filters.

Another example is a CCD camera wherein a NIR absorbing filter is used as an optical filter for shielding off incident NIR light. Then the camera is given a spectral sensitivity approximate to the visible sensitivity. The optical filters to this end often use NIR absorbing dyes such as cyanine dyes, phthalocyanine dyes, and diimonium salts. With respect to the optical filter containing NIR absorbing dye for use in CCD cameras, reference is made to JP-A H11-23837, for example.

Also NIR absorbing dyes are used in invisible printing ink. Printing with ink having no absorption band in the visible light region makes information codes indiscernible by visual observation, thus preventing forgery of confidential documents such as securities and bonds. Reference may be made to JP-A H10-60409.

NIR absorbing dyes are applied to the fabrication of semiconductor devices as well. In the micropatterning step during optical lithography, a photoresist film is exposed to radiation from the projection optical system while optical auto-focusing sensor NIR light is performed so that the wafer surface may be in register with the best image plane of the projection optical system, that is, so as to enhance focus. To increase the accuracy of optical auto-focusing, U.S. Pat. No. 5,643,700 proposes a photoresist film containing a NIR absorbing dye. US 20090208865 discloses a method for introducing a NIR absorbing dye-containing film beneath a photoresist film.

While NIR absorbing dyes are useful in numerous applications as discussed above, one common problem is solubility in organic solvents. While typical NIR absorbing dyes include cyanine dyes, phthalocyanine dyes, metal complexes of nickel or the like, and diimonium salts, they tend to have poor solubility in many organic solvents. Most NIR absorbing dyes are used in organic systems containing base resins and additives as well as the dyes. Reduced solubility of NIR absorbing dyes in organic solvents limits the field of utility thereof. In the IR filter for PDP, for example, a cyanine compound having hexafluoroantimonate as an anion is used which has low solvent solubility despite the advantage of heat resistance. In addition, compounds free of a heavy metal such as antimony are needed in the field of electronic materials where a reduction of metal impurities is desired. WO 2006/006573 describes heavy metal-free dye compounds, which are less soluble in coating solvents such as methyl ethyl ketone. U.S. Pat. No. 5,541,235 describes dyes having a fluorinated alkylsulfonyl anion. However, use of perfluoroalkyl compounds is undesirable because their stability (anti-degradation) assigned to C—F bonds and the biological concentration and accumulation due to hydrophobic and lipophilic properties are of concern. Furthermore, JP-A 2008-88426 describes that solvent solubility is improved using tris(trifluoromethanealkylsulfonyl)methide anion. This anion material is expensive and not regarded commercially viable.

In most cases, it is possible to dissolve NIR absorbing dyes if highly polar solvents such as methanol and dimethyl sulfoxide are used. The use of highly polar solvents, however, may produce undesired side effects such as formation of an uneven film and crystallization as a salt in a dry film. In addition, high-boiling solvents such as dimethyl sulfoxide are difficult to evaporate off during film formation.

Although it is possible to form a film, without a need for organic solvents, by kneading a NIR absorbing dye with a matrix material such as a resin or the like and shaping the mix into a film, this approach is awkward to form a uniform film. On the other hand, if a NIR absorbing dye-containing material dissolves in an organic solvent, it is easy to form a uniform film by standard film-forming techniques such as spin coating. This material may be shelf stored in solution form and easy to handle. For these reasons, NIR absorbing dyes having good solvent solubility offer a great advantage to the film forming process.

CITATION LIST

Patent Document 1: JP-A 2000-81511
Patent Document 2: JP-A H11-23837
Patent Document 3: JP-A H10-60409
Patent Document 4: U.S. Pat. No. 5,643,700 (JP-A H07-146551)
Patent Document 5: US 20090208865
Patent Document 6: US 2008048155 (WO 2006/006573)
Patent Document 7: U.S. Pat. No. 5,541,235 (JP-A H08-253705)
Patent Document 8: JP-A 2008-88426

DISCLOSURE OF INVENTION

An object of the invention is to provide a near-infrared absorbing dye featuring a high solvent solubility and ease of coating. Another object is to provide a near-infrared absorptive film-forming composition comprising the dye and a near-infrared absorptive film formed from the composition.

The inventors have found that a composition comprising a near-infrared absorbing dye of a specific structure has a sufficient solubility in organic solvents and good coating characteristics and is effective to form a film.

In one aspect, the invention provides a near-infrared absorbing dye having an anion of the general formula (1).

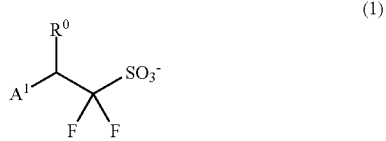
(1)

Herein $A^1$ is hydrogen or trifluoromethyl, $R^0$ is hydroxyl or —OC(=O)—R', and R' is a straight, branched or cyclic $C_1$-$C_{50}$ monovalent hydrocarbon group which may contain a heteroatom.

In a preferred embodiment, the dye is represented by the general formula (2).

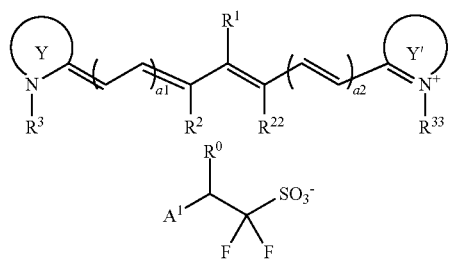
(2)

Herein $R^1$ is hydrogen, halogen, cyano or a straight, branched or cyclic $C_1$-$C_{20}$ monovalent hydrocarbon group which may contain a heteroatom, $R^2$ and $R^{22}$ are each independently hydrogen or a straight or branched $C_1$-$C_{10}$ monovalent hydrocarbon group, $R^2$ and $R^{22}$ may bond together to form a ring with the carbon atoms to which they are attached and the intervening carbon atom, $R^3$ and $R^{33}$ are each independently a straight, branched or cyclic $C_1$-$C_{20}$ monovalent hydrocarbon group which may contain a heteroatom, a1 and a2 are each independently an integer of 0 to 5, $A^1$ and $R^0$ are as defined above, and the partial structures in formula (2):

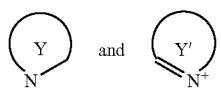

are each independently an aliphatic or aromatic nitrogen-containing heterocyclic compound of 4 to 15 carbon atoms which may contain a heteroatom.

In a more preferred embodiment, the dye is represented by the general formula (3).

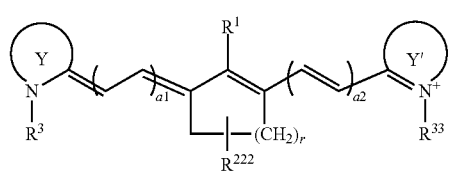
(3)

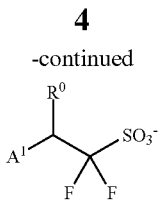

Herein $R^1$, $R^3$, $R^{33}$, a1, a2, $A^1$ and $R^0$ are as defined above, $R^{222}$ is hydrogen or a straight, branched or cyclic $C_1$-$C_5$ monovalent hydrocarbon group, r is 1 or 2, and the partial structures in formula (3):

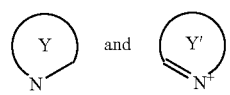

are as defined above.

In a further preferred embodiment, the dye is represented by the general formula (4).

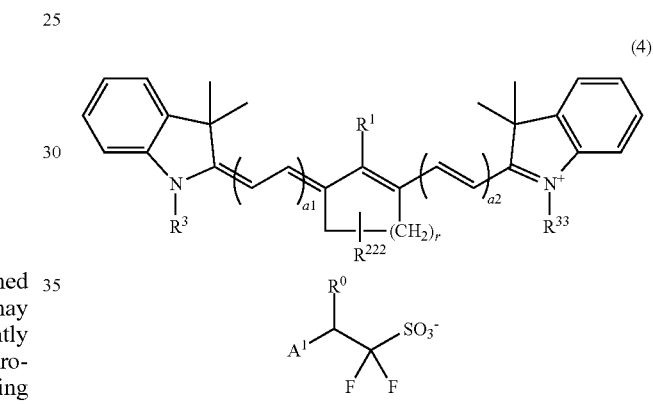
(4)

Herein $R^1$, $R^3$, $R^{33}$, a1, a2, $R^{222}$, r, $A^1$ and $R^0$ are as defined above.

In a further preferred embodiment, the dye is represented by the general formula (5).

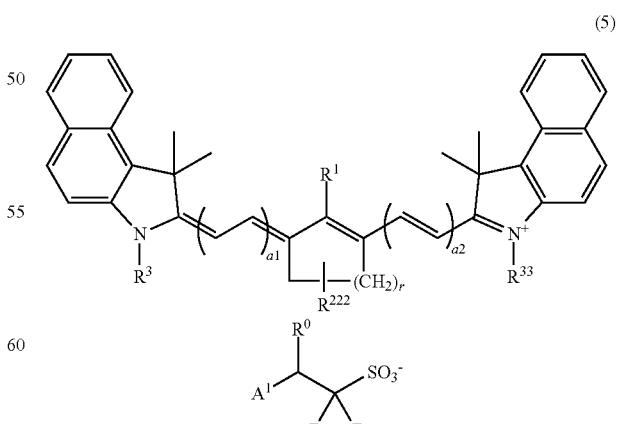
(5)

Herein $R^1$, $R^3$, $R^{33}$, a1, a2, $R^{222}$, r, $A^1$ and $R^0$ are as defined above.

In a further preferred embodiment, the dye is represented by the general formula (6).

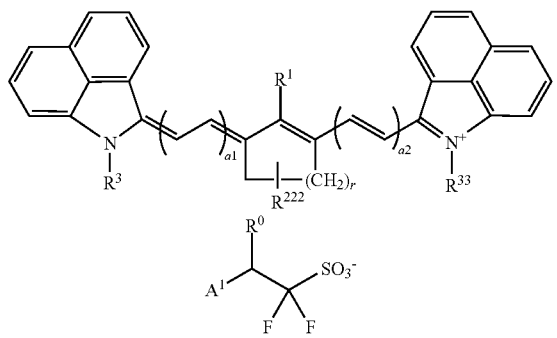
(6)

Herein $R^1$, $R^3$, $R^{33}$, a1, a2, $R^{222}$, r, $A^1$ and $R^0$ are as defined above.

In another aspect, the invention provides a near-infrared absorptive film-forming composition comprising (A) at least one near-infrared absorbing dye as defined above, and (B) at least one solvent. Typically the composition may further comprise at least one polymer and more preferably further comprise at least one component selected from among an acid generator, a crosslinker, and a surfactant.

In a further aspect, the invention provides a near-infrared absorptive film which is formed by coating the composition defined above and evaporating off the solvent.

ADVANTAGEOUS EFFECTS OF INVENTION

The near-infrared absorbing dyes of the invention have excellent solvent solubility as well as good optical properties and heat resistance, offering the advantages of easy coating and effective working to the film forming process. Since the dyes are free of heavy metal in their structure, they are advantageously used in the process of fabricating semiconductor devices and the like.

DESCRIPTION OF EMBODIMENTS

Figure 1:
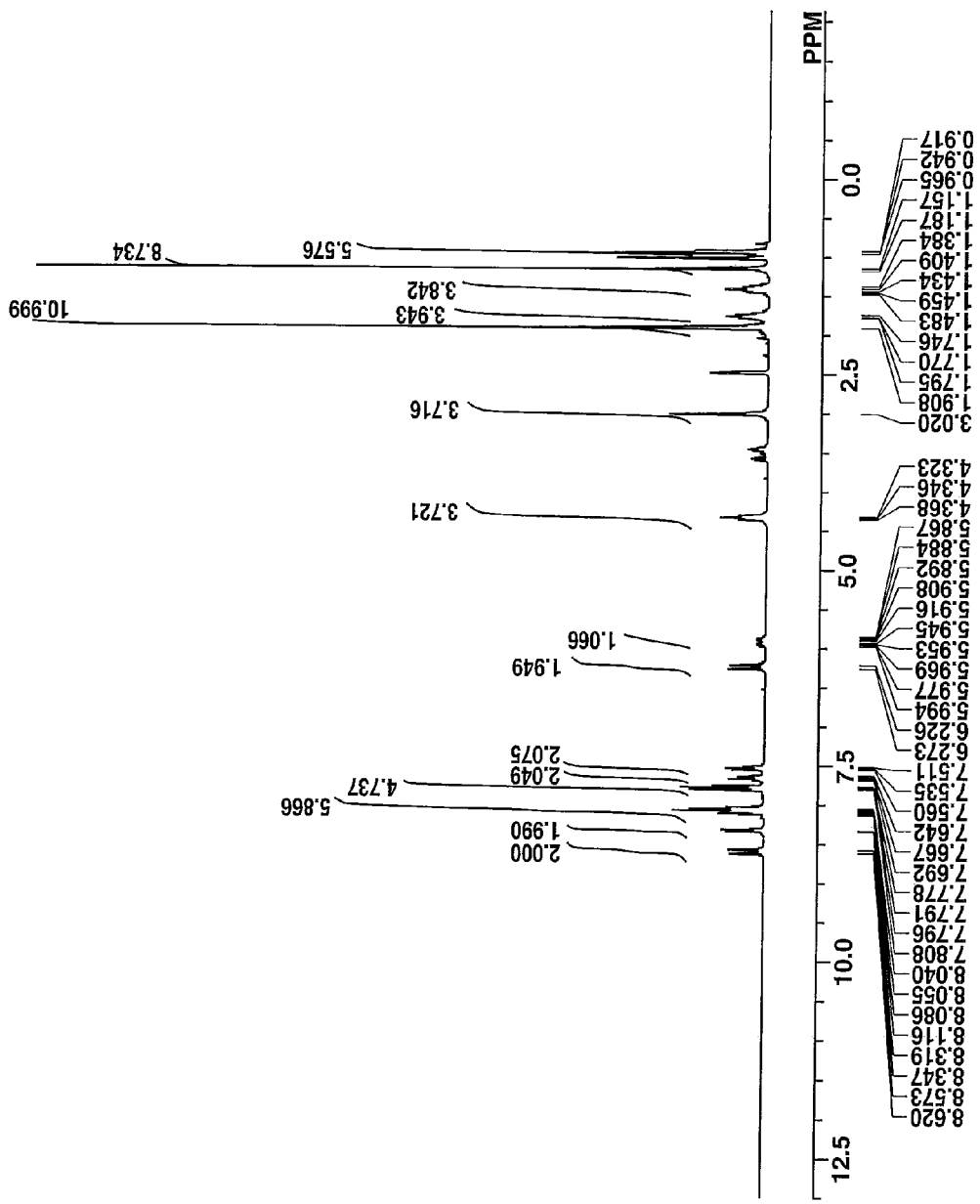
FIGS. 1 and 2 are diagrams of $^1$H-NMR and $^{19}$F-NMR/DMSO-$d_6$ spectra of Dye-A in Synthesis Example 1-1, respectively.

The terms "a" and "an" herein do not denote a limitation of quantity, but rather denote the presence of at least one of the referenced item. As used herein, the notation ($C_n$—$C_m$) means a group containing from n to m carbon atoms per group. As used herein, the term "layer" is used interchangeably with "film" or "coating." Near infrared light is often abbreviated as NIR.

A) NIR Absorbing Dye

The NIR absorbing dye of the invention is characterized by having an anion of the general formula (1).

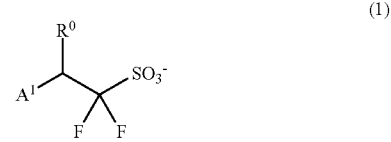
(1)

Herein $A^1$ is hydrogen or trifluoromethyl, $R^0$ is hydroxyl or —OC(=O)—R', and R' is a straight, branched or cyclic $C_1$-$C_{50}$ monovalent hydrocarbon group which may contain a heteroatom.

In formula (1), $R^0$ is a hydroxyl group or —OC(=O)—R' wherein R' is a straight, branched or cyclic $C_1$-$C_{50}$ monovalent hydrocarbon group, such as alkyl, alkenyl, aryl or aralkyl, which may contain a heteroatom. Specifically, suitable alkyl and alkenyl groups include methyl, ethyl, propyl, isopropyl, n-butyl, sec-butyl, tert-butyl, n-pentyl, n-hexyl, n-heptyl, n-octyl, n-decyl, n-dodecyl, cyclopropyl, cyclopentyl, cyclohexyl, cycloheptyl, cyclopropylmethyl, 4-methylcyclohexyl, cyclohexylmethyl, bicyclo[2.2.1]hepten-2-yl, 1-adamantyl, 2-adamantyl, steroid structure-bearing groups, isopropenyl, and vinyl. Suitable aryl groups include phenyl, 4-methoxyphenyl, 4-tert-butylphenyl, 4-biphenyl, 1-naphthyl, 2-naphthyl, 10-anthranyl, 2-furanyl, thienyl, 4-hydroxyphenyl, 3-methoxyphenyl, 2-methoxyphenyl, 4-ethoxyphenyl, 4-tert-butoxyphenyl, 3-tert-butoxyphenyl, 2-methylphenyl, 3-methylphenyl, 4-methylphenyl, 4-ethylphenyl, 4-n-butylphenyl, 2,4-dimethylphenyl, 4-vinylphenyl, methylnaphthyl, ethylnaphthyl, methoxynaphthyl, ethoxynaphthyl, dimethylnaphthyl, diethylnaphthyl, dimethoxynaphthyl, and diethoxynaphthyl. Suitable aralkyl groups include benzyl, 1-phenylethyl, and 2-phenylethyl.

One of the features of the NIR absorbing dye is that the structure of the anion may be readily tailored by a choice of $R^0$ in formula (1) from a wide variety of substituent groups. For example, when a linear or branched alkyl is incorporated into $R^0$, the dye compound is further improved in solvent solubility as required upon film formation. When a cyclic substituent group is incorporated into $R^0$ to provide a robust structure, the dye compound is improved in crystallinity while maintaining solvent solubility. When an aromatic substituent group is incorporated into $R^0$, the dye compound makes it possible to adjust the n and k values of a NIR absorptive film, so that the film may serve as an antireflective coating best suited for lithography. When a NIR absorptive composition contains a dye wherein $R^0$ is hydroxyl and a crosslinker, the composition is effectively curable during the film formation step, forming a NIR absorptive film.

Of the anion structures illustrated above, those anion structures wherein $R^0$ is hydroxyl or —OC(═O)—R' wherein R' is n-butyl, t-butyl, cyclohexyl, phenyl or adamantyl are more preferred for ease and cost of preparation.

Examples of the anion structure of the NIR absorbing dye according to the invention are given below, but not limited thereto.

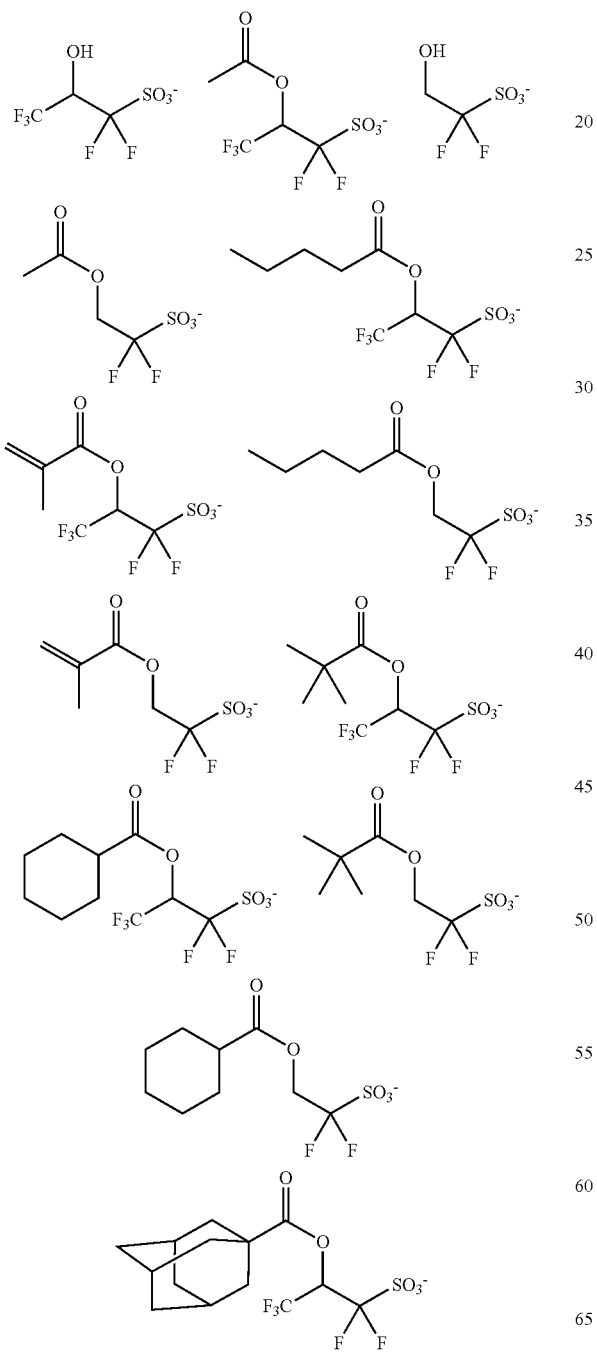
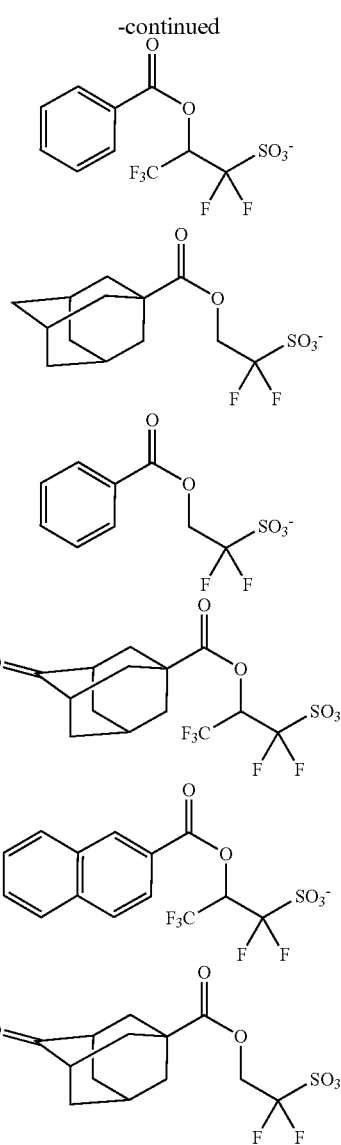

The preferred NIR absorbing dye has a structure of the general formula (2).

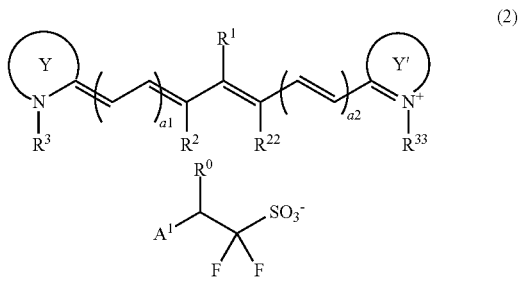

Herein $R^1$ is hydrogen, halogen, cyano or a straight, branched or cyclic $C_1$-$C_{20}$ monovalent hydrocarbon group which may contain a heteroatom. $R^2$ and $R^{22}$ are each independently hydrogen or a straight or branched $C_1$-$C_{10}$ monovalent hydrocarbon group, $R^2$ and $R^{22}$ may bond together to form a ring with the carbon atoms to which they are attached and the intervening carbon atom. $R^3$ and $R^{33}$ are each independently a straight, branched or cyclic $C_1$-$C_{20}$ monovalent hydrocarbon group which may contain a heteroatom. The subscripts a1 and a2 are each independently an integer of 0 to 5. $A^1$ and $R^0$ are as defined above. The partial structures in formula (2):

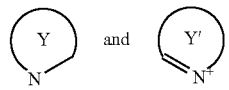

are each independently an aliphatic or aromatic nitrogen-containing heterocyclic compound of 4 to 15 carbon atoms which may contain a heteroatom.

In formula (2), $R^1$ is hydrogen, halogen, a cyano group, or a straight, branched or cyclic $C_1$-$C_{20}$ monovalent hydrocarbon group which may contain a heteroatom. Specifically, $R^1$ is hydrogen, halogen or cyano while other suitable examples are shown below. Suitable straight or branched alkyl groups include methyl, ethyl, propyl, isopropyl, n-butyl, sec-butyl, tert-butyl, pentyl, isopentyl, neopentyl, tert-pentyl, 1-methylpentyl, 2-methylpentyl, hexyl, isohexyl, 5-methylhexyl, heptyl, octyl, nonyl, decyl and dodecyl. Suitable alicyclic hydrocarbon groups include cyclopentyl, cyclohexyl, cycloheptyl, cyclopropylmethyl, 4-methylcyclohexyl, cyclohexylmethyl, norbornyl, and adamantyl. Suitable aromatic hydrocarbon groups include phenyl, o-tolyl, m-tolyl, p-tolyl, xylyl, mesityl, o-cumenyl, m-cumenyl, p-cumenyl, biphenylyl, naphthyl, and anthryl. Suitable alkenyl groups include vinyl, allyl, 1-propenyl, 2-propenyl, isopropenyl, butenyl, hexenyl, and cyclohexenyl. Suitable heteroatom-containing hydrocarbon groups include alkoxy groups such as methoxy, ethoxy, propoxy, and butoxy, aryloxy groups such as phenoxy, and the foregoing hydrocarbon groups having such an alkoxy or aryloxy group substituted thereon, the foregoing hydrocarbon groups having a carbonyl group substituted thereon, the foregoing hydrocarbon groups having a hydroxyl group substituted thereon, acetyl, benzoyl or phenyloxycarbonyl or the foregoing hydrocarbon groups having such an ester bond-containing substituent group, the foregoing hydrocarbon groups having a carboxyl group substituted thereon, the foregoing hydrocarbon groups having sulfonic acid substituted thereon, the foregoing hydrocarbon groups having fluorine, chlorine, bromine or iodine substituted thereon, phenylsulfonyl or the foregoing hydrocarbon groups having phenylsulfonyl substituted thereon, alkylamino and arylamino groups such as dimethylamino, diethylamino, and diphenylamino and the foregoing hydrocarbon groups having such an amino group substituted thereon, thioalkoxy and thioaryloxy groups such as thiomethoxy, thioethoxy, and thiophenoxy, the foregoing hydrocarbon groups having such a thioalkoxy or thioaryloxy group substituted thereon, and hydrocarbon groups comprising a combination of two or more substituent groups selected from among the foregoing.

$R^2$ and $R^{22}$ are each independently hydrogen or a straight or branched $C_1$-$C_{10}$ monovalent hydrocarbon group, and $R^2$ and $R^{22}$ may bond together to form a ring, specifically a non-aromatic ring, with the carbon atoms to which they are attached and the intervening carbon atom. Examples of $R^2$ and $R^{22}$ include hydrogen, methyl, ethyl, propyl, isopropyl, n-butyl, sec-butyl, tert-butyl, pentyl, isopentyl, neopentyl, tert-pentyl, 1-methylpentyl, 2-methylpentyl, and hexyl. When $R^2$ and $R^{22}$ bond together to form a ring, a 5- or 6-membered ring is preferred. In the ring structure thus formed, some hydrogen may be substituted by a straight or branched monovalent hydrocarbon group.

$R^3$ and $R^{33}$ are each independently a straight, branched or cyclic $C_1$-$C_{20}$ monovalent hydrocarbon group which may contain a heteroatom. Exemplary groups are shown below. Suitable straight or branched alkyl groups include methyl, ethyl, propyl, isopropyl, n-butyl, sec-butyl, tert-butyl, pentyl, isopentyl, neopentyl, tert-pentyl, 1-methylpentyl, 2-methylpentyl, hexyl, isohexyl, 5-methylhexyl, heptyl, octyl, nonyl, decyl and dodecyl. Suitable alicyclic hydrocarbon groups include cyclopentyl, cyclohexyl, cycloheptyl, cyclopropylmethyl, 4-methylcyclohexyl, cyclohexylmethyl, norbornyl, and adamantyl. Suitable aromatic hydrocarbon groups include phenyl, o-tolyl, m-tolyl, p-tolyl, xylyl, mesityl, o-cumenyl, m-cumenyl, p-cumenyl, biphenylyl, naphthyl, and anthryl. Suitable alkenyl groups include vinyl, allyl, 1-propenyl, 2-propenyl, isopropenyl, butenyl, hexenyl, and cyclohexenyl. Suitable heteroatom-containing hydrocarbon groups include the foregoing hydrocarbon groups having an alkoxy or aryloxy group (e.g., methoxy, ethoxy, propoxy, butoxy or phenoxy) substituted thereon, the foregoing hydrocarbon groups having a carbonyl group substituted thereon, the foregoing hydrocarbon groups having a hydroxyl group substituted thereon, the foregoing hydrocarbon groups having an ester bond-containing substituent group (e.g., acetyl, benzoyl or phenyloxycarbonyl), the foregoing hydrocarbon groups having a carboxyl group substituted thereon, the foregoing hydrocarbon groups having sulfonic acid substituted thereon, the foregoing hydrocarbon groups having fluorine, chlorine, bromine or iodine substituted thereon, the foregoing hydrocarbon groups having an alkylamino or arylamino group (e.g., dimethylamino, diethylamino or diphenylamino) substituted thereon, the foregoing hydrocarbon groups having a thioalkoxy or thioaryloxy group (e.g., thiomethoxy, thioethoxy or thiophenoxy) substituted thereon, and hydrocarbon groups comprising a combination of two or more substituent groups selected from among the foregoing.

The subscripts a1 and a2 are each independently an integer of 0 to 5. As these subscripts vary, i.e., the length of conjugated system varies, the NIR absorbing dye changes its absorption wavelength. From the standpoints of the wavelength suited for the intended application and the availability of starting reactants, a1 and a2 are preferably 0 to 2, more preferably 1 or 2.

The partial structure in formula (2):

is an aliphatic or aromatic nitrogen-containing heterocyclic compound of 4 to 15 carbon atoms which may contain a heteroatom. An exemplary partial structure is one of partial structures of the general formulae (7) to (11).

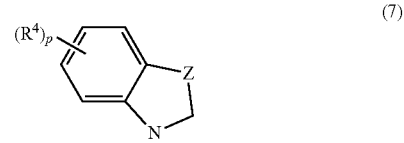

(7)

-continued

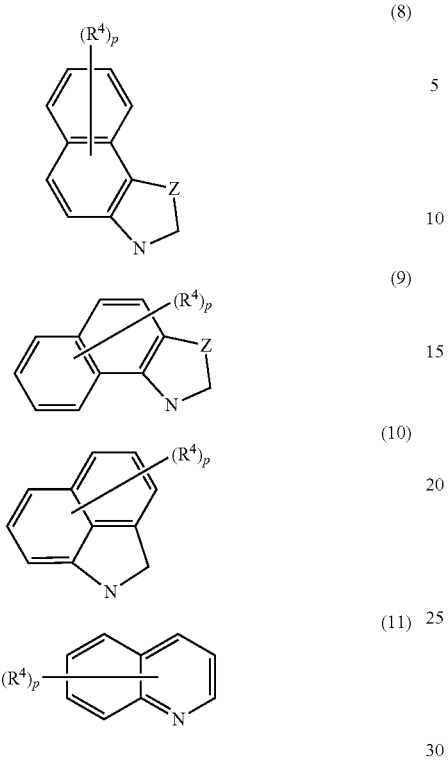

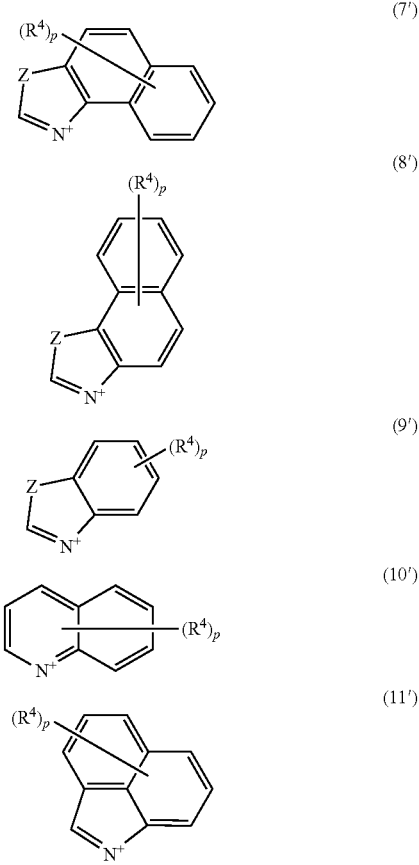

Herein R⁴, p and Z are as defined above.
The more preferred NIR absorbing dye has a structure of the general formula (3).

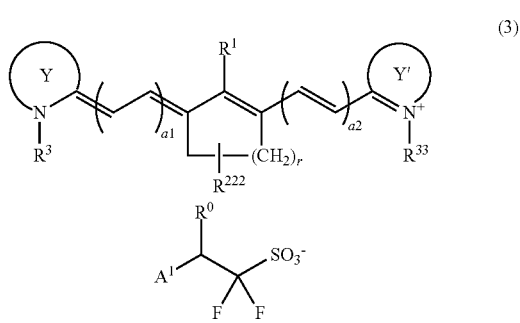

Herein R⁴ is halogen, an alkoxy group of 1 to 10 carbon atoms, preferably 1 to 6 carbon atoms, a nitro group, or a monovalent hydrocarbon group of 1 to 10 carbon atoms, preferably 1 to 6 carbon atoms; p is an integer of 0 to 4; Z is an oxygen atom, sulfur atom or —C($R^z$)$_2$—, and $R^z$ is hydrogen or a monovalent hydrocarbon group of 1 to 10 carbon atoms, preferably 1 to 6 carbon atoms.

Examples of R⁴ include fluorine, chlorine, bromine, iodine, methoxy, ethoxy, n-butoxy, t-butoxy, and nitro, while suitable monovalent hydrocarbon groups of 1 to 10 carbon atoms include methyl, ethyl, propyl, isopropyl, n-butyl, sec-butyl, tert-butyl, pentyl, isopentyl, neopentyl, tert-pentyl, 1-methylpentyl, 2-methylpentyl, hexyl, cyclopentyl, and cyclohexyl.

The subscript p is an integer of 0 to 4. For the availability of starting reactants, p is preferably 0 to 2, more preferably 0 or 1.

Examples of $R^z$ include hydrogen, methyl, ethyl, propyl, isopropyl, n-butyl, sec-butyl, tert-butyl, pentyl, isopentyl, neopentyl, tert-pentyl, 1-methylpentyl, 2-methylpentyl, hexyl, cyclopentyl, and cyclohexyl, with hydrogen or methyl being preferred.

The partial structure in formula (2):

is an aliphatic or aromatic nitrogen-containing heterocyclic compound of 4 to 15 carbon atoms which may contain a heteroatom. An exemplary partial structure is one of partial structures of the general formulae (7') to (11').

Herein $R^1$, $R^3$, $R^{33}$, a1, a2, $A^1$, and $R^0$ are as defined above, $R^{222}$ is hydrogen or a straight, branched or cyclic $C_1$-$C_5$ monovalent hydrocarbon group, r is 1 or 2, and the partial structures in formula (3):

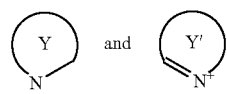

are as defined above.

In formula (3), $R^{222}$ is hydrogen or a straight, branched or cyclic $C_1$-$C_5$ monovalent hydrocarbon group, typically alkyl.

Suitable monovalent hydrocarbon groups include methyl, ethyl, n-propyl, 2-propyl, n-butyl, isobutyl, t-butyl, n-pentyl, t-amyl, and cyclopentyl. Inter alia, hydrogen, methyl and ethyl are preferred.

The even more preferred NIR absorbing dyes have structures of the general formulae (4) to (6).

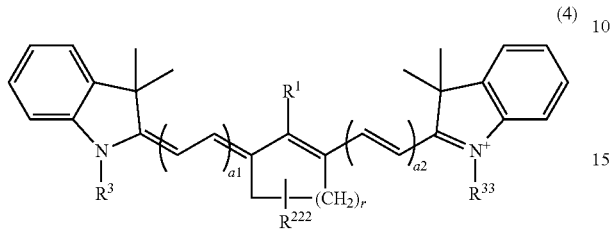
(4)

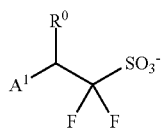

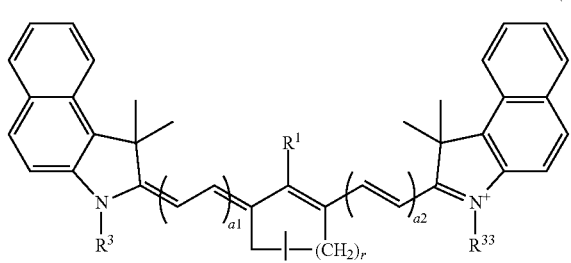
(5)

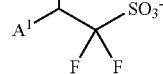

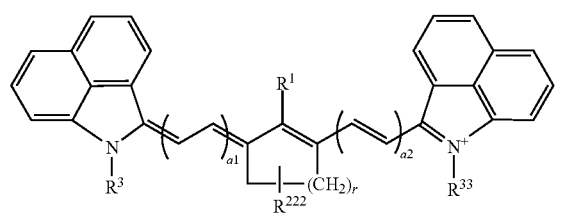
(6)

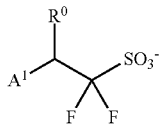

Herein $R^1$, $R^3$, $R^{33}$, a1, a2, $R^{222}$, r, $A^1$, and $R^0$ are as defined above.

The NIR absorbing dyes of formulae (4) to (6) are most preferred because they are fully resistant to heat and light and have an absorption band suitable in the intended applications such as optical filters and semiconductor device fabrication.

Exemplary structures of the cation of the NIR absorbing dye are shown below, but not limited thereto.

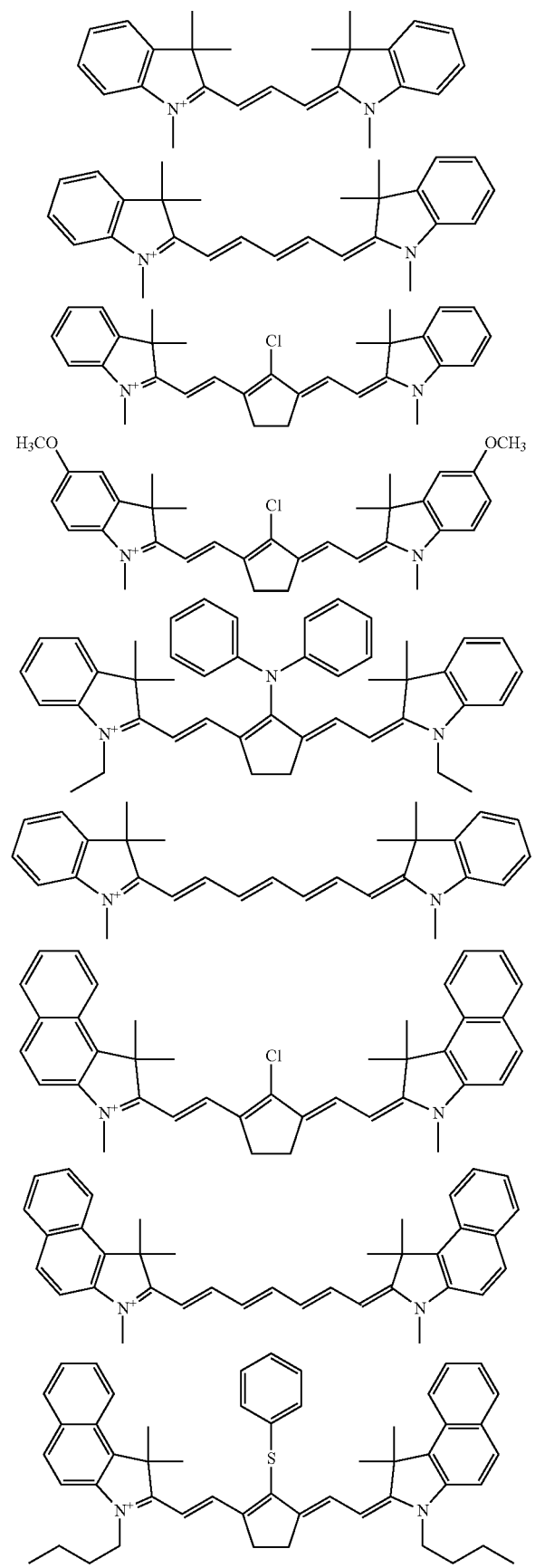

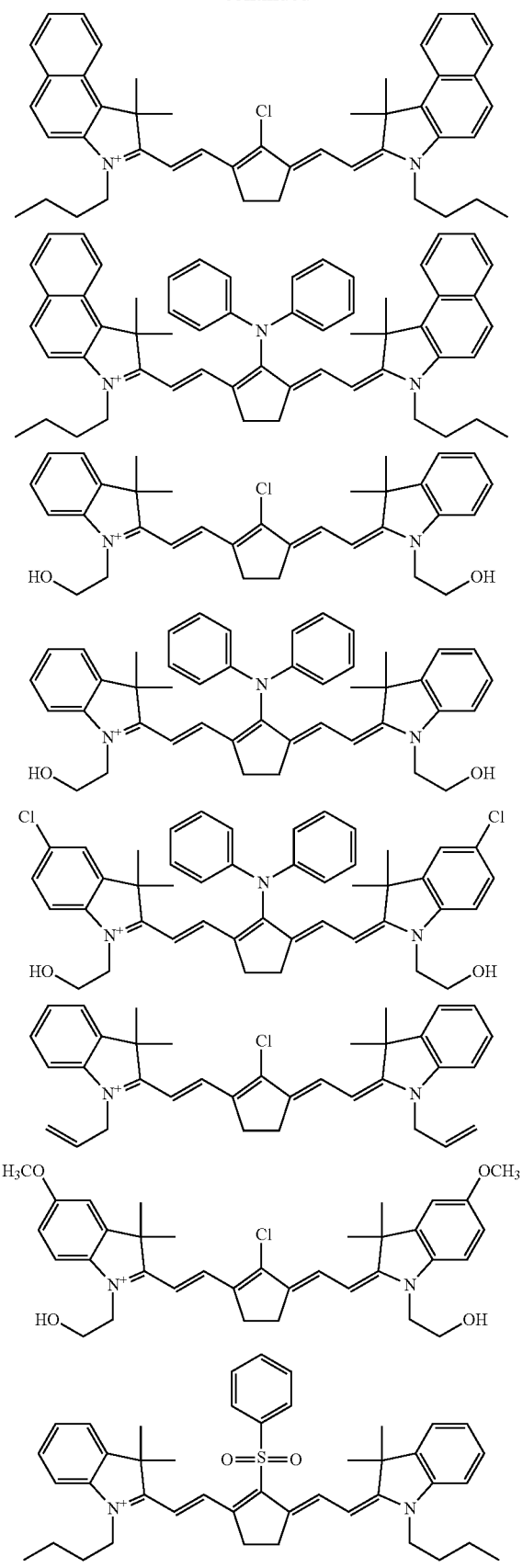
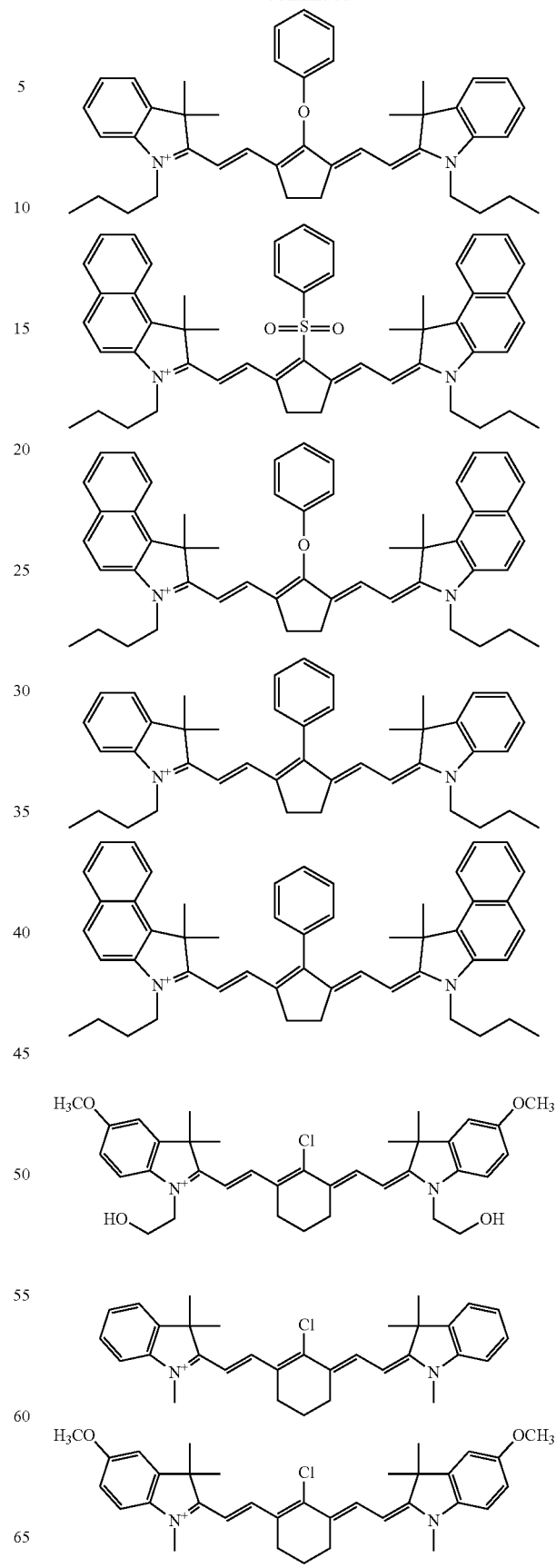

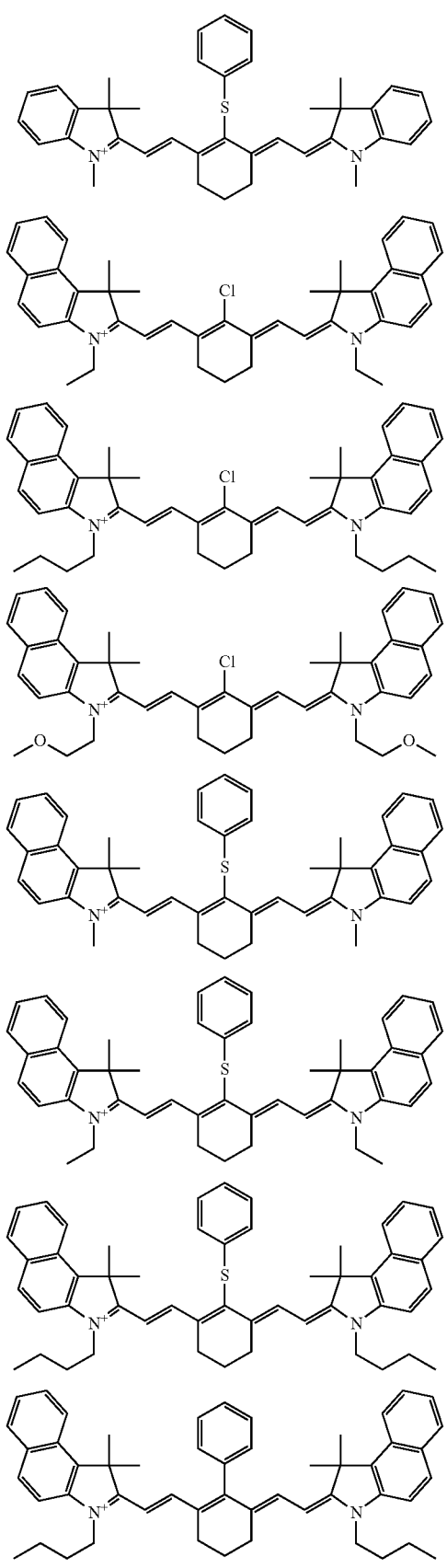
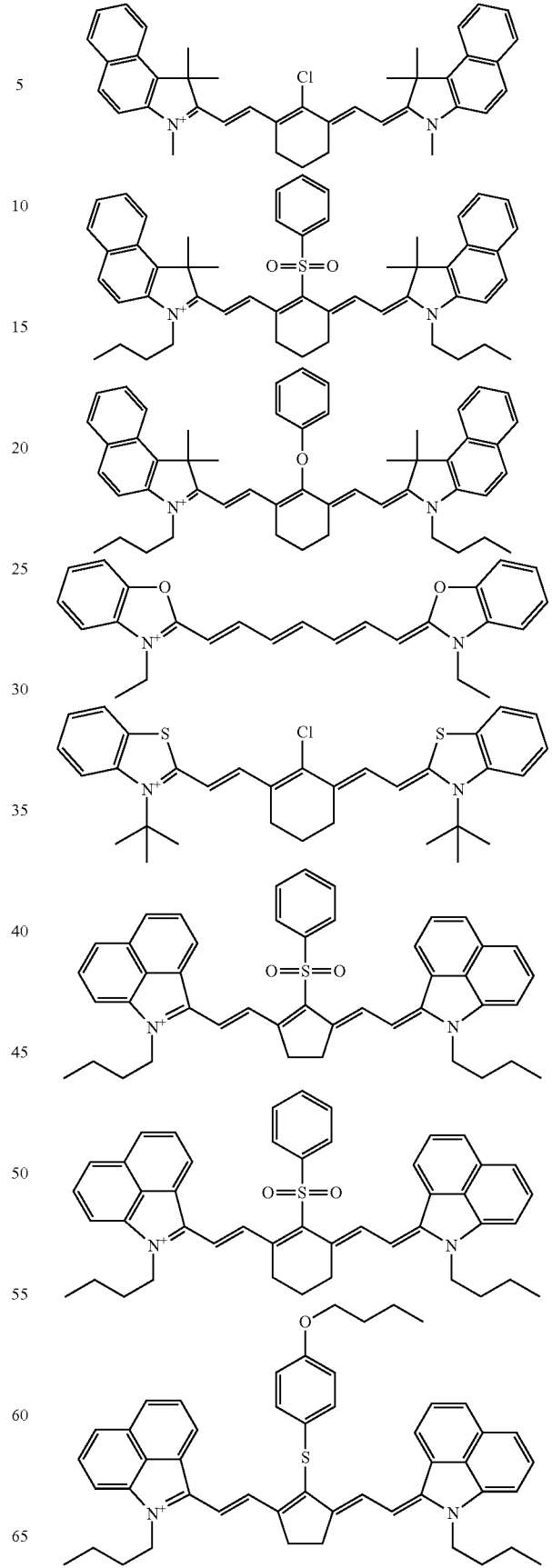

-continued
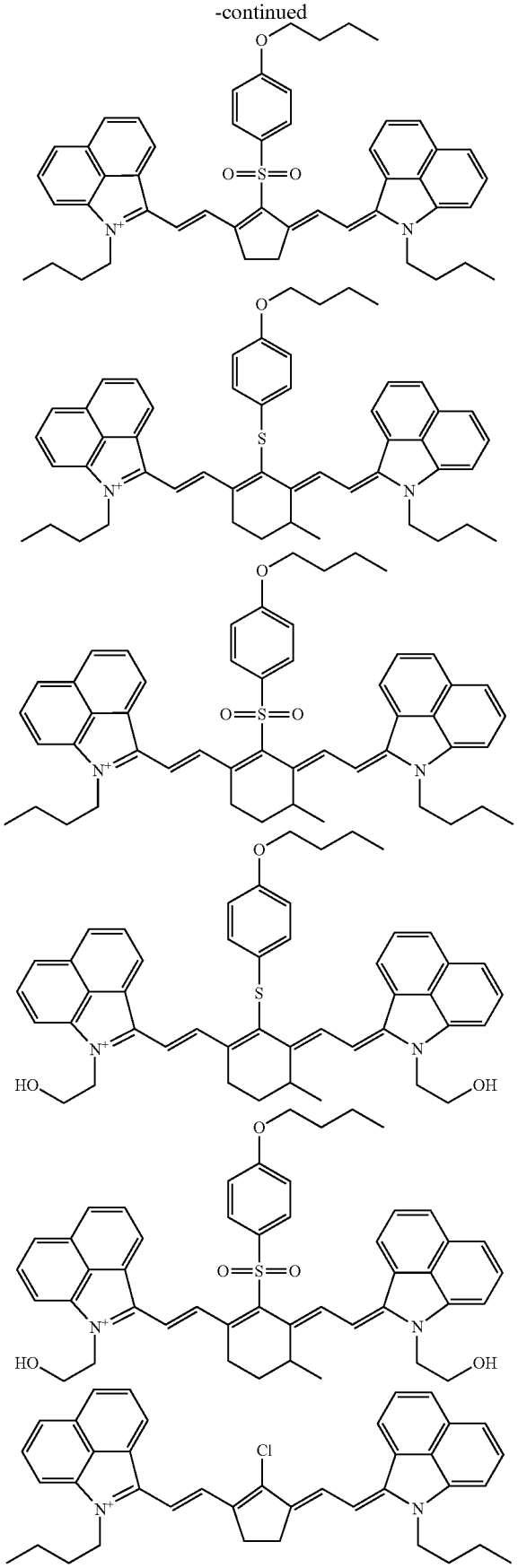
-continued
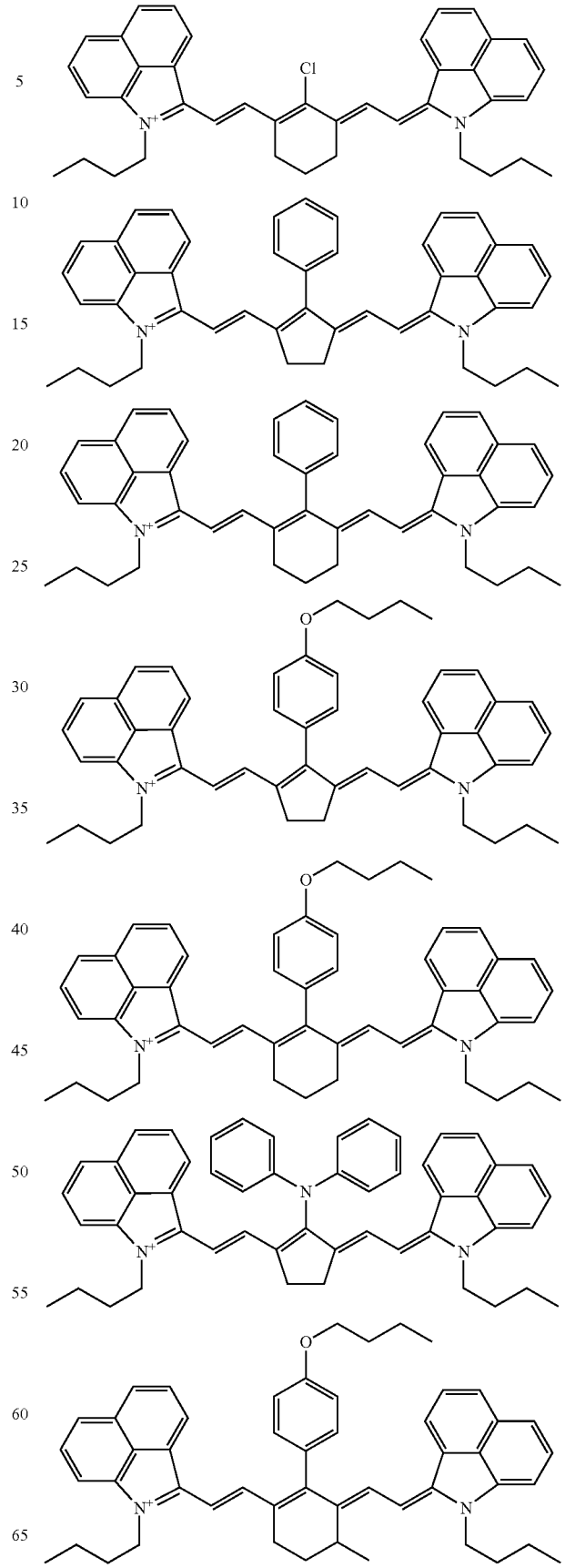

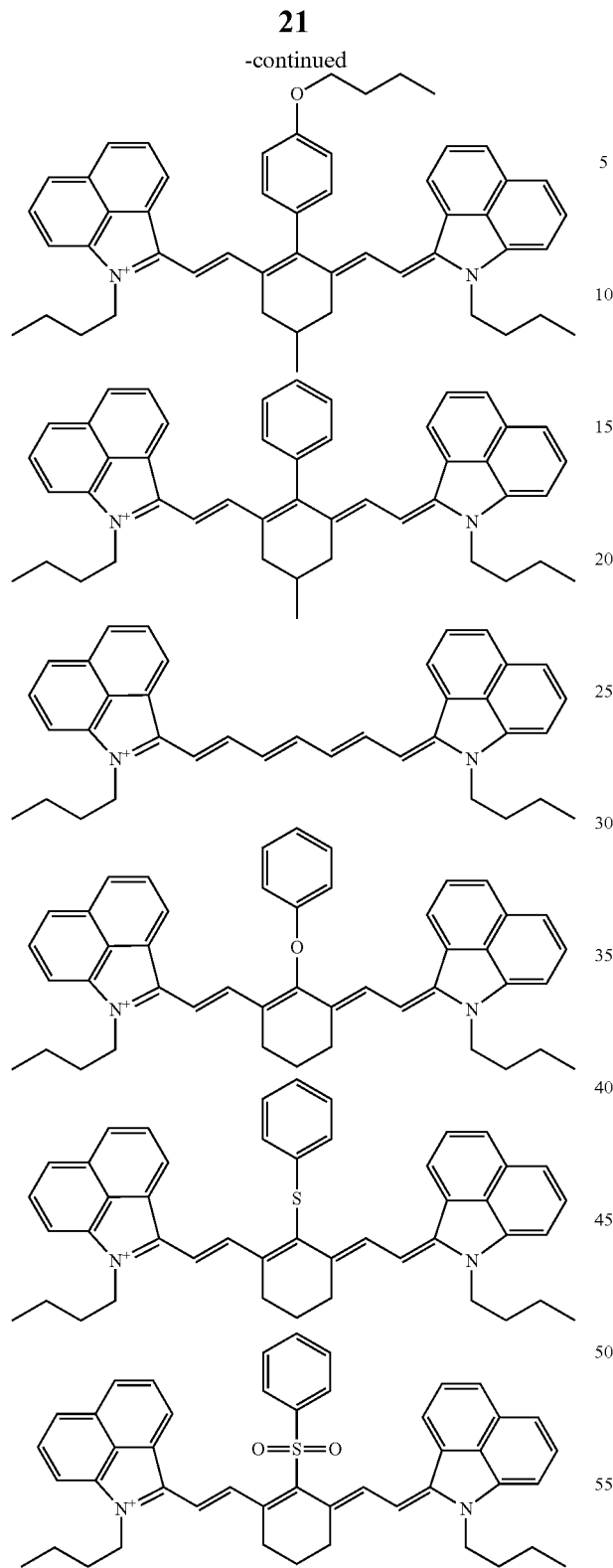

Combinations of the above-illustrated cations with the above-illustrated anions are especially preferred as the NIR absorbing dye of the invention.

Now the synthesis of NIR absorbing dyes of the invention is described. For example, the NIR absorbing dyes may be synthesized according to the following process of Schemes 1 and 2 although the synthesis of NIR absorbing dyes is not limited thereto.

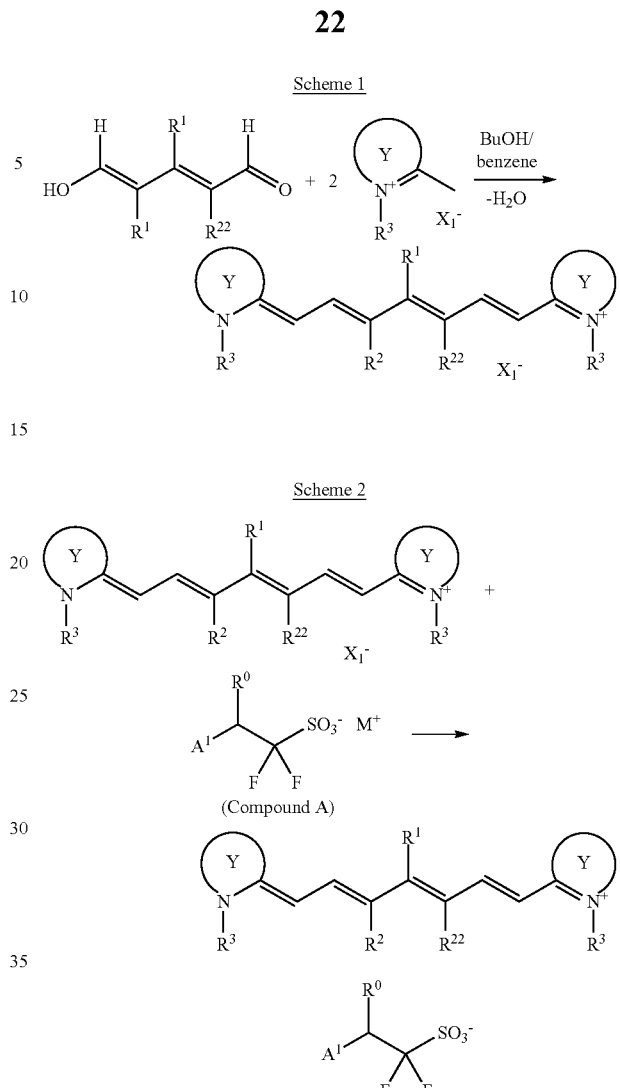

Herein $R^1$, $R^2$, $R^{22}$, $R^3$, $A^1$, and $R^0$ are as defined above, $X_1^-$ is an inorganic or organic anion, $M^+$ is a cation, and the partial structures:

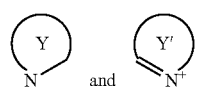

are as defined above.

The first step according to Scheme 1 is one exemplary step of synthesizing a cation or NIR absorbing dye precursor. Reference may be made to Journal of Organic Chemistry, 60, 2391 (1995). With respect to $R^1$, a commercially available reactant may be used, or when $R^1$ is a halogen atom such as chlorine, it may be converted into another substituent group following the Scheme 1 step, by utilizing any organic chemistry procedures such as nucleophilic displacement reaction or coupling reaction.

Exemplary anions represented by $X_1^-$ include halide ions such as chloride, bromide and iodide ions, conjugate bases of sulfonic acid such as mesylate and tosylate, and conjugate bases of mineral acids such as $BF_4^-$, $PF_6^-$, $ClO_4^-$, $NO_3^-$ and $SbF_6^-$.

The NIR absorbing dye precursor may be prepared according to Scheme 1 or commercially available from chemical suppliers.

Next the NIR absorbing dye precursor is reacted with Compound A according to Scheme 2 whereby it is converted through anion exchange into a NIR absorbing dye having an anion structure according to the invention. On ion exchange reaction, it is preferred for effective synthesis that $M^+$ be a lithium, sodium, potassium, or ammonium ion. With respect to ion exchange reaction, reference may be made to JP-A 2007-145797, for example. With respect to the synthesis of Compound A, reference may be made to JP-A 2007-145797 and JP-A 2009-258695, for example. For example, Compound A wherein $A^1$ is trifluoromethyl may be synthesized by a convenient organic chemistry procedure using a relatively inexpensive reactant like 1,1,1,3,3,3-hexafluoroisopropanol, and then the overall process becomes commercially acceptable.

Another embodiment of the invention is a NIR absorptive film-forming composition comprising a NIR absorbing dye of the structure defined herein. The composition may comprise two or more NIR absorbing dyes of the structure defined herein and optionally one or more other NIR absorbing dyes.

The other NIR absorbing dye other than the structure defined herein may be any dye which absorbs radiation in a wavelength range of 500 to 1,200 nm. Suitable other NIR absorbing dyes include those of the general formulae (12) to (14), but are not limited thereto.

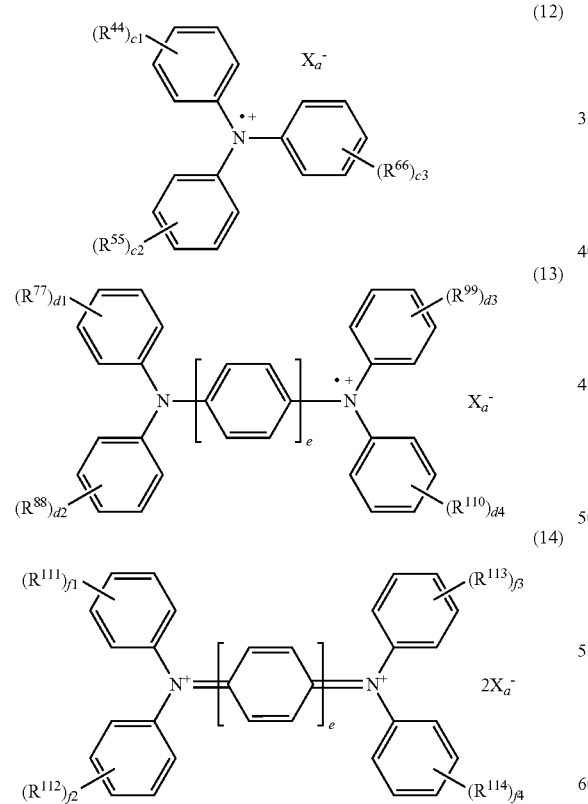

In formulae (12) to (14), $X_a^-$ is an anion. Exemplary anions include halide ions such as chloride, bromide, and iodide ions, fluoroalkylsulfonates such as triflate, 1,1,1-trifluoroethanesulfonate, pentafluoroethanesulfonate, and nonafluorobutanesulfonate, arylsulfonates such as tosylate, benzenesulfonate, 4-fluorobenzenesulfonate, and 1,2,3,4,5-pentafluorobenzenesulfonate, alkylsulfonates such as mesylate and butanesulfonate, conjugate bases of imide acids such as bis(trifluoromethylsulfonyl)imide, bis(perfluoroethylsulfonyl)imide, bis(perfluoropropylsulfonyl)imide, and bis(perfluorobutylsulfonyl)imide, methide acids such as tris(trifluoromethylsulfonyl)methide and tris(perfluoroethylsulfonyl)methide, and mineral acids such as $BF_4^-$, $PF_6^-$, $ClO_4^-$, $NO_3^-$, and $SbF_6^-$. Preferably $X_a^-$ is triflate, 1,1,1-trifluoroethanesulfonate, pentafluoroethanesulfonate, and nonafluorobutanesulfonate, conjugate bases of bis(trifluoromethylsulfonyl)imide acid, and conjugate bases of tris(trifluoromethylsulfonyl)methide acid. $R^{44}$, $R^{55}$, and $R^{66}$ are each independently hydrogen, halogen, cyano, amino, $-R^{1a}$, $-OR^{1a}$, $SR^{1a}$, $-O_2CR^{1a}$, $-CO_2R^{1a}$, or $-N(R^{1a})_2$, and c1, c2 and c3 are each independently an integer of 0 to 5. $R^{77}$, and $R^{88}$, $R^{99}$, and $R^{110}$ are each independently hydrogen, halogen, cyano, amino, $-R^{1a}$, $-Or^{1a}$, $-SR^{1a}$, $-O_2CR^{1a}$, $-CO_2R^{1a}$, or $-N(R^{1a})_2$, and d1, d2, d3 and d4 are each independently an integer of 0 to 5. $R^{111}$, $R^{112}$, $R^{113}$, and $R^{114}$ are each independently hydrogen, halogen, cyano, amino, $-R^{1a}$, $-OR^{1a}$, $SR^{1a}$, $-O_2CR^{1a}$, $-CO_2R^{1a}$, or $-N(R^{1a})_2$, and f1, f2, f3 and f4 are each independently an integer of 0 to 5. The subscript e is 1 or 2. $R^{1a}$ is an optionally substituted monovalent hydrocarbon group of 1 to 20 carbon atoms, preferably 1 to 12 carbon atoms, which may contain a heteroatom, typically an alkyl group or a fluoro, cyano or hydroxyl-substituted alkyl group.

Exemplary structures of the cation of the other NIR absorbing dyes of formulae (12) to (14) are shown below, but not limited thereto.

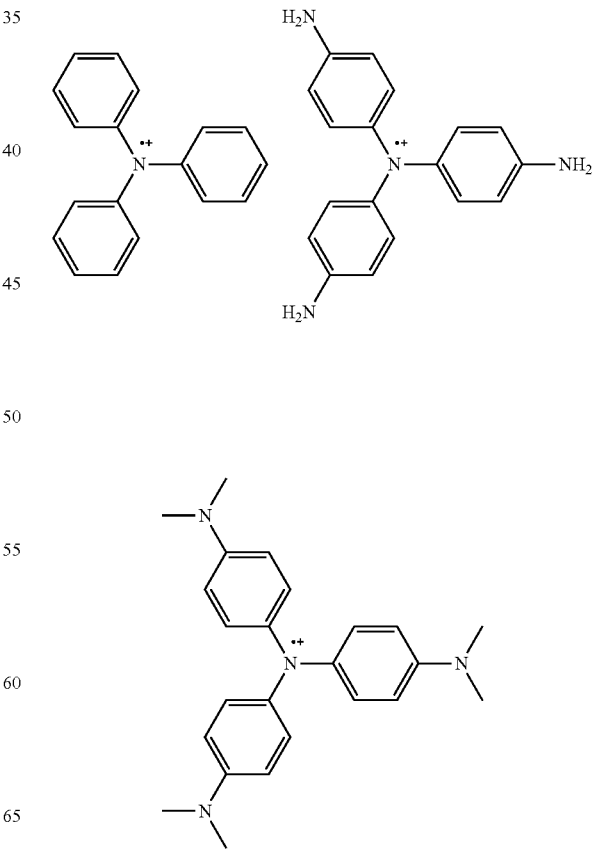

25
-continued
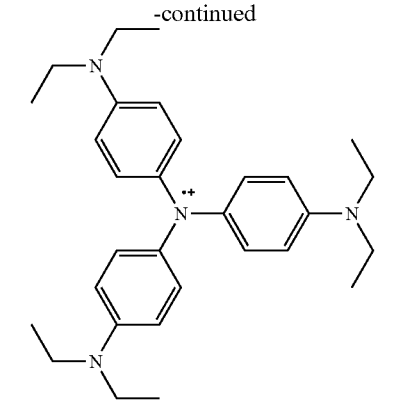
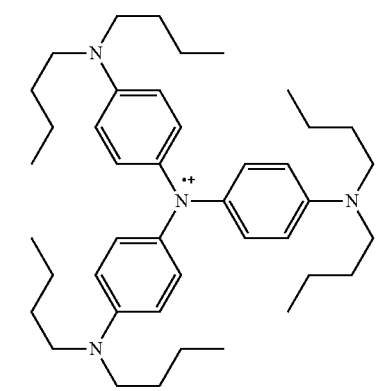
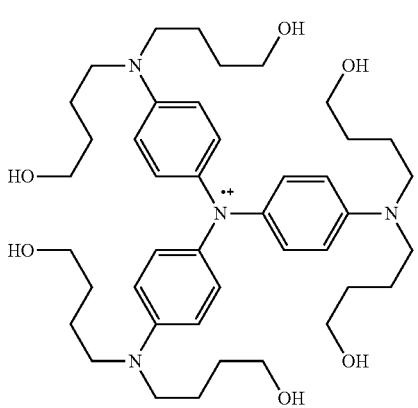
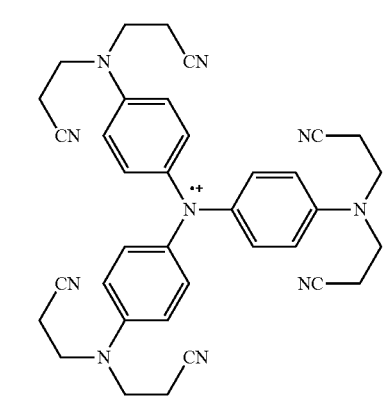
26
-continued
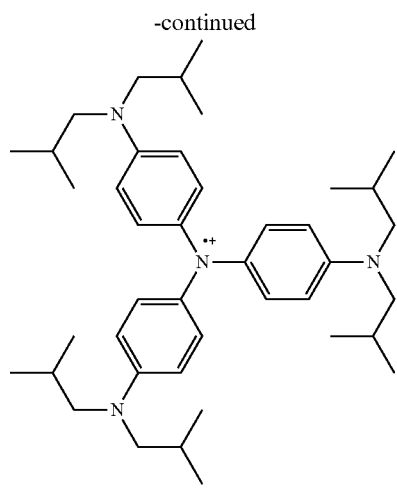
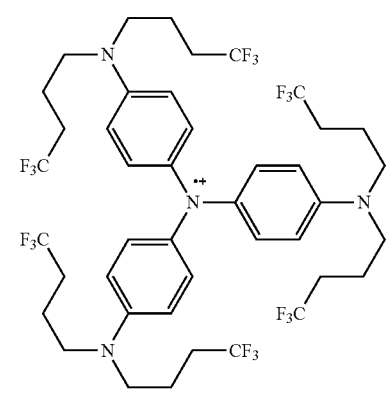
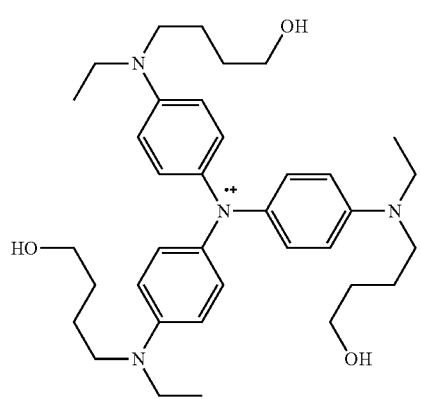
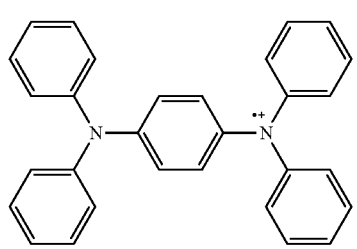

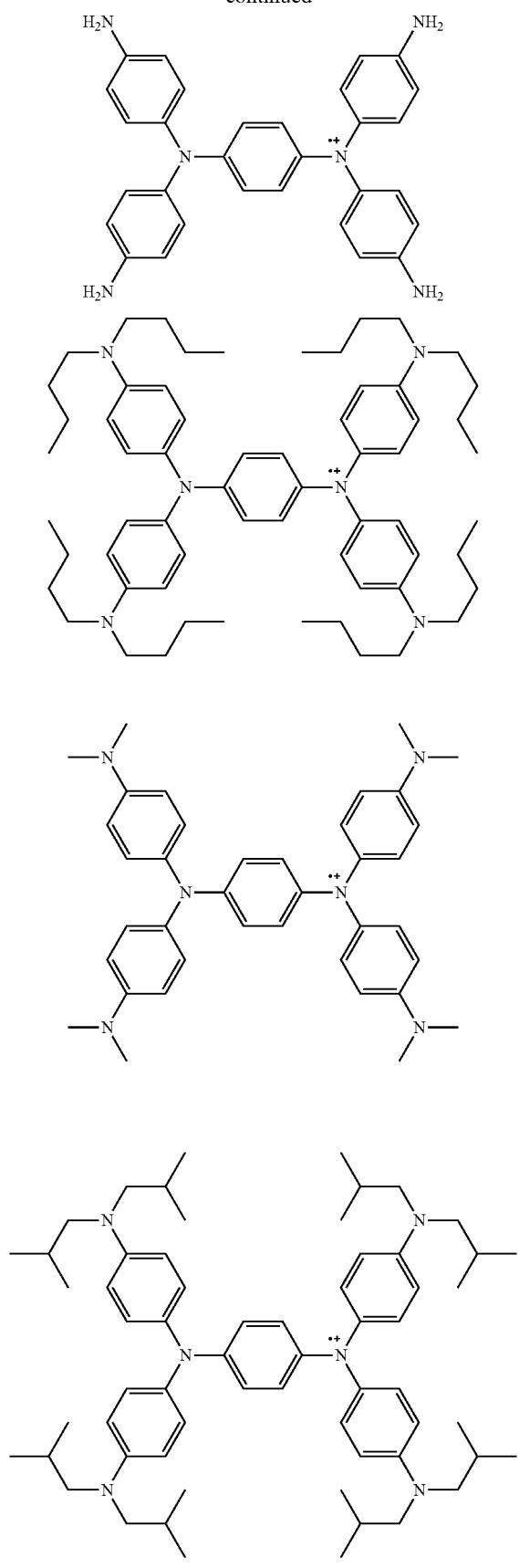
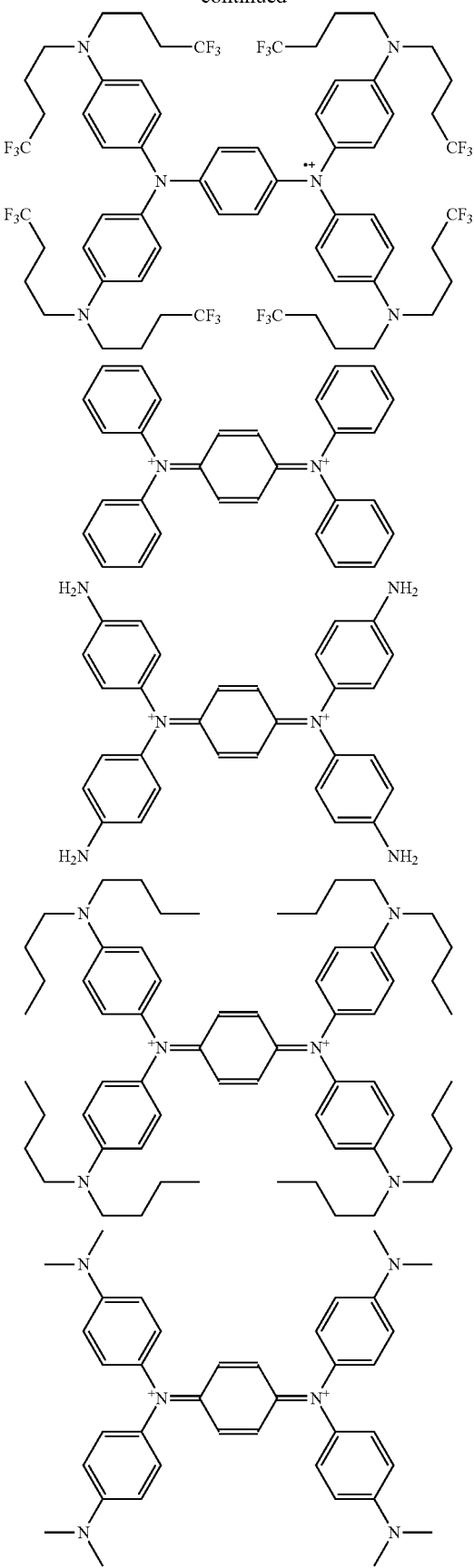

-continued

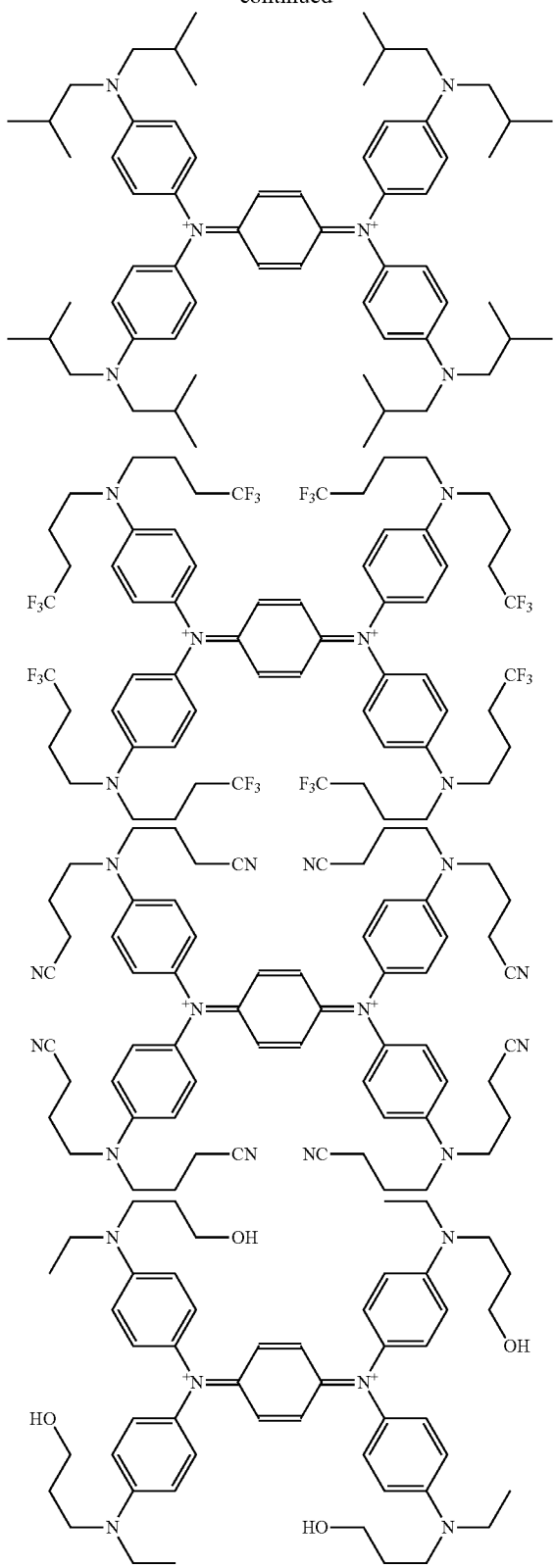

The other NIR absorbing dye may be selected from commercially available dyes as purchased. It may also be derived from such a commercial dye as the precursor or prepared by any well-known organic chemistry procedures.

In the NIR absorptive film-forming composition, the NIR absorbing dye(s) is preferably used in an amount of 20 to 100 parts, more preferably 40 to 100 parts by weight per 100 parts by weight of the overall solids.

B) Solvent

At least one solvent is present in the NIR absorptive film-forming composition. The solvent used herein may be any organic solvent in which the NIR absorbing dye, polymer, thermal acid generator, crosslinker, surfactant and other components are soluble. Illustrative, non-limiting, examples of the organic solvent include ketones such as cyclopentanone, cyclohexanone and methyl-2-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, PGMEA, cyclohexanone, γ-butyrolactone, and mixtures thereof are preferably used in the NIR absorptive film-forming composition.

The organic solvent is preferably added in an amount of 900 to 20,000 parts by weight, more preferably 1,000 to 15,000 parts by weight per 100 parts by weight of the overall solids.

C) Polymer

Most often the NIR absorptive film-forming composition further comprises at least one polymer, particularly when the composition is used in the fabrication of optical filers, to form an antireflective coating for improving the accuracy of optical auto-focusing in the fabrication of semiconductor devices, or as NIR-sensitive ink. The polymer used herein may be selected from a wide variety of polymers. Exemplary polymers include polyvinyl compounds such as polyethylene, polyacetylene, polyacrylic acid, polyvinyl acetate, polyacrylonitrile, polyvinyl chloride, polystyrene, polyvinyl fluoride, polymethacrylate, polyvinylidene chloride, and polyvinylidene cyanide; fluorinated resins such as polyvinylidene fluoride, polytrifluoroethylene, polytetrafluoroethylene, and polyhexafluoropropylene; polyamides such as nylon 6, nylon 66, polyimides, polyurethane, polypeptides, polyesters such as polyethylene terephthalate, polycarbonate, polyethers such as polyoxymethylene, epoxy resins, polyvinyl alcohol, and polyvinyl butyral. These resins may have a variety of functional groups in their structure, and examples of such resins include:

polymers of substituted styrene compounds such as p-hydroxystyrene, p-methoxystyrene, p-chlorostyrene, p-carboxystyrene, α-methylstyrene, m-methylstyrene, and p-methylstyrene;

polymers of p-hydroxystyrene compounds whose hydroxyl has been substituted such as p-acetoxystyrene, p-t-butoxystyrene, p-methoxymethoxystyrene, and p-t-butoxycarbonyloxystyrene;

polymers of p-carboxystyrene compounds whose carboxyl has been substituted such as p-methoxycarbonylstyrene and p-t-butoxycarbonylstyrene;

polymers of aromatic group-containing vinyl compounds such as indene, acenaphthylene, vinylnaphthalene, hydroxyvinylnaphthalene, and methoxyvinylnaphthalene;

polymers of alkyl(meth)acrylates such as methyl(meth)acrylate, ethyl(meth)acrylate, n-propyl(meth)acrylate, isopropyl(meth)acrylate, n-butyl(meth)acrylate, s-butyl(meth)acrylate, isobutyl(meth)acrylate, and t-butyl(meth)acrylate;

polymers of aryl(meth)acrylates such as phenyl(meth)acrylate, benzyl(meth)acrylate, phenethyl(meth)acrylate, 1-naphthyl(meth)acrylate, and 2-naphthyl(meth)acrylate;

polymers of hydroxyl-containing (meth)acrylates such as 2-hydroxyethyl(meth)acrylate, 2-hydroxypropyl(meth)acrylate, 3-hydroxypropyl(meth)acrylate, 2-hydroxybutyl(meth)acrylate, 3-hydroxybutyl(meth)acrylate, 4-hydroxybutyl(meth)acrylate, 5-hydroxypentyl(meth)acrylate, 6-hydroxyhexyl(meth)acrylate, 7-hydroxyheptyl(meth)acrylate, 8-hydroxyoctyl(meth)acrylate, 9-hydroxynonyl(meth)acrylate, 10-hydroxydecyl(meth)acrylate, 11-hydroxyundecyl(meth)acrylate, and 12-hydroxydodecyl(meth)acrylate;

polymers of alicyclic structure-containing (meth)acrylates such as cyclopentyl(meth)acrylate, cyclohexyl(meth)acrylate, bicyclo[2.2.1]hept-5-en-2-yl(meth)acrylate, and adamantan-1-yl(meth)acrylate;

polymers of lactone-containing (meth)acrylates such as pantoyllactone (meth)acrylate, α-(meth)acryloyl-γ-butyrolactone, and β-(meth)acryloyl-γ-butyrolactone;

polymers of unsaturated monocarboxylic acids such as crotonic acid, 2-acryloyloxyethylsuccinic acid, 2-acryloyloxyethylhexahydrophthalic acid, phthalic acid monohydroxyethyl acrylate, 2-methacryloyloxyethylsuccinic acid, 2-methacryloyloxyethylhexahydrophthalic acid, and phthalic acid monohydroxyethyl methacrylate;

polymers of unsaturated dicarboxylic acids or anhydrides such as maleic acid, fumaric acid, citraconic acid, mesaconic acid, and itaconic acid;

polymers of polycyclic unsaturated carboxylic acids such as 5-carboxybicyclo[2.2.1]hept-2-ene, 5-carboxy-5-methylbicyclo[2.2.1]hept-2-ene, 5-carboxy-5-ethylbicyclo[2.2.1]hept-2-ene, 5-carboxy-6-methylbicyclo[2.2.1]hept-2-ene, and 5-carboxy-6-ethylbicyclo[2.2.1]hept-2-ene;

polymers of polycyclic unsaturated dicarboxylic acids or anhydrides such as 5,6-dicarboxybicyclo[2.2.1]hept-2-ene;

polymers of oxiranyl-containing (meth)acrylates such as glycidyl(meth)acrylate, 2-methylglycidyl(meth)acrylate, 3,4-epoxybutyl(meth)acrylate, 6,7-epoxyheptyl(meth)acrylate, 3,4-epoxycyclohexyl(meth)acrylate, and 3,4-epoxycyclohexylmethyl(meth)acrylate;

polymers of oxiranyl-containing α-alkylacrylates such as glycidyl α-ethylacrylate, glycidyl α-n-propylacrylate, glycidyl α-n-butylacrylate, and 6,7-epoxyheptyl α-ethylacrylate;

polymers of glycidyl ethers such as o-vinylbenzyl glycidyl ether, m-vinylbenzyl glycidyl ether, and p-vinylbenzyl glycidyl ether;

polymers of oxetanyl-containing (meth)acrylates such as 3-((meth)acryloyloxymethyl)oxetane, 3-((meth)acryloyloxymethyl)-3-ethyloxetane, 3-((meth)acryloyloxymethyl)-2-methyloxetane, 3-((meth)acryloyloxymethyl)-2-phenyloxetane, 3-((meth)acryloyloxyethyl)oxetane, 3-((meth)acryloyloxyethyl)-3-ethyloxetane, 2-ethyl-3-((meth)acryloyloxyethyl)oxetane, 3-((meth)acryloyloxyethyl)-2-phenyloxetane, 2-((meth)acryloyloxymethyl)oxetane, 2-methyl-2-((meth)acryloyloxymethyl)oxetane, 3-methyl-2-((meth)acryloyloxymethyl)oxetane, 4-methyl-2-((meth)acryloyloxymethyl)oxetane, 2-((meth)acryloyloxymethyl)-2-phenyloxetane, 2-((meth)acryloyloxymethyl)-3-phenyloxetane, 2-((meth)acryloyloxymethyl)-4-phenyloxetane, 2-((meth)acryloyloxyethyl)oxetane, 2-((meth)acryloyloxyethyl)-2-methyloxetane, 2-((meth)acryloyloxyethyl)-4-methyloxetane, 2-((meth)acryloyloxyethyl)-2-phenyloxetane, 2-((meth)acryloyloxyethyl)-3-phenyloxetane, 2-((meth)acryloyloxyethyl)-4-phenyloxetane; and copolymers comprising two or more of the foregoing combined.

The epoxy resin may be selected from commercially available resins. Examples include bisphenol A epoxy resins such as Epikote 1001, 1002, 1003, 1004, 1007, 1009, 1010, and 828 (Japan Epoxy Resin Co., Ltd.), bisphenol F epoxy resins such as Epikote 807 (Japan Epoxy Resin Co., Ltd.), phenol novolac epoxy resins such as Epikote 152, 154, and 157S65 (Japan Epoxy Resin Co., Ltd.), and EPPN 201 and 202 (Nippon Kayaku Co., Ltd.), cresol novolac epoxy resins such as EOCN 102, 103S, 104S, 1020, 1025, and 1027 (Nippon Kayaku Co., Ltd.) and Epikote 180S75 (Japan Epoxy Resin Co., Ltd.), polyphenol epoxy resins such as Epikote 1032H60 and XY-4000 (Japan Epoxy Resin Co., Ltd.), and alicyclic epoxy resins such as CY-175, 177 and 179, Araldite CY-182, 192, and 184 (Ciba Specialty Chemicals), ERL-4234, 4299, 4221, and 4206 (U.C.C.), Shodyne 509 (Showa Denko K. K.), Epiclon 200 and 400 (DIC Corp.), Epikote 871 and 872 (Japan Epoxy Resin Co., Ltd.), ED-5661 and 5662 (Celanese Coating).

The polymer (C) may comprise individual repeat units in a preferred compositional proportion range as shown below, but is not limited thereto. Specifically, the polymer may preferably comprise:

10 to 100 mol %, more preferably 20 to 100 mol %, and even more preferably 30 to 100 mol % of aromatic ring-bearing repeat units, 0 to 90 mol %, more preferably 0 to 70 mol %, and even more preferably 0 to 60 mol % of repeat units which undergo crosslinking reaction, and 0 to 40 mol %, more preferably 0 to 30 mol %, and even more preferably 0 to 20 mol % of other repeat units, provided that these units total to 100 mol %.

The monomer(s) from which the polymer used herein is derived may be selected from commercially available monomers as purchased. They may also be prepared using any well-known organic chemistry procedures.

The polymer may be prepared by any polymerization reactions, but preferably radical polymerization. For radical polymerization, preferred reaction conditions include (1) a solvent selected from hydrocarbon solvents such as benzene, toluene and xylene, glycol solvents such as propylene glycol monomethyl ether and propylene glycol monomethyl ether acetate, ether solvents such as diethyl ether, diisopropyl ether, dibutyl ether, tetrahydrofuran, and 1,4-dioxane, ketone solvents such as acetone, methyl ethyl ketone, methyl isobutyl ketone and methyl amyl ketone, ester solvents such as ethyl acetate, propyl acetate, butyl acetate and ethyl lactate, lactone solvents such as γ-butyrolactone, and alcohol solvents such as ethanol and isopropyl alcohol;

(2) a polymerization initiator selected from well-known radical polymerization initiators including azo compounds such as 2,2'-azobisisobutyronitrile, 2,2'-azobis-2-methylisobutyronitrile, dimethyl 2,2'-azobisisobutyrate, 2,2'-azobis-2,4-dimethylvaleronitrile, 1,1'-azobis(cyclohexane-1-carbonitrile), and 4,4'-azobis(4-cyanovaleric acid), and peroxides such as lauroyl peroxide and benzoyl peroxide;

(3) a radical chain transfer agent, if necessary for molecular weight control, selected from thiol compounds including 1-butanethiol, 2-butanethiol, 2-methyl-1-propanethiol, 1-octanethiol, 1-decanethiol, 1-tetradecanethiol, cyclohexanethiol, 2-mercaptoethanol, 1-mercapto-2-propanol, 3-mercapto-1-propanol, 4-mercapto-1-butanol, 6-mercapto-1-hexanol, 1-thioglycerol, thioglycolic acid, 3-mercaptopropionic acid, and thiolactic acid;

(4) a reaction temperature in the range of about 0° C. to about 140° C.; and (5) a reaction time in the range of about 0.5 to about 48 hours. Reaction parameters outside these ranges need not be excluded.

The polymer used herein preferably has a weight average molecular weight (Mw) of 1,000 to 200,000, and more preferably 2,000 to 180,000, as measured in tetrahydrofuran by gel permeation chromatography (GPC) versus polystyrene standards. A polymer having too high a Mw may not dissolve in a solvent or may dissolve in a solvent to form a solution, which may be less effective to coat, failing to form a film of uniform thickness over the entire wafer surface. Also, when a polymer film is formed on a patterned substrate, the film may fail to cover the pattern without leaving voids. On the other hand, a polymer having too low a Mw may have a problem that when a polymer film is overlaid with another film, the polymer film is in part washed away and thinned.

The NIR absorptive film-forming composition is defined as comprising (A) a NIR absorbing dye of formula (1), (B) a solvent, and (C) a polymer, all described above, and optionally further comprising (D) an acid generator, (E), a crosslinker, and/or (F) a surfactant.

D) Acid Generator

In the NIR absorptive film-forming composition, an acid generator may be added for the purpose of promoting crosslinking reaction (induced thermally or otherwise) so that a coating may cure more effectively. The acid generators include those capable of generating an acid through thermal decomposition (thermal acid generators) and those capable of generating an acid upon light exposure (photoacid generators). Although acid generators of either category may be added, the thermal acid generators are preferred.

Suitable acid generators used herein include sulfonium salts, iodonium salts, ammonium salts, and diazomethanes. While any of these acid generators may be used herein, typical acid generators are illustrated in JP-A 2008-083668. The preferred acid generators are onium salts having α-fluoro-substituted sulfonate as an anion including triethylammonium nonafluorobutanesulfonate,
(p-methoxyphenylmethyl)dimethylphenylammonium trifluoromethanesulfonate,
bis(p-tert-butylphenyl)iodonium nonafluorobutanesulfonate,
triphenylsulfonium trifluoromethanesulfonate,
(p-tert-butoxyphenyl)diphenylsulfonium trifluoromethanesulfonate,
tris(p-tert-butoxyphenyl)sulfonium trifluoromethanesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocyclohexyl)sulfonium trifluoromethanesulfonate, and
1,2'-naphthylcarbonylmethyltetrahydrothiophenium triflate.

The acid generators may be used alone or in admixture of two or more.

The acid generator is preferably added in an amount of 0.1 to 50 parts by weight, more preferably 0.5 to 40 parts by weight per 100 parts by weight of the overall solids in the NIR absorptive film-forming composition. No less than 0.1 pbw of the acid generator may generate an acid in an amount sufficient to promote crosslinking reaction whereas no more than 50 pbw may substantially avoid the risk that the acid will be leached out of the film.

The NIR absorptive film-forming composition may comprise a resin having a crosslinkable group, a crosslinker, and an acid generator. This formulation is intended to form a cured film through crosslinking reaction upon bake. To enhance a crosslinking ability during the process, an acid generator having an anion which is a conjugate base of strong acid is preferably used. Therefore, if the anion of the NIR absorbing dye is a conjugate base of weak acid, for example, chloride ion, bromide ion, iodide ion or tosylate, then the dye can undergo exchange reaction with the anion of the acid generator and as a result, the acid generator may fail to exert the desired function. This results from the likelihood that a conjugate base of strong acid may form an ion pair with an onium cation. Therefore, a conjugate base of strong acid, which is equal to or more than the acid generator used, typically α,α-difluorosulfonate anion is preferably selected as the anion of the NIR absorbing dye.

Notably, the anion structure of the NIR absorbing dye according to the invention is a sulfonate having fluoro-substitution at α-position. This indicates that the anion is a conjugate base of strong acid. Therefore, the NIR absorbing dye does not undergo exchange reaction with the anion of the acid generator and hence, does not detract from the function of the acid generator. Although an inorganic anion such as hexafluoroantimonate or tetrafluoroborate is also a conjugate base of strong acid, a NIR absorbing dye having such an inorganic anion is not preferred because the metal impurity resulting from the anion can have an impact on the performance during the semiconductor device fabrication process. Furthermore, although perfluoroalkyl compounds such as nonafluorobutanesulfonate are strong acid anions, they are undesirably used because their stability (anti-degradation) assigned to C—F bonds and the biological concentration and accumulation due to hydrophobic and lipophilic properties are of concern. Although a conjugate base of bis(trifluoromethylsulfonyl)imide acid is a conjugate base of strong acid surpassing the anion of the NIR absorbing dye of the invention, it is not practically acceptable because of the lack of solvent solubility. In contrast, the NIR absorbing dye of the invention has good solvent solubility, and the NIR absorptive film-forming composition comprising the same is fully curable after coating. Therefore, the NIR absorbing dye of the invention is applicable to a wide variety of uses and suitable for use, for example, in optical filters and antireflective coatings for improving the accuracy of optical auto-focusing in the semiconductor device fabrication process. Although the NIR absorbing dye contains fluorine atoms in its anion structure, the dye wherein $R^0$ in formula (1) is hydroxyl is a low molecular weight, low accumulative fluorine compound, which is regarded as having least impact on the human body and the environment. The compound wherein $R^0$ is –OC(=O)—R' is also is regarded as having least impact on the human body and the environment because it may be converted through alkaline hydrolysis into the same compound wherein $R^0$ is hydroxyl. Decomposed compounds are amenable to disposal by burning because they are combustible due to low fluorine substitution.

E) Crosslinker

To the NIR absorptive film-forming composition, a crosslinker is preferably added. When the composition is used to form an antireflective coating for improving the accuracy of optical auto-focusing in the semiconductor device fabrication process, for example, the film is desired to avoid intermixing with any overlying layer, typically resist layer, to prevent diffusion of low molecular weight components, and/or to have resistance to the rinsing step after film formation. These goals may be attained by the method of applying the NIR absorptive film-forming composition onto a substrate by a coating technique such as spin coating, and then baking to induce thermal crosslinking to form a cured film. This method becomes employable if a crosslinker is added to the NIR absorptive film-forming composition or if a crosslinkable substituent group is introduced into the polymer.

Suitable crosslinkers which can be added herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. Acid anhydrides, oxazoline compounds, and compounds having a plurality of hydroxyl groups are also useful as the crosslinker. Typical crosslinkers are illustrated in JP-A 2009-098639. Preferred examples of the crosslinker include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof.

In the NIR absorptive film-forming composition, the crosslinker is preferably added in an amount of 0 to 50 parts by weight, more preferably 1 to 40 parts by weight per 100 parts by weight of the overall solids. An appropriate amount of the crosslinker is effective for curing a layer. However, if the amount is more than 50 pbw, part of the crosslinker may be released as outgas upon film formation, causing contamination to the exposure apparatus. The crosslinkers may be used alone or in admixture of two or more.

F) Surfactant

In a preferred embodiment, the NIR absorptive film-forming composition further comprises a surfactant. Illustrative, non-limiting, examples of the surfactant (F) include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Jemco Co., Ltd.), Megaface F171, F172, F173, R08 and R30 (DIC Corp.), Fluorad FC-430, FC-431, FC-4430 and FC-4432 (3M Sumitomo Co., Ltd.), Asahiguard AG710, Surflon S-381, S-382, SC101, SC102, SC103, SC104, SC105, SC106, KH-10, KH-20, KH-30 and KH-40 (Asahi Glass Co., Ltd.), and Surfynol E1004 (Nissin Chemical Industry Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Kagaku Kogyo Co., Ltd.). Additional useful surfactants include partially fluorinated oxetane ring-opened polymers having the structural formula (surf-1).

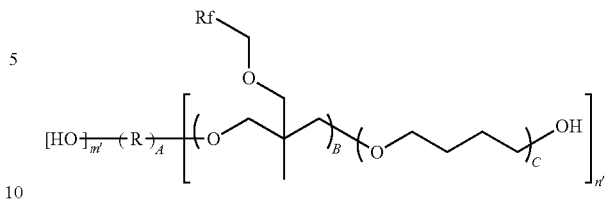

In formula (surf-1), R is a di- to tetra-valent $C_1$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

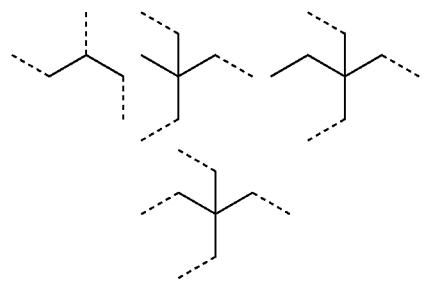

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20, KH-30, and oxetane ring-opened polymers of formula (surf-1) are preferred. These surfactants may be used alone or in admixture.

To the NIR absorptive film-forming composition, the surfactant is preferably added in an amount of up to 2 parts, more preferably up to 1 part by weight, relative to 100 parts by weight of the overall solids. When the surfactant is used, the amount is preferably at least 0.01 pbw.

When the NIR absorptive film-forming composition is coated, the resulting film contains the dye capable of absorbing radiation in a wavelength range of 500 to 1,200 nm, specifically 800 to 1,200 nm so that it may function as a film for absorbing NIR radiation in the wavelength range.

The composition is used to form a NIR absorptive film. Specifically, the NIR absorptive film can be formed on a substrate by any suitable coating techniques including spin coating, roll coating, flow coating, dip coating, spray coating, and doctor coating. Inter alia, spin coating is preferred since it is convenient to form a uniform film. The spin coating technique is generally used as the technique of forming a photoresist film in the semiconductor device fabrication process. Since the NIR absorptive film-forming composition is characterized by good solvent solubility, a uniform film can be formed therefrom by the spin coating technique.

EXAMPLE

Examples of the invention are given below by way of illustration and not by way of limitation.

Synthesis Example 1-1

Synthesis of 3-butyl-2-(2-{3-[2-(3-butyl-1,1-dimethyl-1,3-dihydrobenzo[e]indol-2-ylidene)ethylidene]-2-(phenylsulfonyl)cyclopent-1-en-1-yl}ethenyl)-1,1-dimethyl-1H-benzo[e]indol-1-ium 1,1,3,3,3-pentafluoro-2-(pivaloyloxy)-propanesulfonate, designated Dye-A

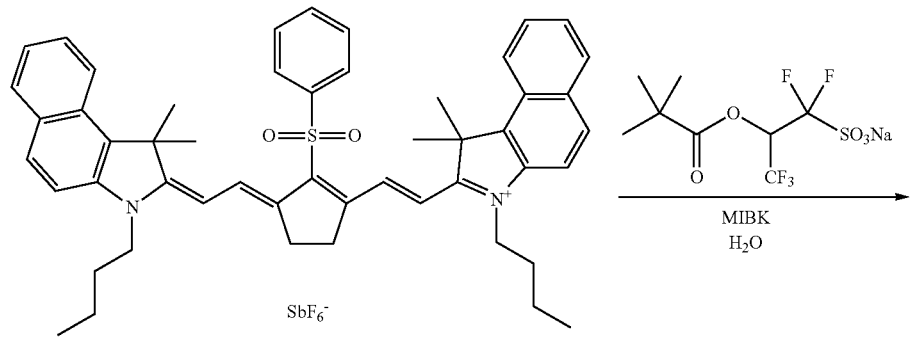

A mixture of 5.0 g (5 mmol) of 3-butyl-2-(2-{3-[2-(3-butyl-1,1-dimethyl-1,3-dihydrobenzo[e]indol-2-ylidene)-ethylidene]-2-(phenylsulfonyl)cyclopent-1-en-1-yl}ethenyl)-1,1-dimethyl-1H-benzo[e]indol-1-ium hexafluoroantimonate, 2.5 g (7.5 mmol) of sodium 1,1,3,3,3-pentafluoro-2-(pivaloyloxy)propanesulfonate, 40 g of water, and 40 g of methyl isobutyl ketone was stirred for 7 hours at room temperature, whereupon the organic layer was taken out. The organic layer was combined with 0.8 g (2.5 mmol) of sodium 1,1,3,3,3-pentafluoro-2-(pivaloyloxy)propanesulfonate and 40 g of water and stirred overnight, whereupon the organic layer was taken out. The organic layer was washed with water and concentrated in vacuum. Diisopropyl ether was added to the residue for recrystallization. The crystal was collected and dried in vacuum, obtaining the target compound, 3-butyl-2-(2-{3-[2-(3-butyl-1,1-dimethyl-1,3-dihydrobenzo-[e]indol-2-ylidene)ethylidene]-2-(phenylsulfonyl)cyclopent-1-en-1-yl}ethenyl)-1,1-dimethyl-1H-benzo[e]indol-1-ium 1,1,3,3,3-pentafluoro-2-(pivaloyloxy)propanesulfonate. Brown crystal, 5.1 g, yield 95%.

Figure 2:
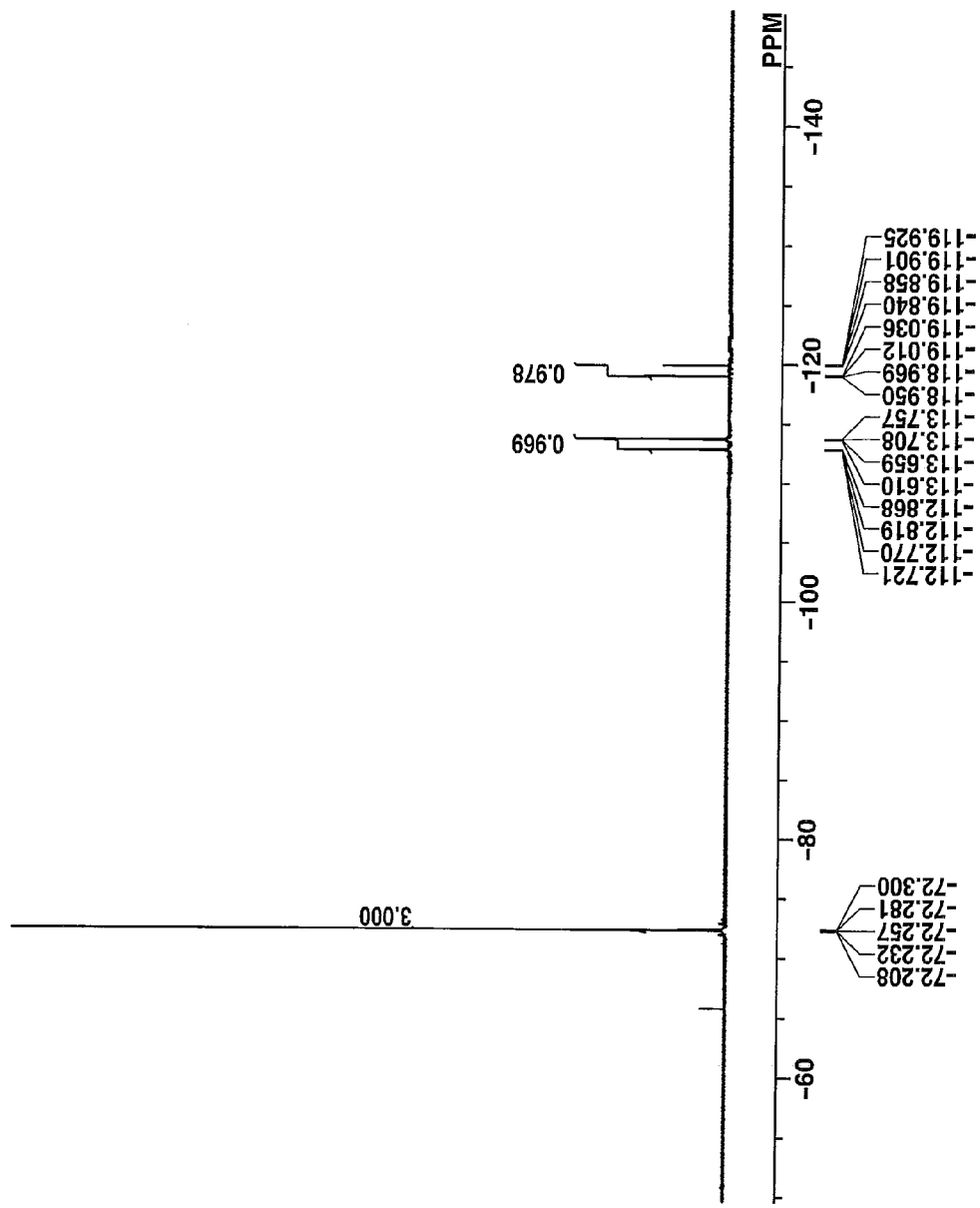

The compound was analyzed by attenuated total reflection infrared absorption and nuclear magnetic resonance spectroscopies. The spectral data are shown below. The NMR spectra ($^1$H-NMR and $^{19}$F-NMR/DMSO-$d_6$) are shown in FIGS. 1 and 2. It is noted that in $^1$H-NMR analysis, traces of residual solvents (diisopropyl ether, methyl isobutyl ketone, water) were observed.

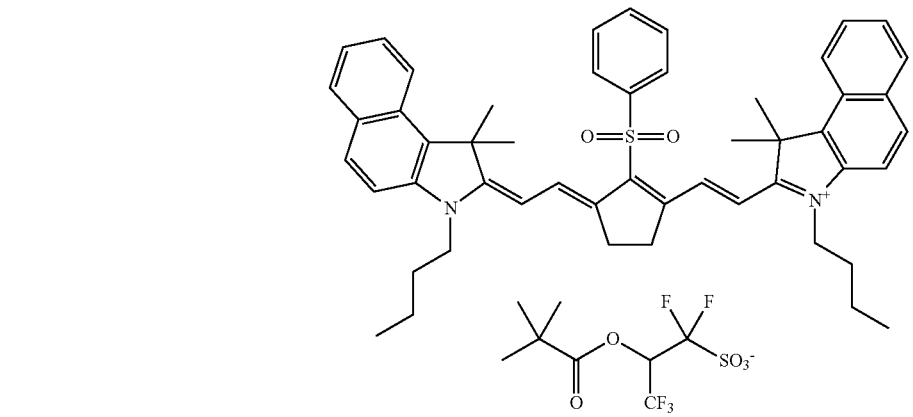

Infrared absorption spectrum IR (D-ATR)
    2961, 2931, 1757, 1532, 1500, 1460, 1441, 1430, 1416, 1386, 1350, 1271, 1224, 1162, 1093, 1010, 958, 914, 889, 830, 784, 746, 722, 677, 638, 588 cm$^{-1}$ Time-of-flight mass spectroscopy (TOF-MS); MALDI
    Positive M$^+$759 (corresponding to $C_{51}H_{55}N_2O_2S$)
    Negative M$^-$312 (corresponding to $C_8F_5O_5S$)

Synthesis Example 1-2

Synthesis of 2-(2-[(3-{(2-(1,1-dimethyl-3-(2-hydroxyethyl)-1,3-dihydrobenzo[e]indol-2-ylidene)ethylidene]-2-(phenyl-sulfonyl)cyclopent-1-en-1-yl}ethenyl)-1,1-dimethyl-3-(2-hydroxyethyl)-1H-benzo[e]indol-1-ium 2-hydroxy-1,1,3,3,3-pentafluoropropanesulfonate, designated Dye-B

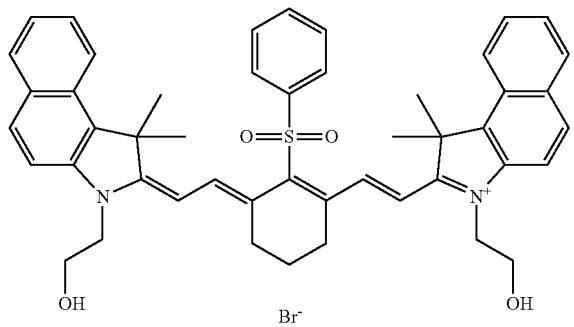
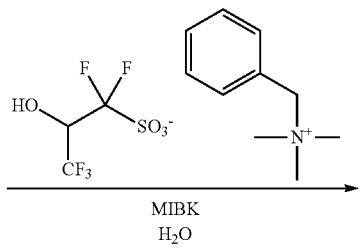
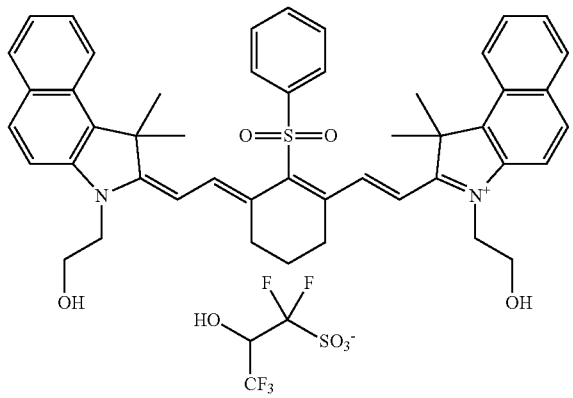

A mixture of 1.7 g (2 mmol) of 2-(2-{3-[2-(1,1-dimethyl-3-(2-hydroxyethyl)-1,3-dihydrobenzo[e]indol-2-ylidene)ethylidene]-2-(phenylsulfonyl)cyclopent-1-en-1-yl}ethenyl)-1,1-dimethyl-3-(2-hydroxyethyl)-1H-benzo[e]indol-1-ium bromide, 1.1 g (3.0 mmol) of benzyltrimethylammonium 2-hydroxy-1,1,3,3,3-pentafluoropropanesulfonate, 25 g of water, and 30 g of methyl isobutyl ketone was stirred for 6 hours at room temperature, whereupon the organic layer was taken out. The organic layer was combined with 0.8 g (2.0 mmol) of benzyltrimethylammonium 2-hydroxy-1,1,3,3,3-pentafluoropropanesulfonate and 30 g of water and stirred overnight, whereupon the organic layer was taken out. The organic layer was washed with water and concentrated in vacuum. Diisopropyl ether was added to the residue for recrystallization. The crystal was collected and dried in vacuum, obtaining the target compound, 2-(2-{3-[2-(1,1-dimethyl-3-(2-hydroxyethyl)-1,3-dihydrobenzo[e]indol-2-ylidene)ethylidene]-2-(phenylsulfonyl)cyclopent-1-en-1-yl}ethenyl)-1,1-dimethyl-3-(2-hydroxyethyl)-1H-benzo[e]indol-1-ium 2-hydroxy-1,1,3,3,3-pentafluoropropanesulfonate. Brown crystal, 1.4 g, yield 64%.

Figure 3:
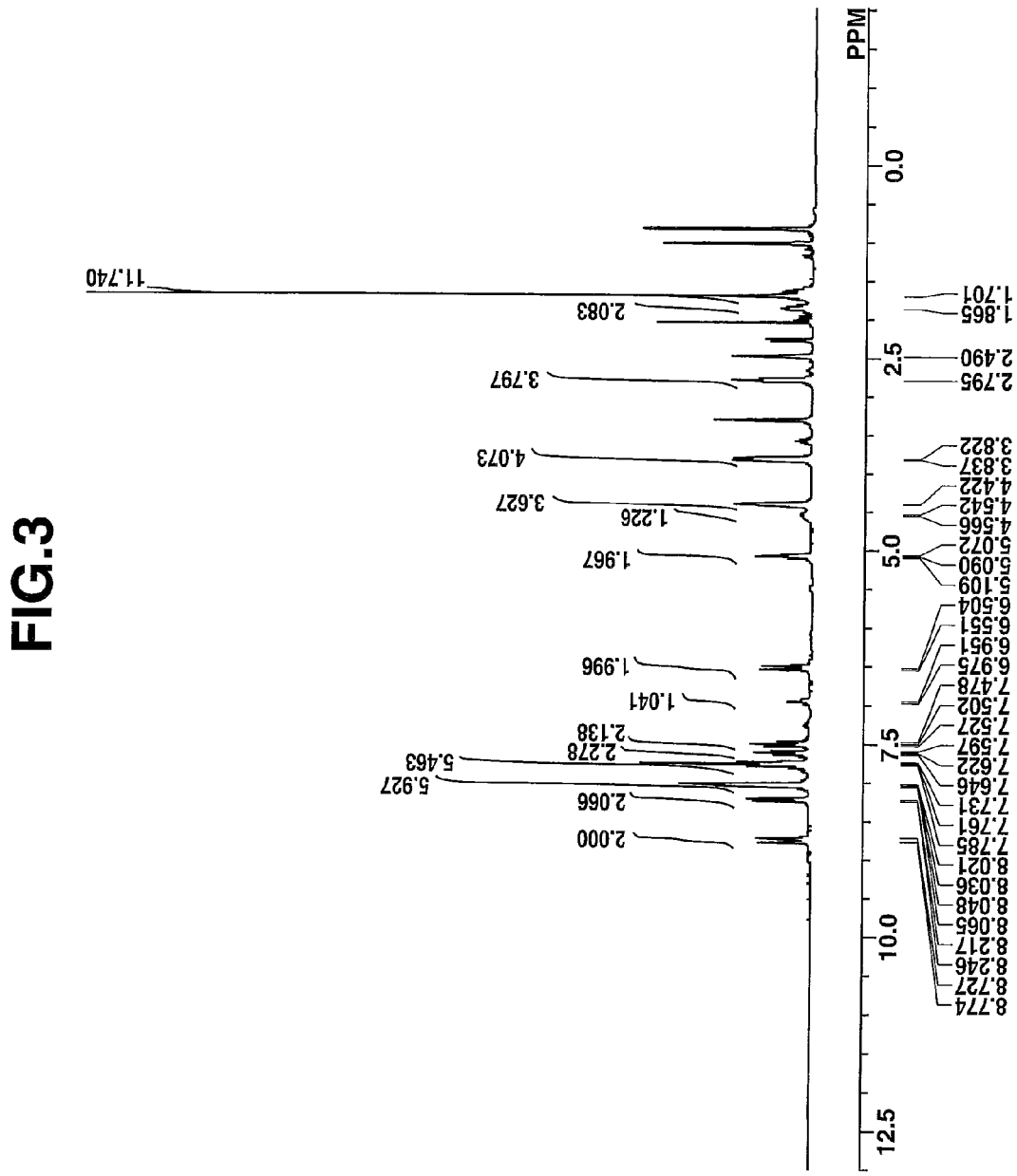
FIGS. 3 and 4 are diagrams of $^1$H-NMR and $^{19}$F-NMR/DMSO-$d_6$ spectra of Dye-B in Synthesis Example 1-2, respectively.
Figure 4:
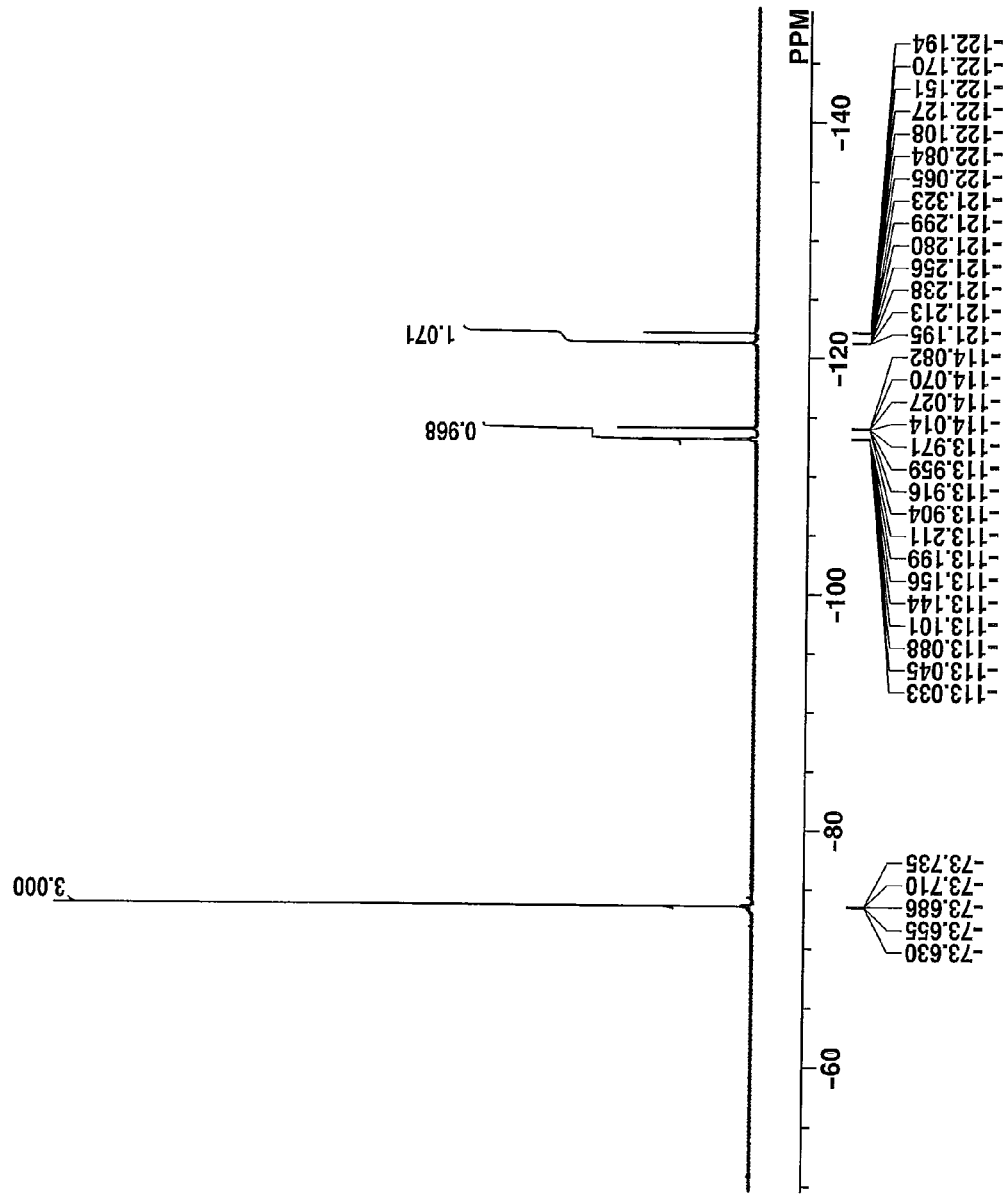

The compound was analyzed by infrared absorption and nuclear magnetic resonance spectroscopies. The spectral data are shown below. The NMR spectra ($^1$H-NMR and $^{19}$F-NMR/DMSO-$d_6$) are shown in FIGS. 3 and 4. It is noted that in $^1$H-NMR analysis, traces of residual solvents (diisopropyl ether, methyl isobutyl ketone, water) were observed.

IR (KBr)

1536, 1514, 1452, 1441, 1429, 1385, 1356, 1238, 1140, 1121, 1099, 1061, 1010, 916, 875, 859, 825, 783, 748, 723, 674, 640, 556 cm$^{-1}$

TOF-MS; MALDI

Positive M$^+$749 (corresponding to $C_{47}H_{47}N_2O_4S$)
Negative M$^-$228 (corresponding to $C_3H_2F_5O_4S$)

Synthesis Example 1-3

Synthesis of 2-(2-{3-[2-(1,1-dimethyl-3-(2-hydroxy-ethyl)-1,3-dihydrobenzo[e]indol-2-ylidene)eth-ylidene]-2-(phenyl-sulfonyl)cyclopent-1-en-1-yl}ethenyl)-1,1-dimethyl-3-(2-hydroxyethyl)-1H-benzo[e]indol-1-ium 2-(1-adamantane-carbonyloxy)-1,1,3,3,3-pentafluoropropanesulfonate, designated Dye-C

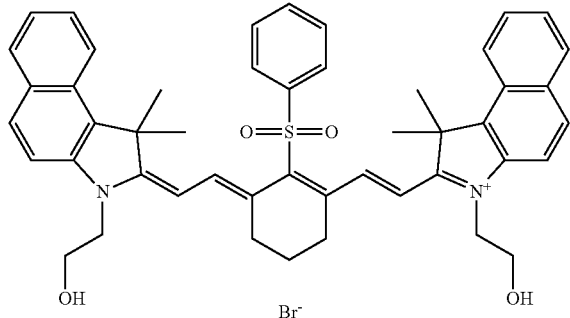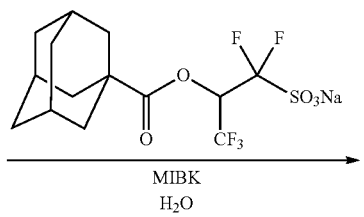

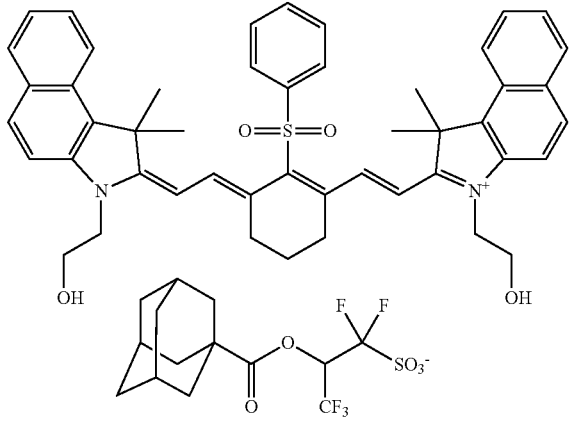

A mixture of 1.7 g (2 mmol) of 2-(2-{3-[2-(1,1-dimethyl-3-(2-hydroxyethyl)-1,3-dihydrobenzo[e]indol-2-ylidene)ethylidene]-2-(phenylsulfonyl)cyclopent-1-en-1-yl}ethenyl)-1,1-dimethyl-3-(2-hydroxyethyl)-1H-benzo[e]indol-1-ium bromide, 4.8 g (3 mmol) of 2-(1-adamantanecarbonyloxy)-1,1,3,3,3-pentafluoropropanesulfonic acid aqueous solution, 30 g of water, and 30 g of methyl isobutyl ketone was stirred for 8 hours at room temperature, whereupon the organic layer was taken out. The organic layer was combined with 1.6 g (1 mmol) of 2-(1-adamantanecarbonyloxy)-1,1,3,3,3-pentafluoro-propanesulfonic acid aqueous solution and 30 g of water and stirred overnight, whereupon the organic layer was taken out. The organic layer was washed with water and concentrated in vacuum. Diisopropyl ether was added to the residue for recrystallization. The crystal was collected and dried in vacuum, obtaining the target compound, 2-(2-{3-[2-(1,1-dimethyl-3-(2-hydroxyethyl)-1,3-dihydrobenzo[e]indol-2-ylidene)ethylidene]-2-(phenylsulfonyl)cyclopent-1-en-1-yl}ethenyl)-1,1-dimethyl-3-(2-hydroxyethyl)-1H-benzo[e]indol-1-ium 2-(1-adamantanecarbonyloxy)-1,1,3,3,3-pentafluoro-propanesulfonate. Brown crystal, 2.2 g, yield 92%.

Figure 5:
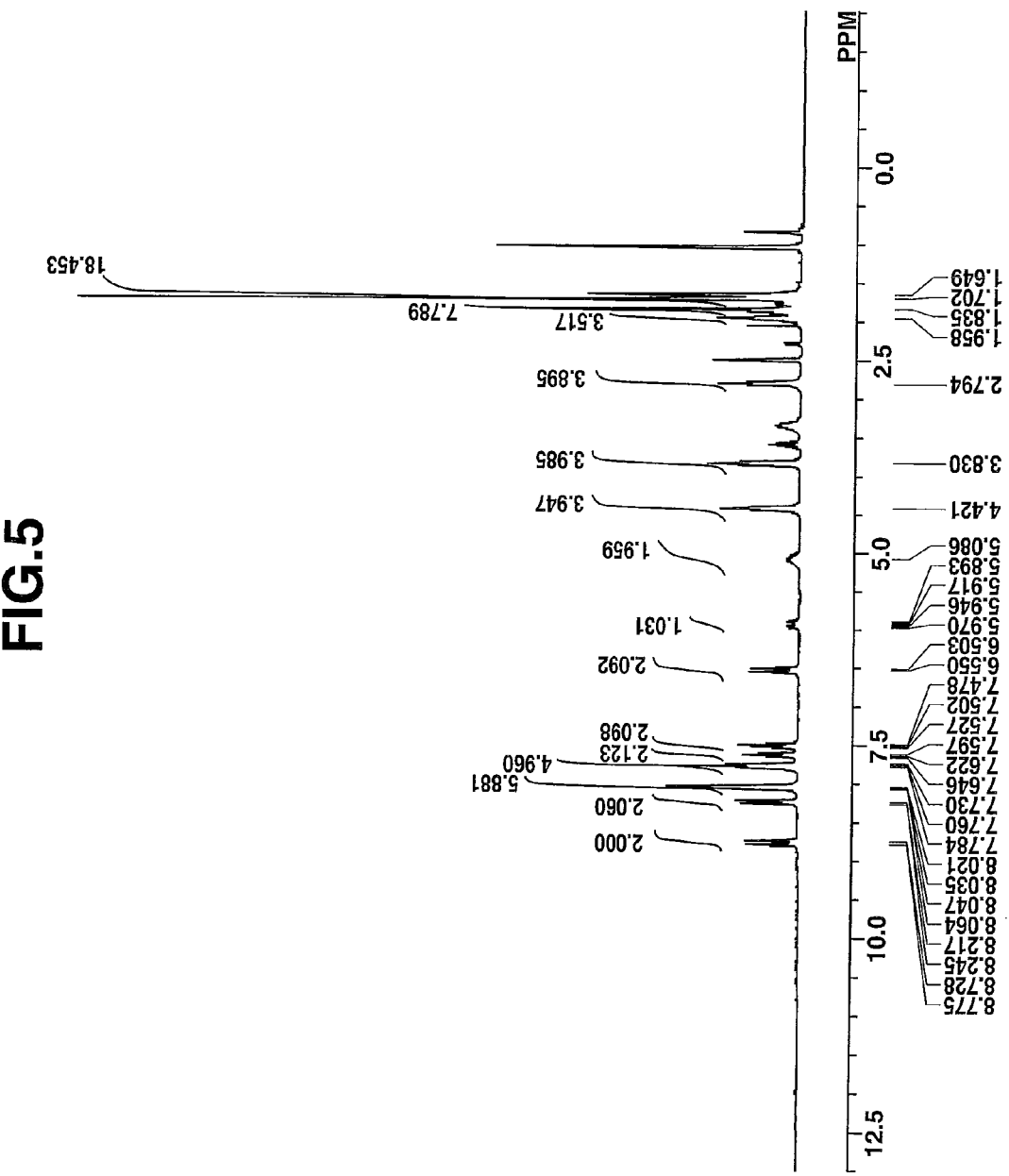
FIGS. 5 and 6 are diagrams of $^1$H-NMR and $^{19}$F-NMR/DMSO-$d_6$ spectra of Dye-C in Synthesis Example 1-3, respectively.
Figure 6:
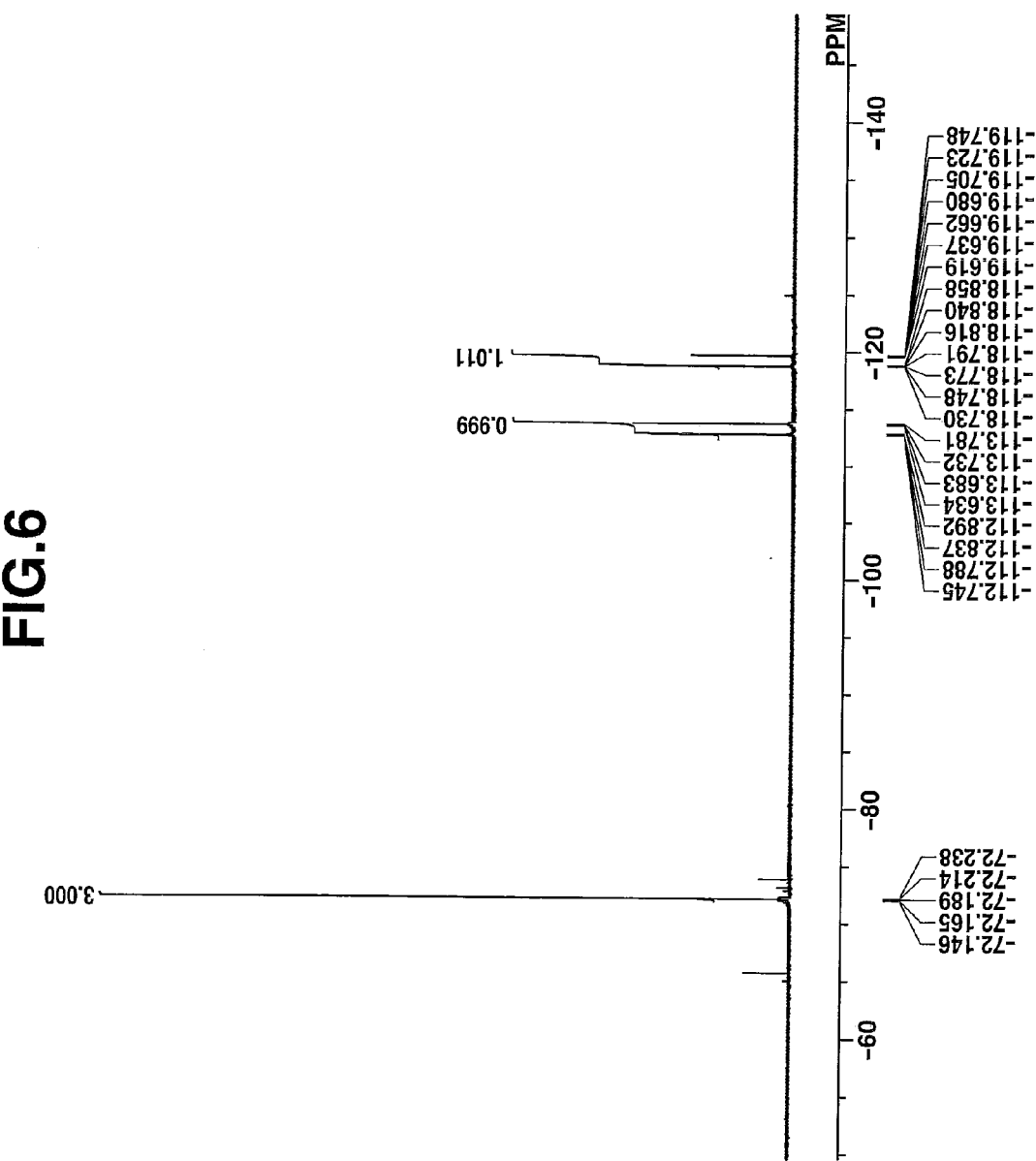

The compound was analyzed by infrared absorption and nuclear magnetic resonance spectroscopies. The spectral data are shown below. The NMR spectra ($^1$H-NMR and $^{19}$F-NMR/DMSO-$d_6$) are shown in FIGS. 5 and 6. It is noted that in $^1$H-NMR analysis, traces of residual solvents (diisopropyl ether, methyl isobutyl ketone, water) were observed.

IR (KBr)
2905, 1754, 1536, 1515, 1441, 1429, 1384, 1356, 1238, 1141, 1124, 1100, 1063, 1011, 916, 878, 861, 828, 786, 750, 724, 675, 641, 558 cm$^{-1}$

TOF-MS; MALDI
Positive M$^+$749 (corresponding to $C_{47}H_{47}N_2O_4S$)
Negative M$^-$390 (corresponding to $C_{14}H_{16}F_5O_5S$)

Synthesis Example 1-4

Synthesis of 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium 2-hydroxy-1,1,3,3,3-pentafluoropropanesulfonate, designated Dye-D

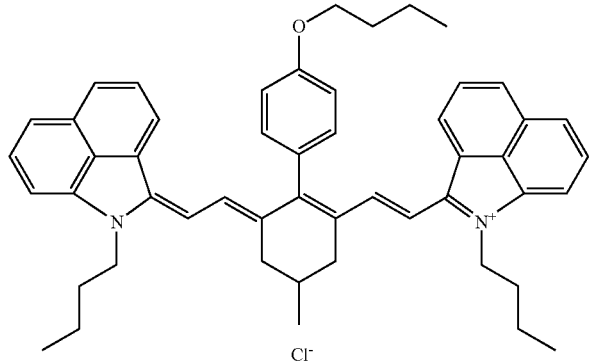
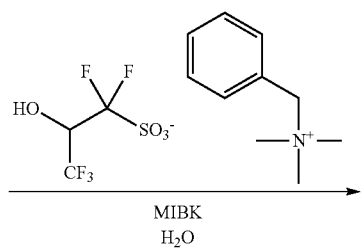
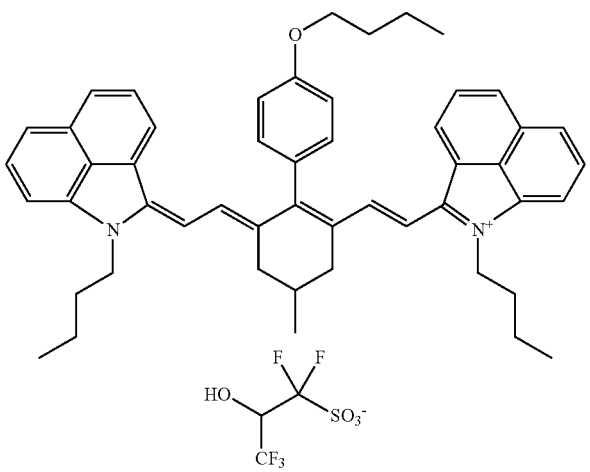

A mixture of 0.75 g (1 mmol) of 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium chloride, 0.57 g (1.5 mmol) of benzyltrimethylammonium 2-hydroxy-1,1,3,3,3-pentafluoropropanesulfonate, 15 g of water, and 15 g of methyl isobutyl ketone was stirred for 8 hours at room temperature, whereupon the organic layer was taken out. The organic layer was combined with 0.19 g (0.5 mmol) of benzyltrimethylammonium 2-hydroxy-1,1,3,3,3-pentafluoropropanesulfonate and 15 g of water and stirred for 7 hours, whereupon the organic layer was taken out. The organic layer was washed with water and concentrated in vacuum. Diisopropyl ether was added to the residue for recrystallization. The crystal was collected and dried in vacuum, obtaining the target compound, 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium 2-hydroxy-1,1,3,3,3-pentafluoropropanesulfonate. Brown crystal, 0.92 g, yield 98%.

Figure 7:
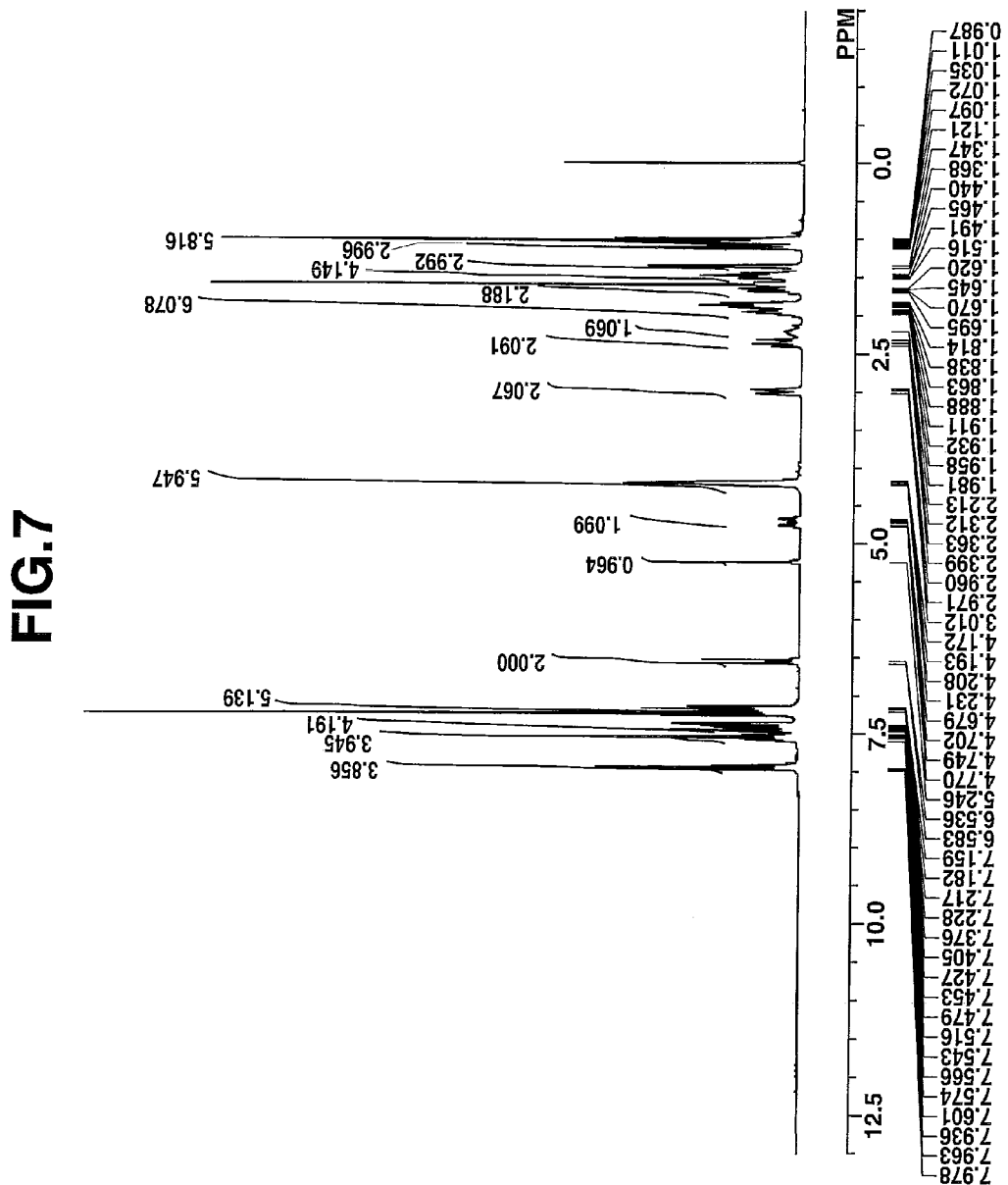
FIGS. 7 and 8 are diagrams of $^1$H-NMR and $^{19}$F-NMR/CDCl$_3$ spectra of Dye-D in Synthesis Example 1-4, respectively.
Figure 8:
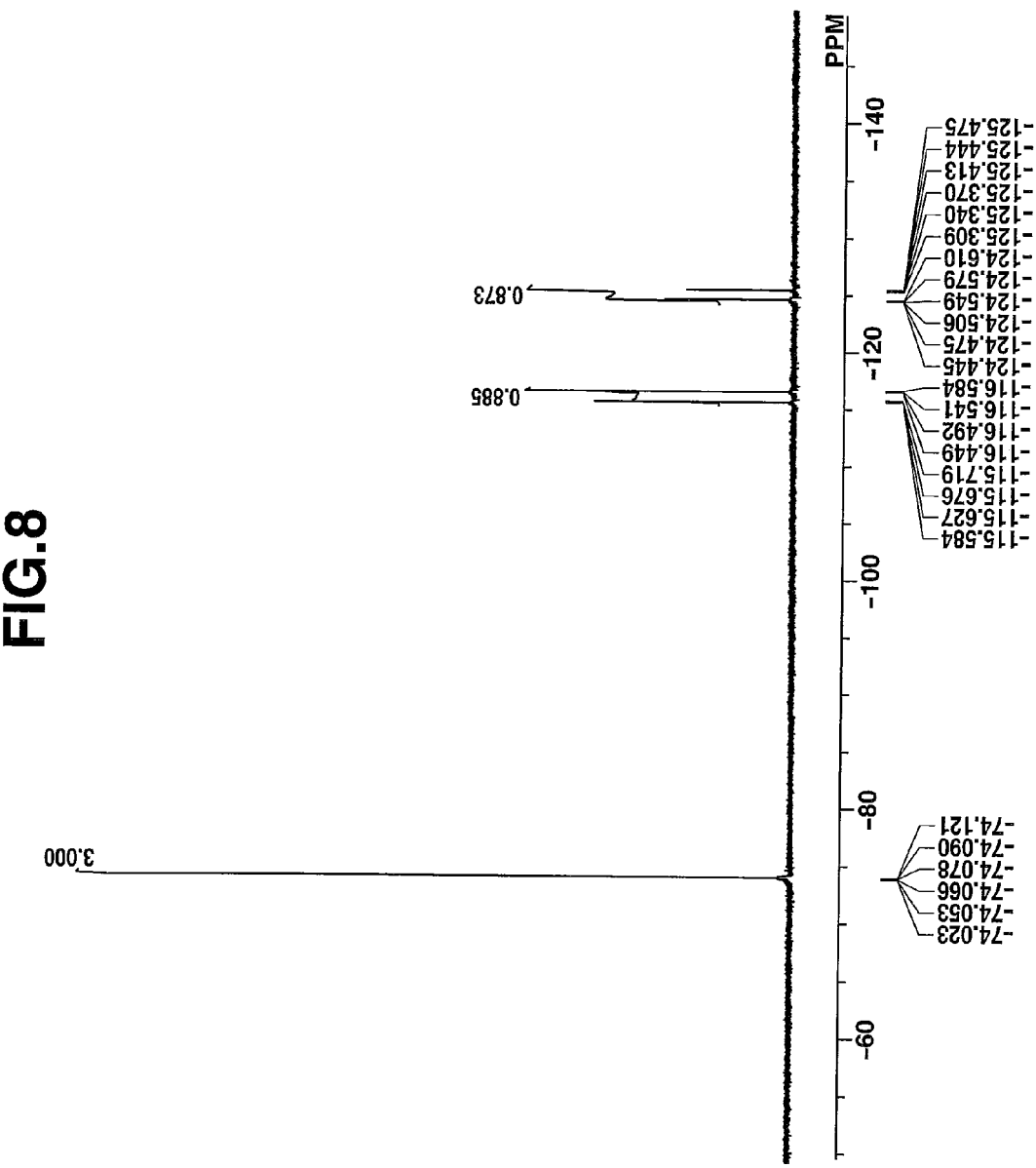

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 7 and 8. It is noted that in $^1$H-NMR analysis, a trace of water was observed.

IR (KBr)

2954, 2871, 1579, 1537, 1508, 1489, 1457, 1441, 1426, 1389, 1365, 1235, 1226, 1198, 1174, 1125, 1064, 1035, 983, 951, 910, 858, 818, 801, 762, 735, 688, 637, 554

TOF-MS; MALDI

Positive M$^+$711 (corresponding to $C_{51}H_{55}N_2O$)

Negative M$^-$228 (corresponding to $C_3H_2F_5O_4S$)

Synthesis Example 1-5

Synthesis of 1-butyl-2-(2-{3-[2-(1-butyl-1H-benzo[cd]-indol-2-ylidene)ethylidene]-2-(4-butoxyphenyl)cyclohex-5-methyl-1-en-1-yl}ethenyl)-benzo[cd]indol-1-ium 2-(1-adamantanecarbonyloxy)-1,1,3,3,3-pentafluoropropane-sulfonate, designated Dye-E

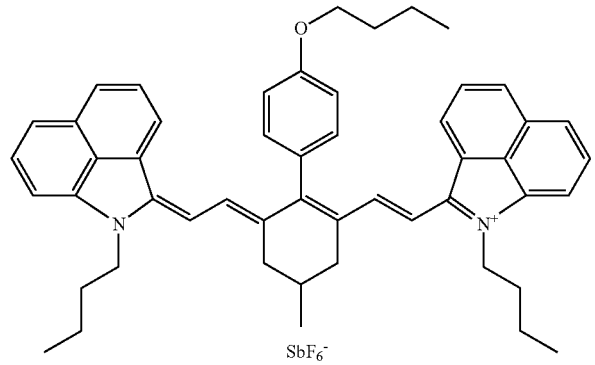
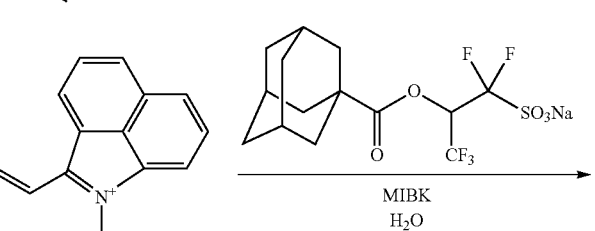
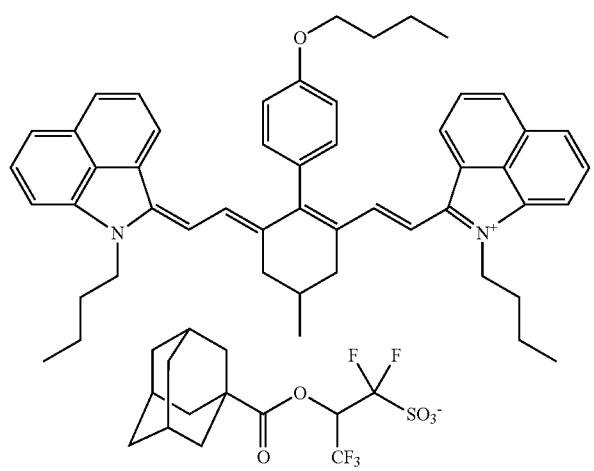

A mixture of 9.5 g (10 mmol) of 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium hexafluoroantimonate, 24.2 g (15 mmol) of sodium 2-(1-adamantanecarbonyloxy)-1,1,3,3,3-pentafluoropropane-sulfonate aqueous solution, 250 g of water, and 250 g of methyl isobutyl ketone was stirred overnight at room temperature, whereupon the organic layer was taken out. The organic layer was combined with 8.1 g (5 mmol) of sodium 2-(1-adamantanecarbonyloxy)-1,1,3,3,3-pentafluoropropane-sulfonate aqueous solution and 250 g of water and stirred for 9 hours, whereupon the organic layer was taken out. The organic layer was washed with water and concentrated in vacuum. Diisopropyl ether was added to the residue for recrystallization. The crystal was collected and dried in vacuum, obtaining the target compound, 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium 2-(1-adamantanecarbonyloxy)-1,1,3,3,3-pentafluoropropane-sulfonate. Brown crystal, 11.3 g, yield 99%.

Figure 9:
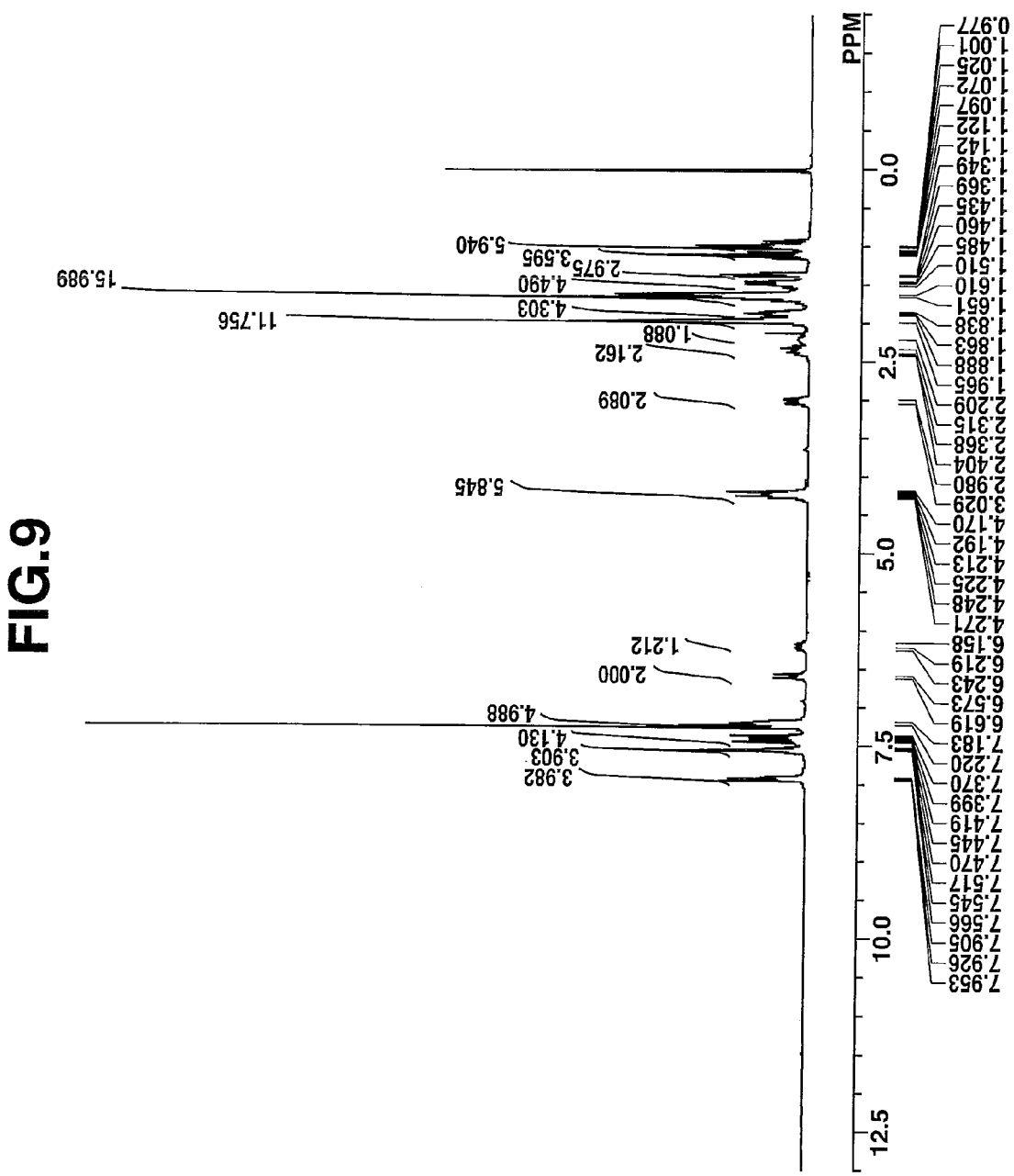
FIGS. 9 and 10 are diagrams of $^1$H-NMR and $^{19}$F-NMR/CDCl$_3$ spectra of Dye-E in Synthesis Example 1-5, respectively.
Figure 10:
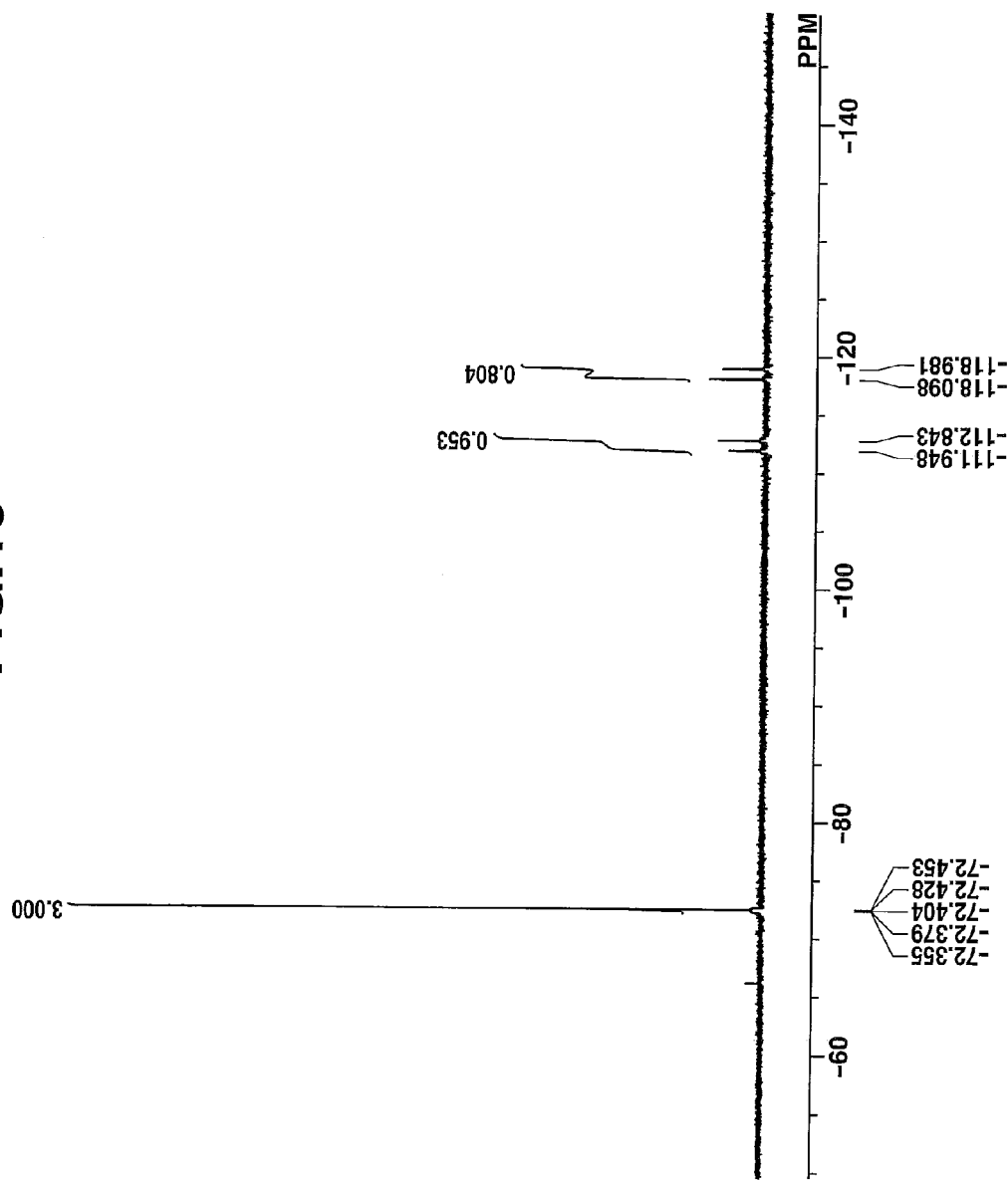

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 9 and 10. It is noted that in $^1$H-NMR analysis, traces of residual solvents (diisopropyl ether, methyl isobutyl ketone, water) were observed.

IR (KBr)
 2906, 1753, 1578, 1540, 1508, 1489, 1456, 1425, 1387, 1365, 1335, 1266, 1199, 1175, 1127, 1073, 1034, 982, 950, 907, 860, 818, 801, 763, 734, 685, 639, 553 cm$^{-1}$

TOF-MS; MALDI
 Positive M$^+$711 (corresponding to C$_{51}$H$_{55}$N$_2$O)
 Negative M$^-$390 (corresponding to C$_{14}$H$_{16}$F$_5$O$_5$S)

Synthesis Example 1-6

Synthesis of 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium 1,1,3,3,3-pentafluoro-2-(pivaloyloxy)propanesulfonate, designated Dye-F

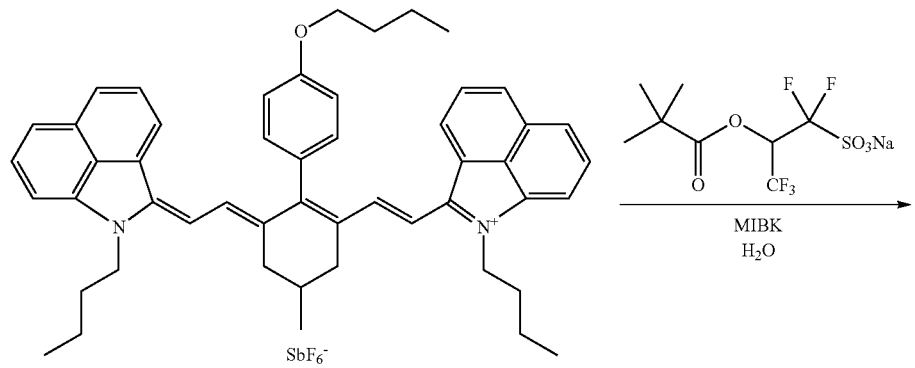

A mixture of 4.7 g (5 mmol) of 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium hexafluoroantimonate, 15.3 g (7.5 mmol) of sodium 1,1,3,3,3-pentafluoro-2-(pivaloyloxy)propanesulfonate aqueous solution, 100 g of water, and 100 g of methyl isobutyl ketone was stirred overnight at room temperature, whereupon the organic layer was taken out. The organic layer was combined with 5.1 g (2.5 mmol) of sodium 1,1,3,3,3-pentafluoro-2-(pivaloyloxy)propanesulfonate aqueous solution and 100 g of water and stirred for 5 hours, whereupon the organic layer was taken out. The organic layer was washed with water and concentrated in vacuum. Diisopropyl ether was added to the residue for recrystallization.

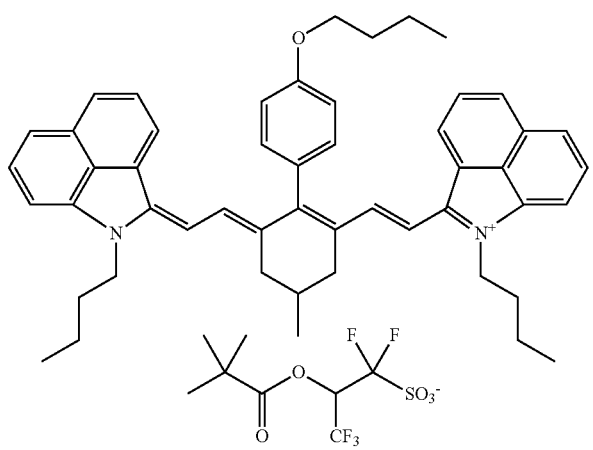

The crystal was collected and dried in vacuum, obtaining the target compound, 1-butyl-2-(2-{3-[2-(1-butyl-1H-benzo[cd]indol-2-ylidene)ethylidene]-2-(4-butoxyphenyl)cyclohex-5-methyl-1-en-1-yl}ethenyl)-benzo[cd]indol-1-ium 1,1,3,3,3-pentafluoro-2-(pivaloyloxy)-propanesulfonate. Brown crystal, 4.6 g, yield 90%.

Figure 11:
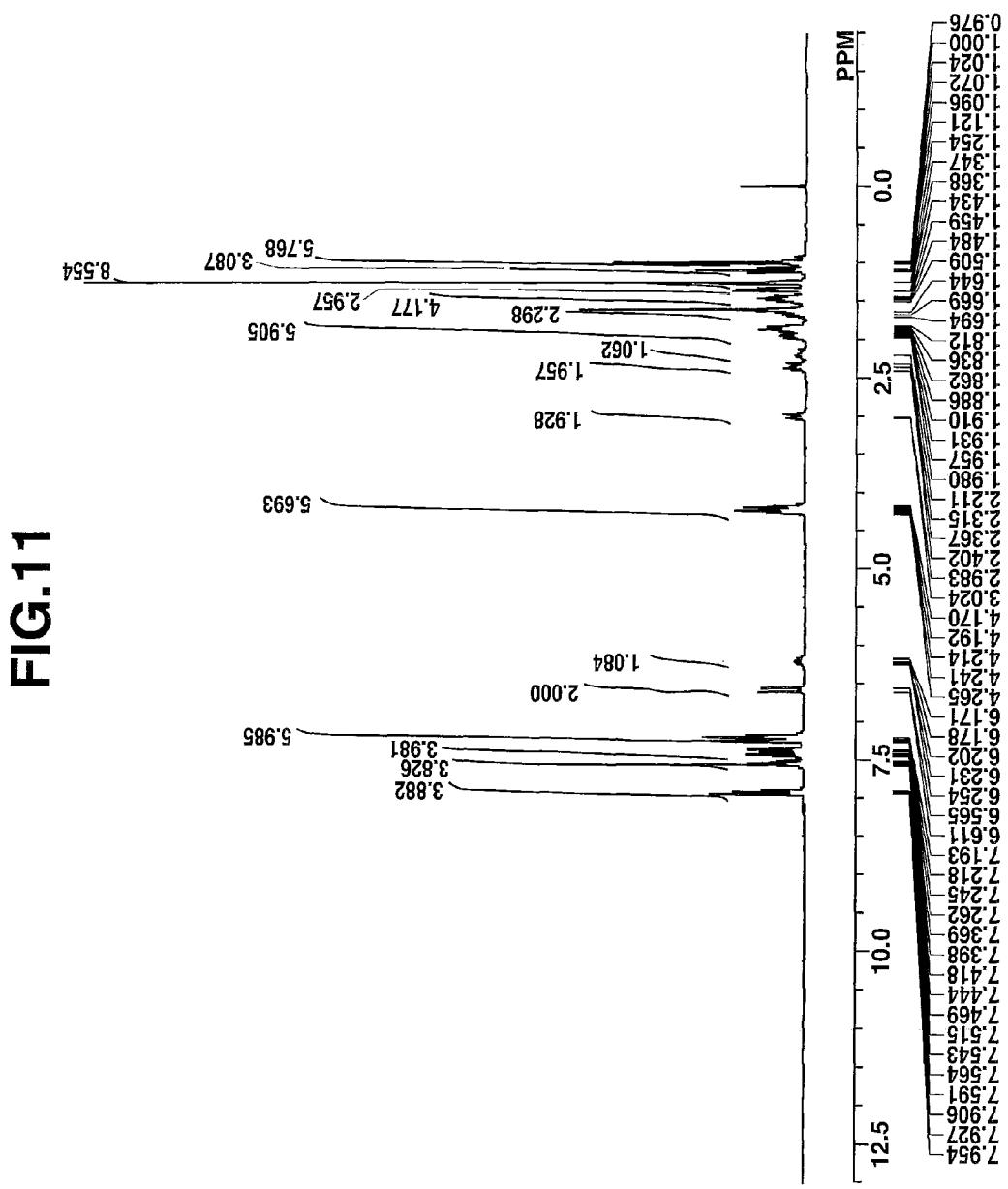
FIGS. 11 and 12 are diagrams of $^1$H-NMR and $^{19}$F-NMR/CDCl$_3$ spectra of Dye-F in Synthesis Example 1-6, respectively.
Figure 12:
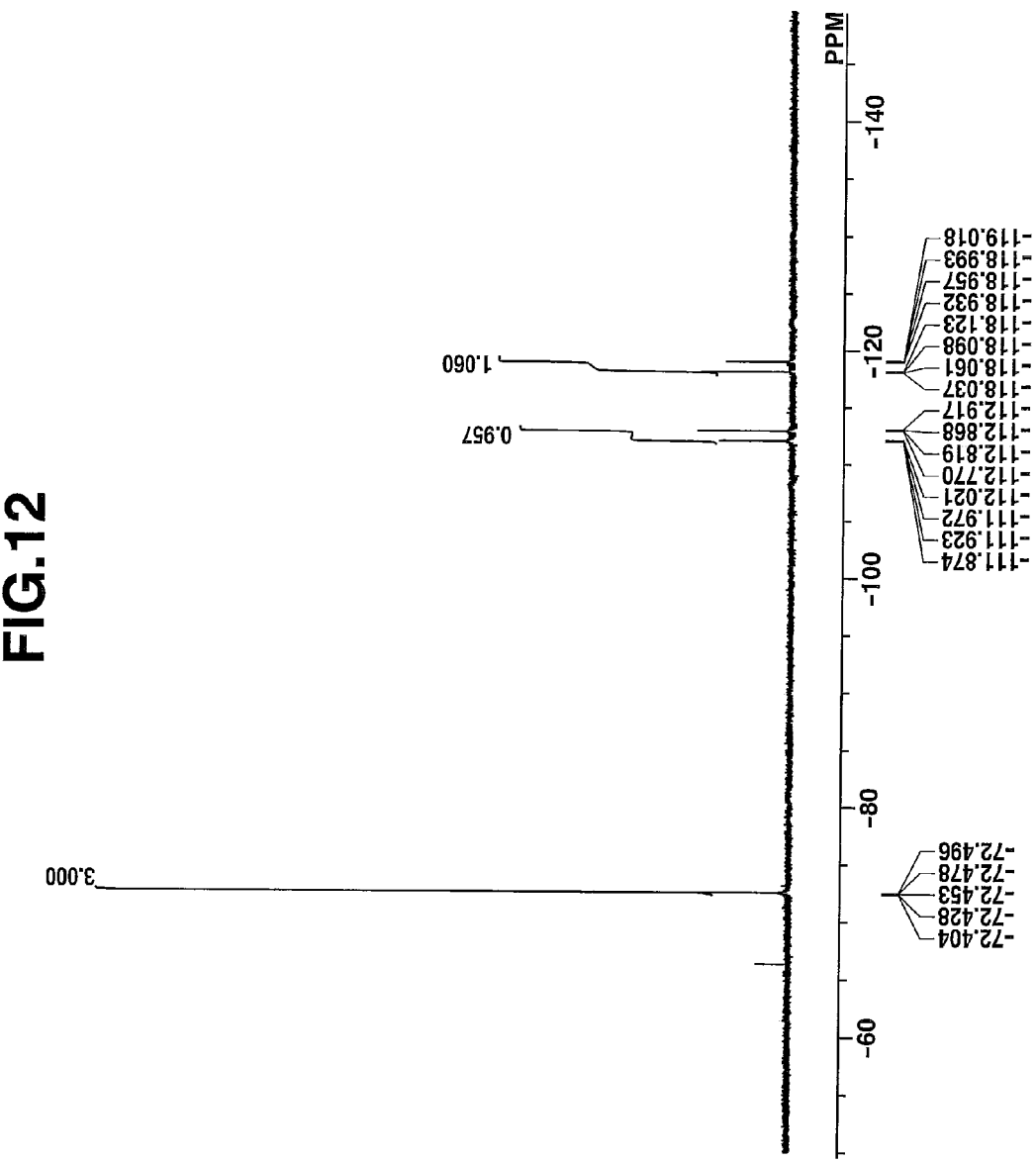

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 11 and 12. It is noted that in $^1$H-NMR analysis, a trace of water was observed.

IR (KBr)

2958, 2872, 1758, 1579, 1539, 1508, 1489, 1458, 1425, 1387, 1363, 1336, 1318, 1226, 1199, 1176, 1125, 1076, 1036, 983, 950, 911, 861, 819, 802, 765, 736, 687, 640, 554 cm$^{-1}$

TOF-MS; MALDI

Positive M$^+$711 (corresponding to $C_{51}H_{55}N_2O$)

Negative M$^-$312 (corresponding to $C_8F_5O_5S$)

Synthesis Example 1-7

Synthesis of 1-butyl-2-[7-(1-butyl-1H-benzo[cd]indol-2-ylidene)hepta-1,3,5-trien-1-yl]-benzo[cd]indol-1-ium 1,1,3,3,3-pentafluoro-2-(pivaloyloxy)propanesulfonate, designated Dye-G

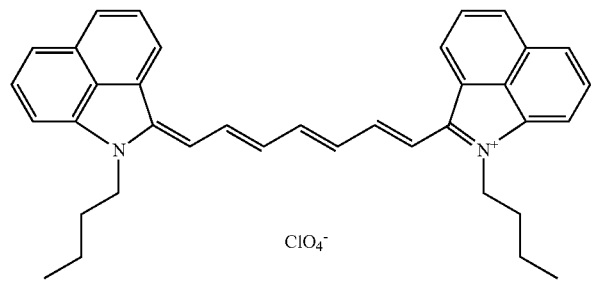

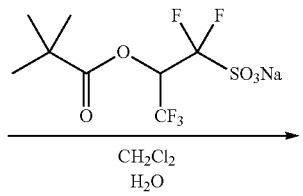

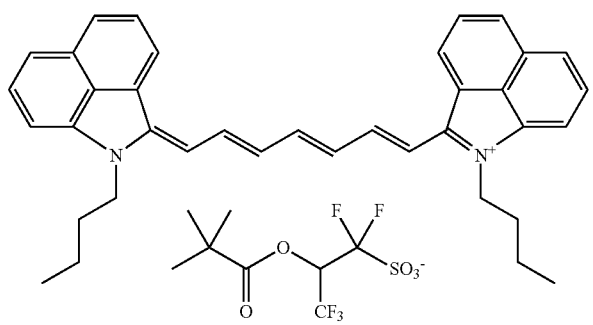

A mixture of 1.2 g (2 mmol) of 1-butyl-2-[7-(1-butyl-1H-benzo[cd]indol-2-ylidene)hepta-1,3,5-trien-1-yl]-benzo[cd]indol-1-ium perchlorate, 6.1 g (3 mmol) of sodium 1,1,3,3,3-pentafluoro-2-(pivaloyloxy)propanesulfonate aqueous solution, 10 g of water, and 25 g of methylene chloride was stirred overnight at room temperature, whereupon the organic layer was taken out. The organic layer was washed with water, concentrated in vacuum, combined with methyl isobutyl ketone, and concentrated in vacuum again. Diisopropyl ether was added to the residue for recrystallization. The crystal was collected and dried in vacuum, obtaining the target compound, 1-butyl-2-[7-(1-butyl-1H-benzo[cd]indol-2-ylidene)-hepta-1,3,5-trien-1-yl]-benzo[cd]indol-1-ium 1,1,3,3,3-pentafluoro-2-(pivaloyloxy)propanesulfonate. Brown crystal, 2.0 g, yield 93%.

Figure 13:
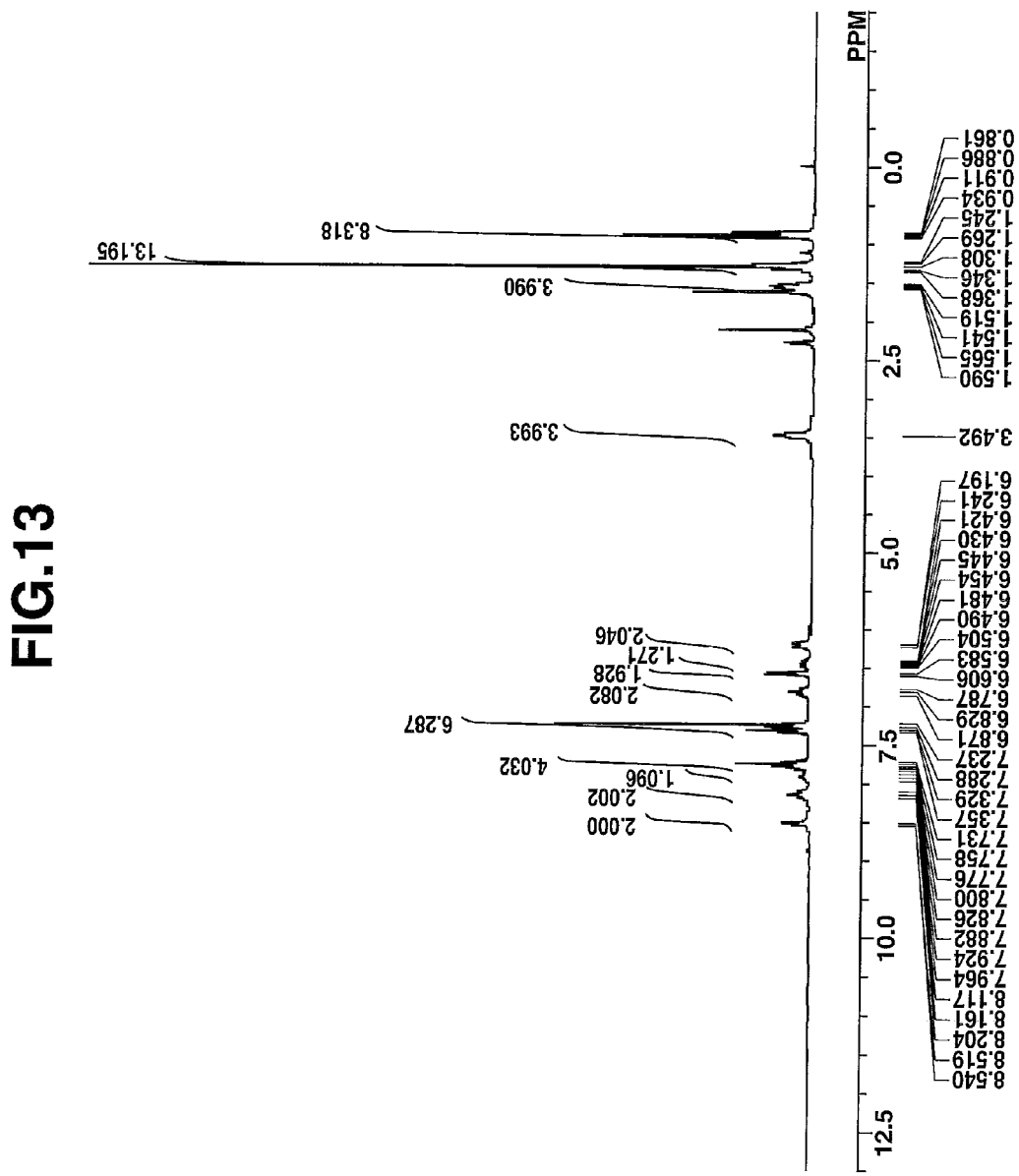
FIGS. 13 and 14 are diagrams of $^1$H-NMR and $^{19}$F-NMR/CDCl$_3$ spectra of Dye-G in Synthesis Example 1-7, respectively.
Figure 14:
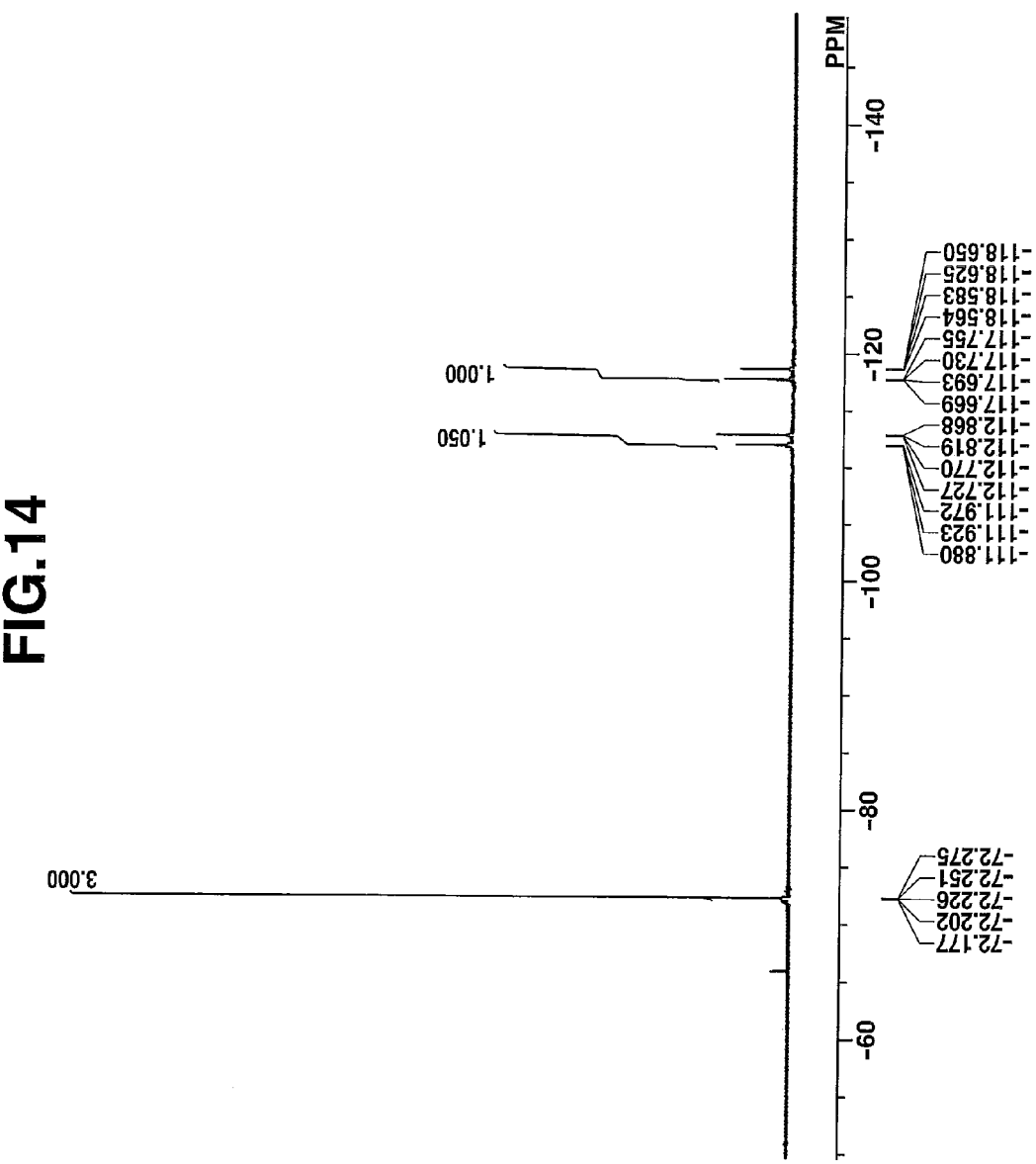

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 13 and 14. It is noted that in $^1$H-NMR analysis, traces of residual solvents (methyl isobutyl ketone, water) was observed.

IR (KBr)
2959, 2872, 1758, 1580, 1510, 1490, 1444, 1417, 1397, 1367, 1343, 1303, 1268, 1251, 1230, 1191, 1121, 1062, 1034, 950, 912, 819, 802, 767, 699, 640 cm$^{-1}$

TOF-MS; MALDI
Positive M$^+$509 (corresponding to C$_{37}$H$_{37}$N$_2$)
Negative M$^-$312 (corresponding to C$_8$F$_5$O$_5$S)

Synthesis Example 1-8

Synthesis of 1-butyl-2-(2-{3-[2-(1-butyl-1H-benzo[cd]indol-2-ylidene)ethylidene]-2-(N,N-diphenylamino)cyclopent-1-en-1-yl)ethenyl)-benzo[cd]indol-1-ium 1,1,3,3,3-pentafluoro-2-(pivaloyloxy)propanesulfonate, designated Dye-H

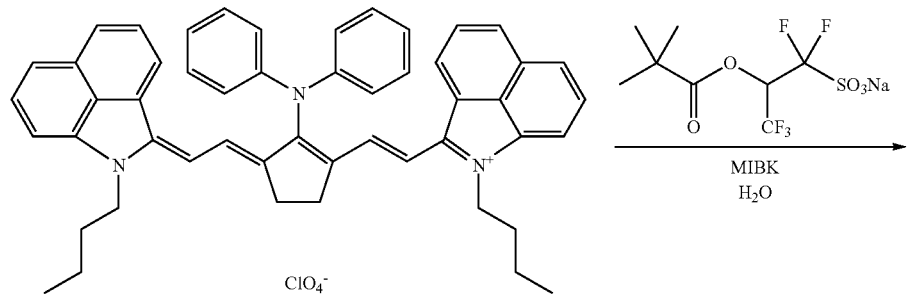

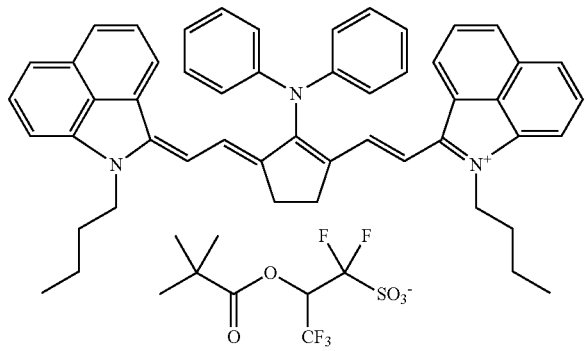

A mixture of 0.80 g (1 mmol) of 1-butyl-2-(2-{3-[2-(1-butyl-1H-benzo[cd]indol-2-ylidene)ethylidene]-2-(N,N-diphenylamino)cyclopent-1-en-1-yl)ethenyl)-benzo[cd]indol-1-ium perchlorate, 3.1 g (1.5 mmol) of sodium 1,1,3,3,3-pentafluoro-2-(pivaloyloxy)propanesulfonate aqueous solution, 16 g of water, and 16 g of methyl isobutyl ketone was stirred overnight at room temperature, whereupon the organic layer was taken out. The organic layer was washed with water and concentrated in vacuum. Diisopropyl ether was added to the residue for recrystallization. The crystal was collected and dried in vacuum, obtaining the target compound, 1-butyl-2-(2-{3-[2-(1-butyl-1H-benzo[cd]indol-2-ylidene)ethylidene]-2-(N,N-diphenylamino)cyclopent-1-en-1-yl)ethenyl)-benzo[cd]-indol-1-ium 1,1,3,3,3-pentafluoro-2-(pivaloyloxy)propane-sulfonate. Brown crystal, 0.88 g, yield 86%.

Figure 15:
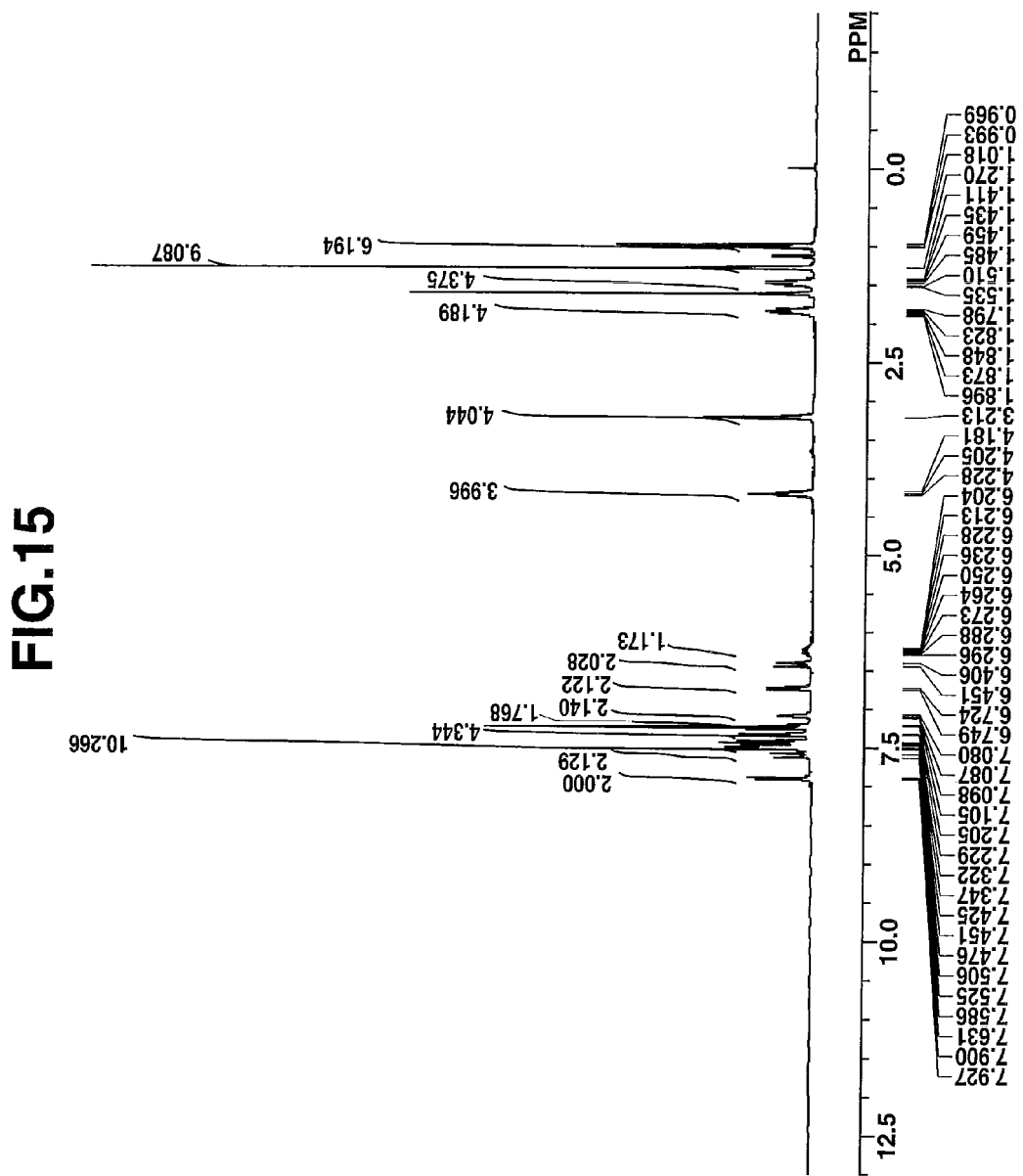
FIGS. 15 and 16 are diagrams of $^1$H-NMR and $^{19}$F-NMR/CDCl$_3$ spectra of Dye-H in Synthesis Example 1-8, respectively.
Figure 16:
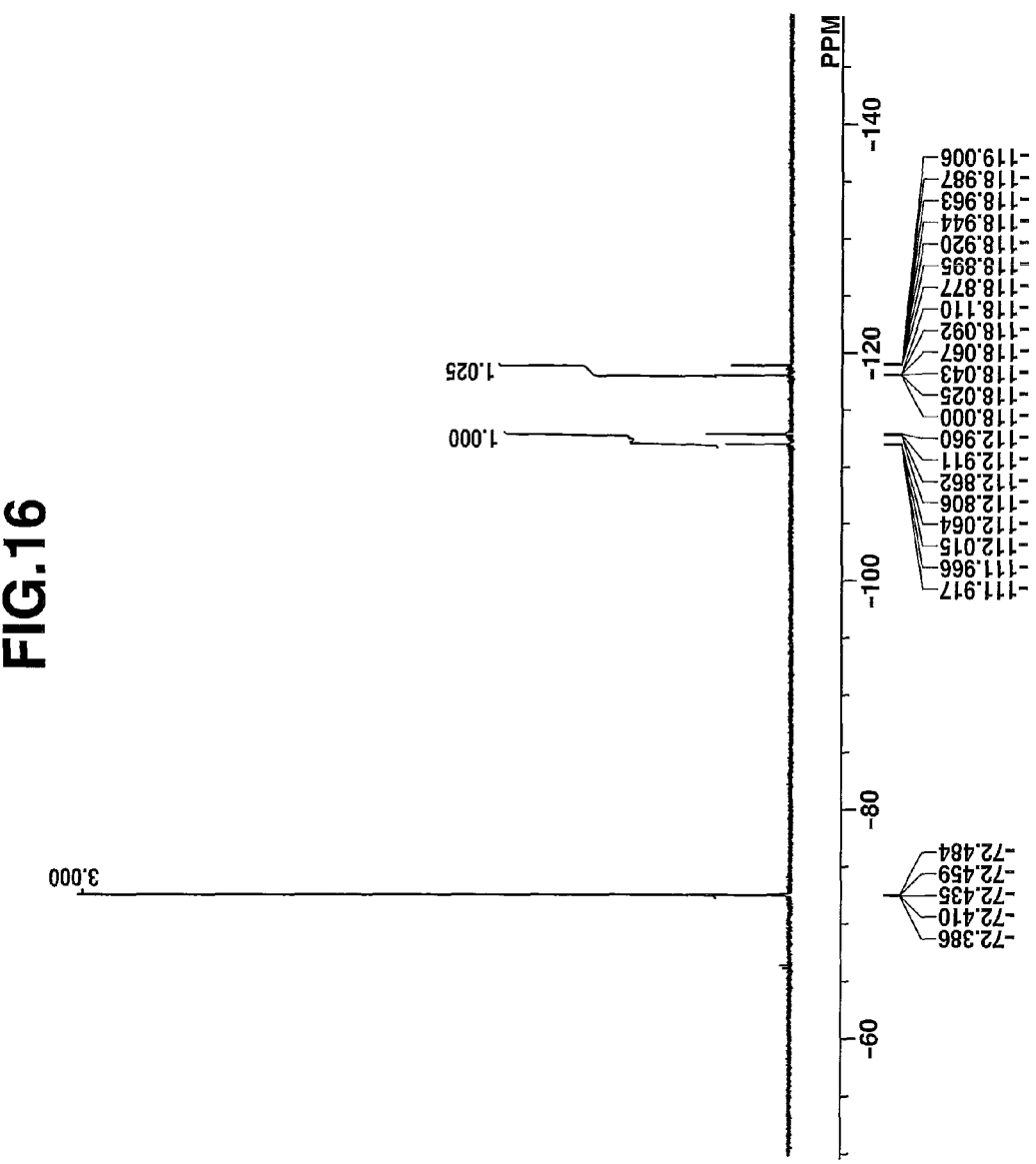

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 15 and 16. It is noted that in $^1$H-NMR analysis, traces of residual solvents (diisopropyl ether, water) were observed.

IR (KBr)

3474, 1758, 1581, 1546, 1507, 1489, 1455, 1434, 1377, 1334, 1253, 1227, 1193, 1164, 1133, 1075, 1036, 891, 831, 801, 763, 696, 674, 640 cm$^{-1}$

TOF-MS; MALDI

Positive M$^+$702 (corresponding to C$_{51}$H$_{48}$N$_3$)

Negative M$^-$312 (corresponding to C$_3$F$_5$O$_5$S)

Synthesis Example 1-9

Synthesis of 1-butyl-2-(2-{3-[2-(1-butyl-1H-benzo[cd]indol-2-ylidene)ethylidene]-2-phenylcyclohex-1-en-1-yl)ethenyl)-benzo[cd]indol-1-ium 1,1,3,3,3-pentafluoro-2-(pivaloyloxy)-propanesulfonate, designated Dye-I

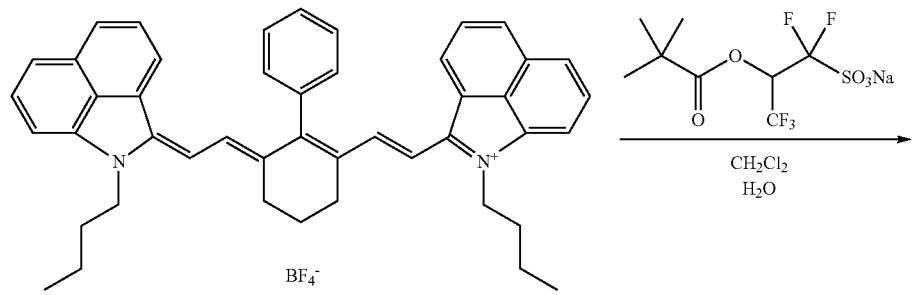

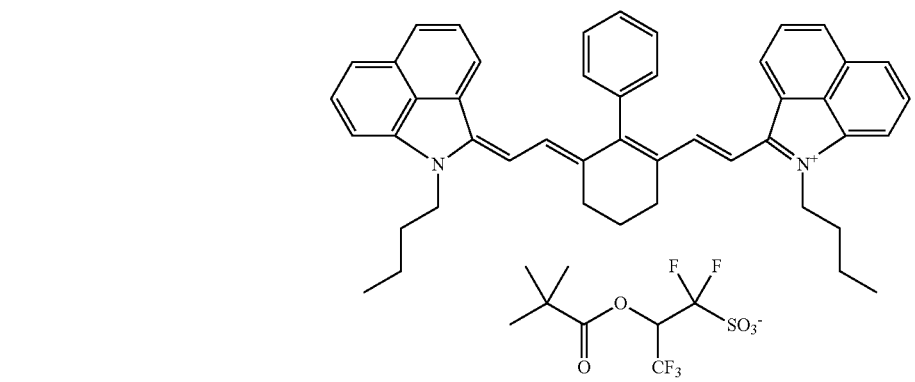

A mixture of 2.1 g (3 mmol) of 1-butyl-2-(2-{3-[2-(1-butyl-1H-benzo[cd]indol-2-ylidene)ethylidene]-2-phenyl-cyclohex-1-en-1-yl)ethenyl)-benzo[cd]indol-1-ium tetrafluoroborate, 9.1 g (4.5 mmol) of sodium 1,1,3,3,3-pentafluoro-2-(pivaloyloxy)propanesulfonate aqueous solution, 20 g of water, and 50 g of methylene chloride was stirred overnight at room temperature, whereupon the organic layer was taken out. The organic layer was washed with water, concentrated in vacuum, combined with methyl isobutyl ketone, and concentrated in vacuum again. Diisopropyl ether was added to the residue for recrystallization. The crystal was collected and dried in vacuum, obtaining the target compound, 1-butyl-2-(2-{3-[2-(1-butyl-1H-benzo[cd]indol-2-ylidene)-ethylidene]-2-phenylcyclohex-1-en-1-yl)ethenyl)-benzo[cd]indol-1-ium 1,1,3,3,3-pentafluoro-2-(pivaloyloxy)-propanesulfonate. Brown crystal, 2.6 g, yield 93%.

Figure 17:
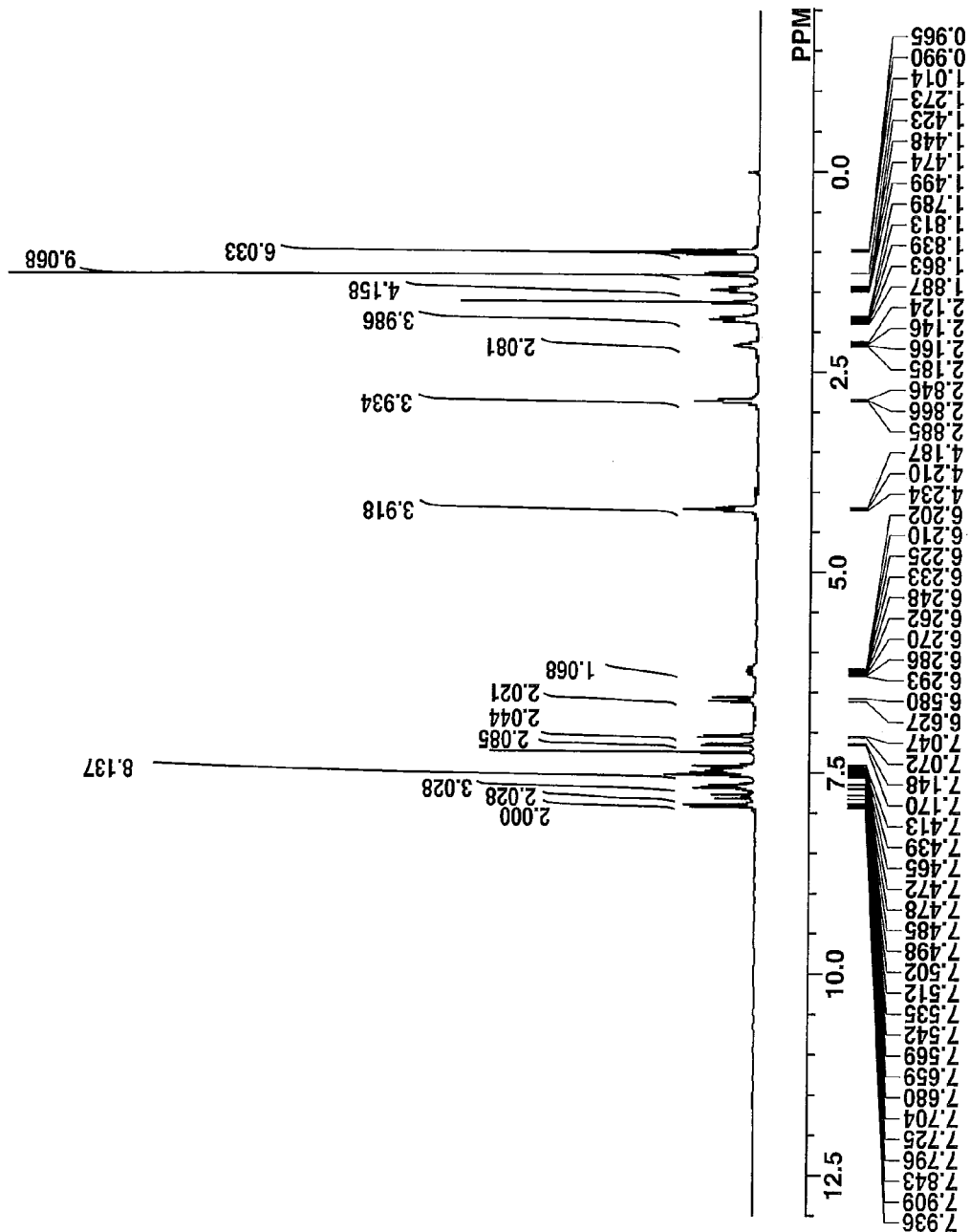
FIGS. 17 and 18 are diagrams of $^1$H-NMR and $^{19}$F-NMR/CDCl$_3$ spectra of Dye-I in Synthesis Example 1-9, respectively.
Figure 18:
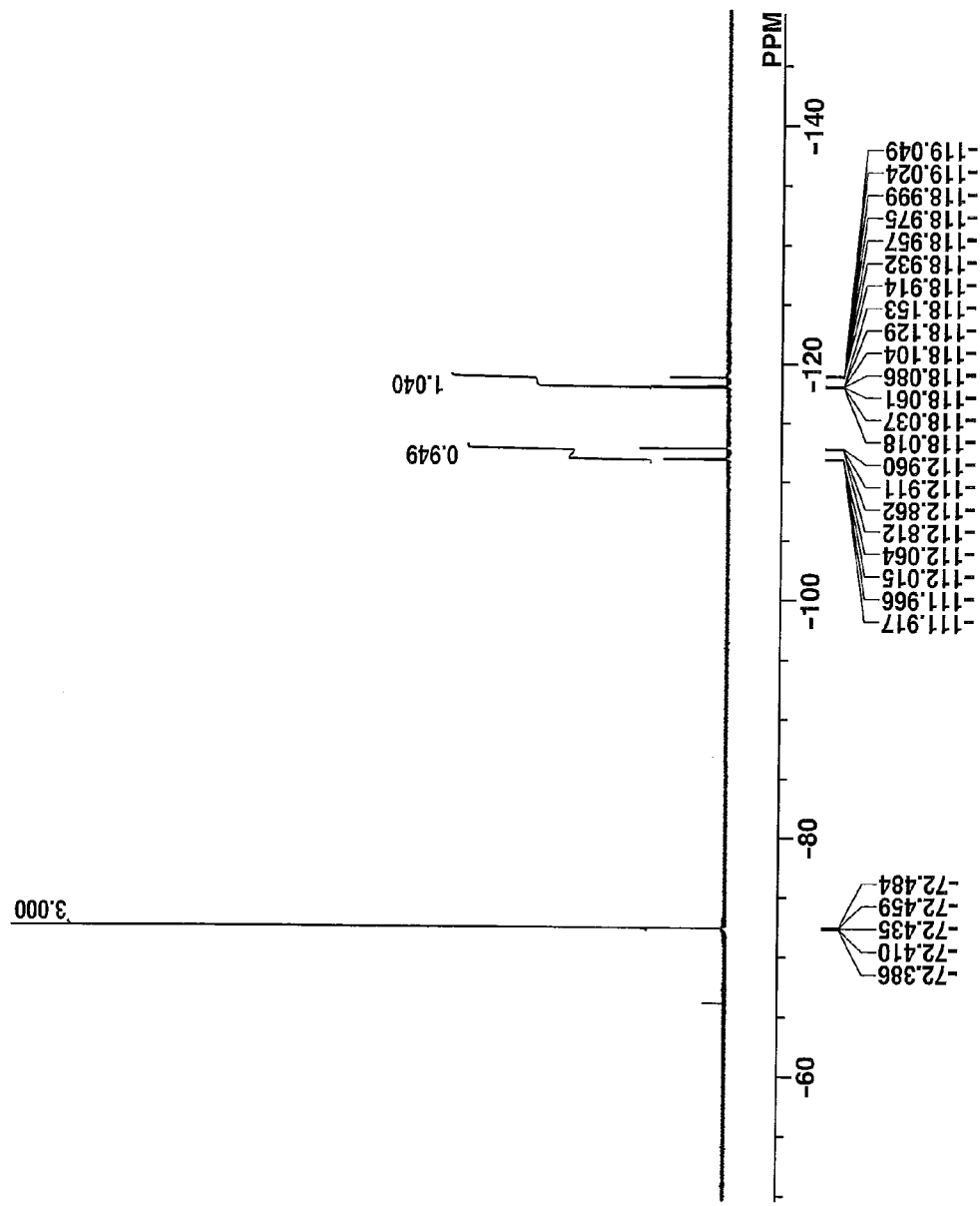

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 17 and 18. It is noted that in $^1$H-NMR analysis, a trace of water was observed.

IR (KBr)

3441, 2933, 1758, 1633, 1578, 1540, 1490, 1443, 1428, 1388, 1361, 1336, 1252, 1228, 1214, 1126, 1081, 1063, 1034, 952, 910, 859, 819, 801, 762, 709, 686, 640, 545 cm$^{-1}$

TOF-MS; MALDI

Positive M$^+$625 (corresponding to $C_{46}H_{45}N_2$)

Negative M$^-$312 (corresponding to $C_8F_5O_5S$)

Synthesis Example 1-10

Synthesis of 1-butyl-2-(2-{3-[2-(1-butyl-1H-benzo[cd]indol-2-ylidene)ethylidene]-2-(4-butoxyphenyl)cyclohex-4-methyl-1-en-1-yl}ethenyl)-benzo[cd]indol-1-ium 1,1,3,3,3-pentafluoro-2-(pivaloyloxy)propanesulfonate, designated Dye-R

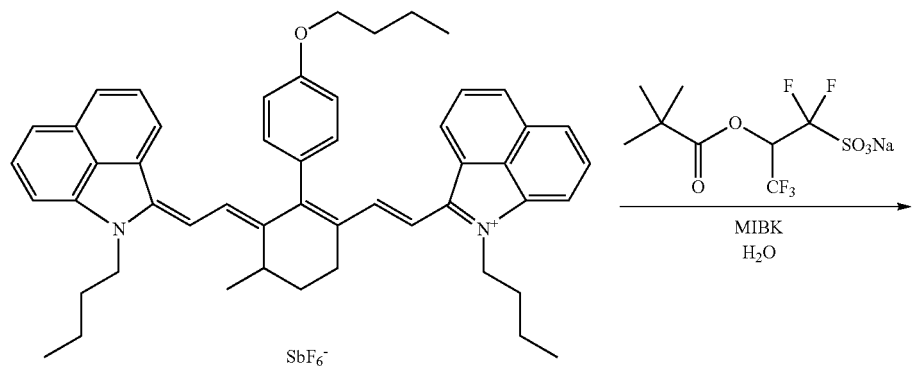

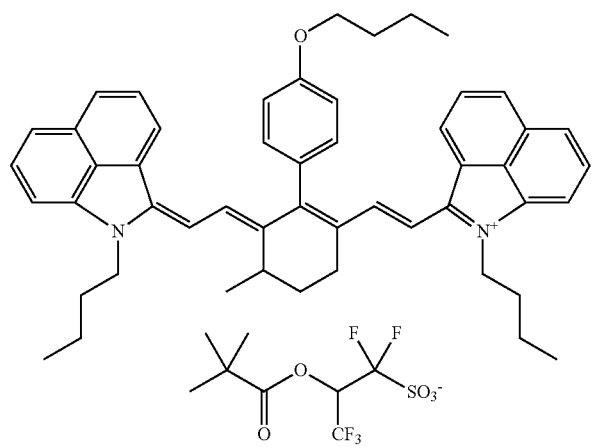

A mixture of 1.1 g (2 mmol) of 1-butyl-2-(2-{3-[2-(1-butyl-1H-benzo[cd]indol-2-ylidene)ethylidene]-2-(4-butoxyphenyl)cyclohex-4-methyl-1-en-1-yl}ethenyl)-benzo[cd]indol-1-ium tetrafluoroborate, 6.1 g (3 mmol) of sodium 1,1,3,3,3-pentafluoro-2-(pivaloyloxy)propanesulfonate aqueous solution, 15 g of water, and 20 g of methyl isobutyl ketone was stirred overnight at room temperature, whereupon the organic layer was taken out. The organic layer was washed with water and concentrated in vacuum. Diisopropyl ether was added to the residue for recrystallization. The crystal was collected and dried in vacuum, obtaining the target compound, 1-butyl-2-(2-{3-[2-(1-butyl-1H-benzo[cd]indol-2-ylidene)ethylidene]-2-(4-butoxyphenyl)cyclohex-4-methyl-1-en-1-yl}ethenyl)-benzo[cd]indol-1-ium 1,1,3,3,3-pentafluoro-2-(pivaloyloxy)-propanesulfonate. Brown crystal, 1.2 g, yield 59%.

Figure 19:
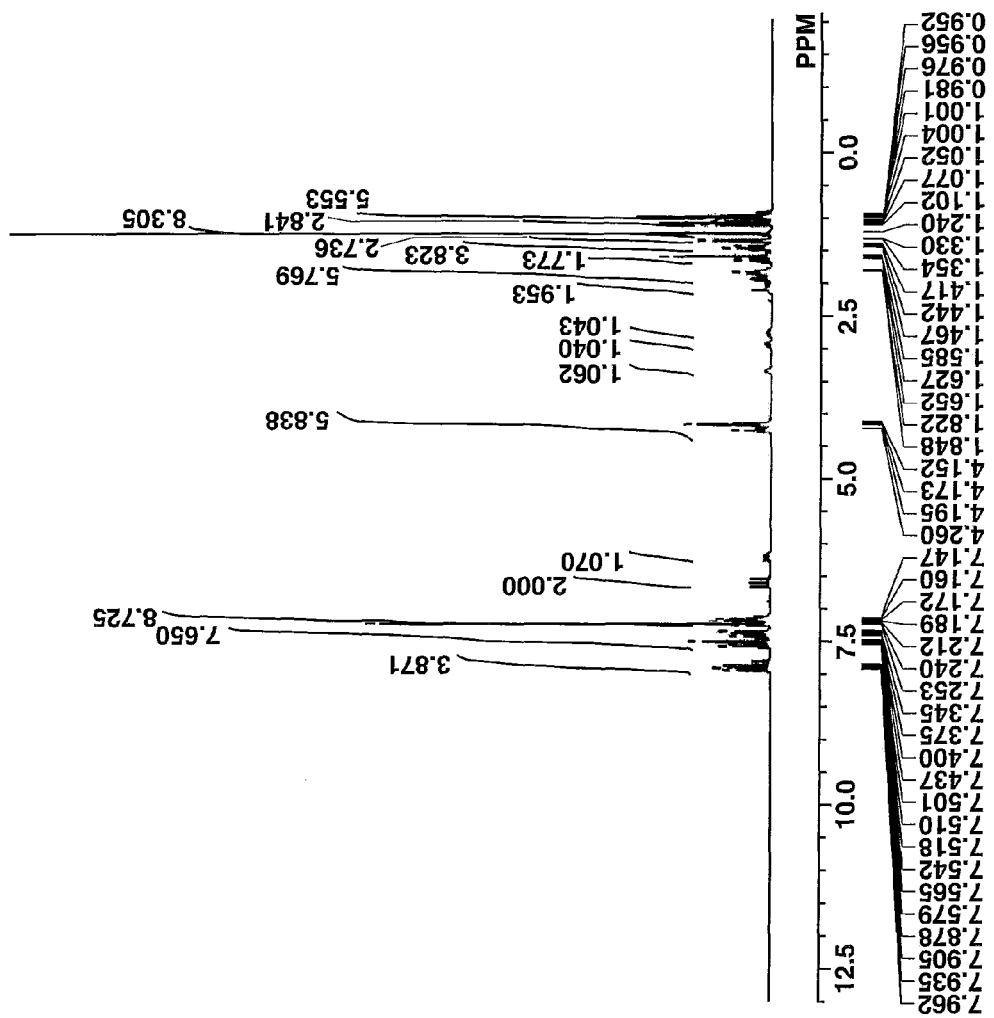
FIGS. 19 and 20 are diagrams of $^1$H-NMR and $^{19}$F-NMR/CDCl$_3$ spectra of Dye-R in Synthesis Example 1-10, respectively.
Figure 20:
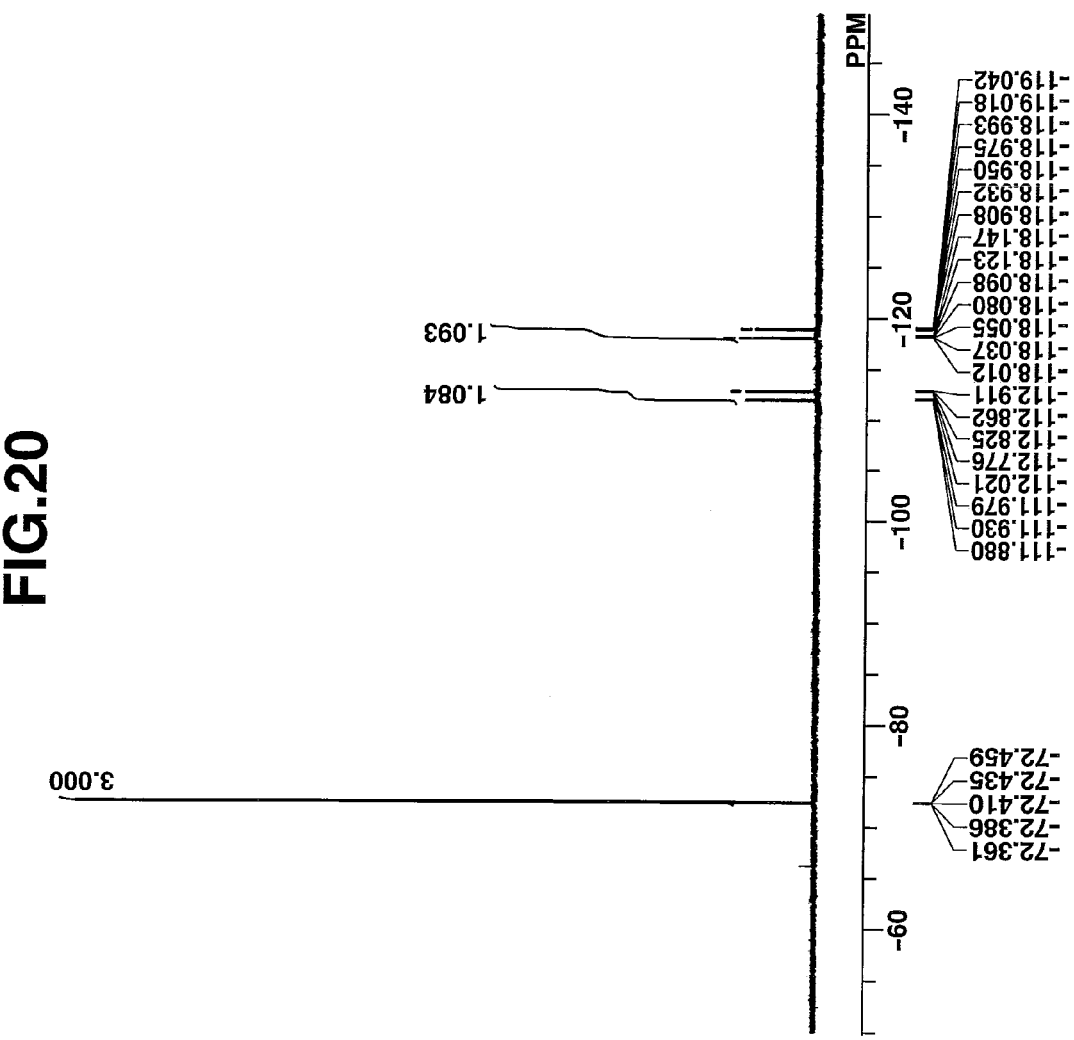

The compound was analyzed by infrared absorption and nuclear magnetic resonance spectroscopies. The spectral data are shown below. The NMR spectra ($^1$H-NMR and $^{19}$F-NMR/CDCl$_3$) are shown in FIGS. 19 and 20. It is noted that in $^1$H-NMR analysis, a trace of water was observed.

IR (KBr)

3437, 2959, 2873, 1759, 1634, 1579, 1540, 1509, 1490, 1458, 1437, 1390, 1363, 1337, 1253, 1231, 1191, 1135, 1076, 1033, 945, 914, 898, 853, 819, 802, 765, 732, 687, 641, 551 cm$^{-1}$

TOF-MS; MALDI

Positive M$^+$711 (corresponding to C$_{51}$H$_{55}$N$_2$O)

Negative M$^-$312 (corresponding to C$_3$F$_5$O$_5$S)

NIR absorbing dyes (Dye-J to Q) used in Comparative Examples were purchased from chemical suppliers or synthesized by the same procedure as above. These dyes have the structure shown below.

Dye-J
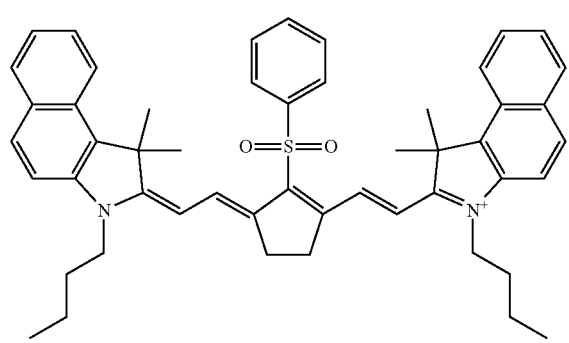
SbF$_6^-$
Dye-K
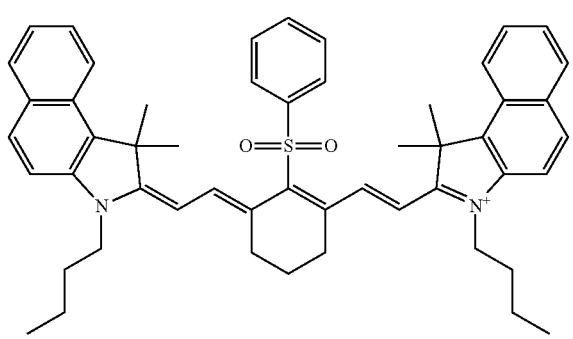
I$^-$
Dye-L
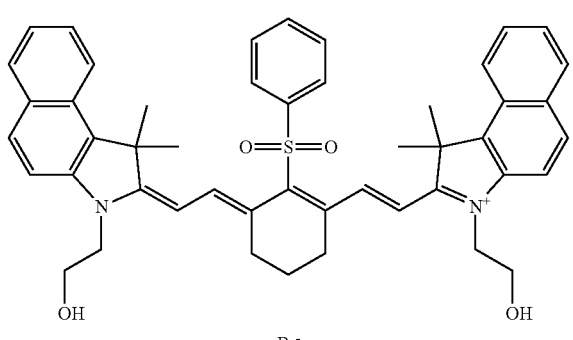
Br$^-$
Dye-M
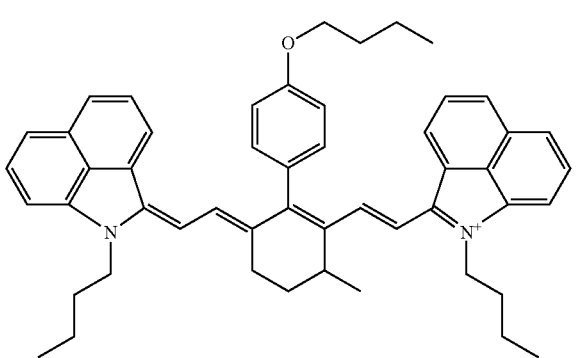
Cl$^-$
Dye-N
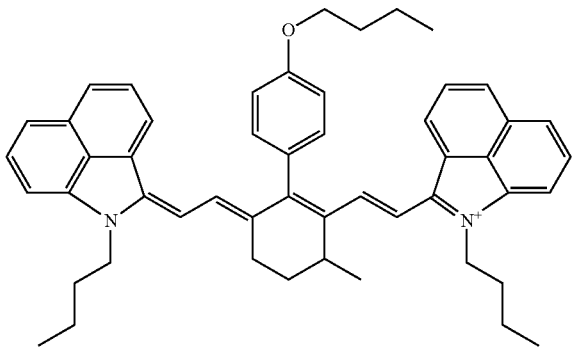
NO$_3^-$
Dye-O
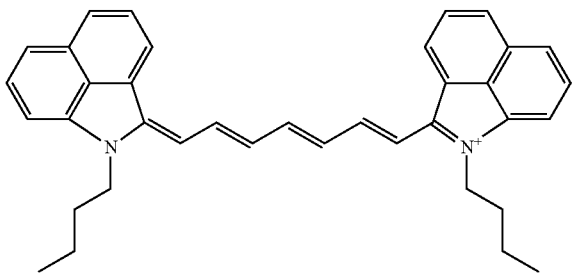
ClO$_4^-$
Dye-P
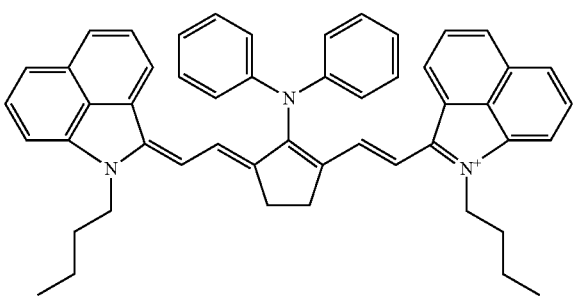
ClO$_4^-$
Dye-Q
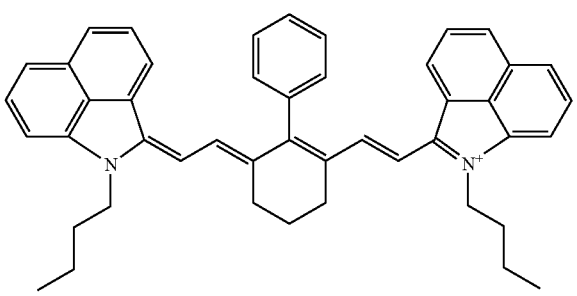
BF$_4^-$
Synthesis Example 2-1
Synthesis of Polymer 1
In a nitrogen atmosphere, a flask was charged with 13.07 g of 3,4-epoxycyclohexylmethyl methacrylate, 6.93 g of styrene, 0.920 g of dimethyl 2,2'-azobisisobutyrate (MAIB), and 20.00 g of propylene glycol monomethyl ether acetate (PG- MEA) to form a monomer solution 1. Another flask in a nitrogen atmosphere was charged with 10.00 g of PGMEA, and heated at 80° C. while stirring. Thereafter, monomer solution 1 was added dropwise to the other flask over 2 hours. The polymerization solution was continuously stirred for 6 hours while maintaining the temperature of 80° C. With the heat interrupted, the flask was allowed to cool down to room temperature. The polymerization solution was diluted with 16.67 g of PGMEA and added dropwise to a mixture of 32 g of water and 288 g of methanol being stirred, for precipitation. The polymer precipitate was collected by filtration, washed twice with 120 g of methanol, and vacuum dried at 50° C. for 20 hours, yielding 18.07 g of a polymer in white powder solid form, designated Polymer 1. The yield was 90%. Polymer 1 had a weight average molecular weight (Mw) of 14,300 and a dispersity Mw/Mn of 2.73 as measured in tetrahydrofuran by gel permeation chromatography (GPC) versus polystyrene standards. Upon $^1$H-NMR analysis, Polymer 1 had a copolymer compositional ratio of 52/48 mol %, expressed as (units derived from 3,4-epoxycyclohexylmethyl methacrylate)/(units derived from styrene).

Synthesis Example 2-2

Synthesis of Polymer 2

In a nitrogen atmosphere, a flask was charged with 11.26 g of 3,4-epoxycyclohexylmethyl methacrylate, 8.74 g of acenaphthylene, 0.793 g of MAIB, and 20.00 g of PGMEA to form a monomer solution 2. Another flask in a nitrogen atmosphere was charged with 10.00 g of PGMEA, and heated at 80° C. while stirring. Thereafter, monomer solution 2 was added dropwise to the other flask over 2 hours. The polymerization solution was continuously stirred for 6 hours while maintaining the temperature of 80° C. With the heat interrupted, the flask was allowed to cool down to room temperature. The polymerization solution was diluted with 30.00 g of PGMEA and added dropwise to 320 g of methanol being stirred, for precipitation. The polymer precipitate was collected by filtration, washed twice with 120 g of methanol, and vacuum dried at 50° C. for 20 hours, yielding 18.16 g of a polymer in white powder solid form, designated Polymer 2. The yield was 91%. Polymer 2 had a Mw of 12,300 and a dispersity Mw/Mn of 2.01 as measured in tetrahydrofuran by GPC versus polystyrene standards. Upon $^1$H-NMR analysis, Polymer 2 had a copolymer compositional ratio of 51/49 mol %, expressed as (units derived from 3,4-epoxycyclohexylmethyl methacrylate)/(units derived from acenaphthylene).

Polymer 3 is a polyhydroxystyrene purchased from Sigma Aldrich. It has a Mw of 11,000 as measured by GPC versus polystyrene standards.

Examples and Comparative Examples

Coating solutions were prepared by mixing a NIR absorbing dye, polymer, acid generator, crosslinker, surfactant FC-4430 (3M Sumitomo Co., Ltd.) in a solvent. The coating solutions were coated onto a substrate and baked at 195° C. for 60 seconds to form films. The composition of the coating solutions is reported in Table 1 together with the ease of film formation. The symbol "○" indicates good film formation and "X" indicates defective film formation.

TABLE 1

|  |  | Polymer (pbw) | NIR absorbing dye (pbw) | Acid generator (pbw) | Crosslinker (pbw) | Surfactant (pbw) | Organic solvent (pbw) | Film formation |
|---|---|---|---|---|---|---|---|---|
| Example | 1-1 | Polymer 1 (54) | Dye-A (26) | AG1 (4) | XL1 (0) | FC-4430 (0.1) | Cyclohexanone (1,252) PGMEA (125) | ○ |
|  | 1-2 | Polymer 2 (48) | Dye-B (32) | AG1 (2) | XL1 (2) | FC-4430 (0.1) | Cyclohexanone (1,252) PGMEA (125) | ○ |
|  | 1-3 | Polymer 2 (48) | Dye-C (32) | AG1 (2) | XL1 (2) | FC-4430 (0.1) | Cyclohexanone (1,252) PGMEA (125) | ○ |
|  | 1-4 | Polymer 3 (40) | Dye-D (40) | AG1 (4) | XL1 (8) | FC-4430 (0.1) | Cyclohexanone (1,252) PGMEA (125) | ○ |
|  | 1-5 | Polymer 3 (40) | Dye-E (40) | AG1 (4) | XL1 (8) | FC-4430 (0.1) | Cyclohexanone (1,252) PGMEA (125) | ○ |
|  | 1-6 | Polymer 3 (40) | Dye-F (40) | AG1 (4) | XL1 (8) | FC-4430 (0.1) | Cyclohexanone (1,252) PGMEA (125) | ○ |
|  | 1-7 | Polymer 3 (48) | Dye-D (32) | AG1 (2) | XL1 (2) | FC-4430 (0.1) | Cyclohexanone (1,252) PGMEA (125) | ○ |
|  | 1-8 | Polymer 3 (40) | Dye-G (40) | AG1 (4) | XL1 (8) | FC-4430 (0.1) | Cyclohexanone (1,252) PGMEA (125) | ○ |
|  | 1-9 | Polymer 3 (40) | Dye-H (40) | AG1 (4) | XL1 (8) | FC-4430 (0.1) | Cyclohexanone (1,252) PGMEA (125) | ○ |
|  | 1-10 | Polymer 3 (40) | Dye-I (40) | AG1 (4) | XL1 (8) | FC-4430 (0.1) | Cyclohexanone (1,252) PGMEA (125) | ○ |
|  | 1-11 | Polymer 3 (40) | Dye-R (40) | AG1 (4) | XL1 (8) | FC-4430 (0.1) | Cyclohexanone (1,252) PGMEA (125) | ○ |

TABLE 1-continued

| | | Polymer (pbw) | NIR absorbing dye (pbw) | Acid generator (pbw) | Crosslinker (pbw) | Surfactant (pbw) | Organic solvent (pbw) | Film formation |
|---|---|---|---|---|---|---|---|---|
| Comparative Example | 1-1 | Polymer 1 (54) | Dye-J (26) | AG1 (4) | XL1 (0) | FC-4430 (0.1) | Cyclohexanone (1,252) PGMEA (125) | X |
| | 1-2 | Polymer 2 (54) | Dye-K (26) | AG1 (4) | XL1 (0) | FC-4430 (0.1) | Cyclohexanone (1,252) PGMEA (125) | X |
| | 1-3 | Polymer 2 (48) | Dye-L (32) | AG1 (2) | XL1 (2) | FC-4430 (0.1) | Cyclohexanone (1,252) PGMEA (125) | X |
| | 1-4 | Polymer 3 (40) | Dye-M (40) | AG1 (4) | XL1 (8) | FC-4430 (0.1) | Cyclohexanone (1,252) PGMEA (125) | X |
| | 1-5 | Polymer 3 (54) | Dye-N (26) | AG1 (4) | XL1 (8) | FC-4430 (0.1) | Cyclohexanone (1,252) PGMEA (125) | X |
| | 1-6 | Polymer 3 (40) | Dye-O (40) | AG1 (4) | XL1 (8) | FC-4430 (0.1) | Cyclohexanone (1,252) PGMEA (125) | X |
| | 1-7 | Polymer 3 (40) | Dye-P (40) | AG1 (4) | XL1 (8) | FC-4430 (0.1) | Cyclohexanone (1,252) PGMEA (125) | X |
| | 1-8 | Polymer 3 (40) | Dye-Q (40) | AG1 (4) | XL1 (8) | FC-4430 (0.1) | Cyclohexanone (1,252) PGMEA (125) | X |

Note that the components in Table 1 are as identified below.
Acid generator AG1: triethylammonium nonaflate
Crosslinker XL1: 1,3,4,6-tetramethoxymethyl glycoluril
PGMEA: propylene glycol monomethyl ether acetate As seen from Table 1, the compositions of Comparative Examples showed defective film formation due to low solvent solubility. That is, the presence of insoluble matter in the coating prevented formation of a uniform film. In contrast, uniform films could be formed from the NIR absorptive film-forming compositions of Examples 1-1 to 1-11 since the dyes had satisfactory solvent solubility.

The NIR absorptive films comprising the novel NIR absorbing dyes of the invention are useful in the development of optical filters for use in PDPs, IR-sensitive printing plates and the like. They are also useful in the micropatterning step in the process of fabricating semiconductor and microelectronic devices.

While the invention has been described with reference to a preferred embodiment, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims.

Japanese Patent Application No. 2010-253448 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A near-infrared absorptive film-forming composition comprising:
at least one polymer with a weight average molecular weight (Mw) of 1,000 to 200,000;
at least one solvent;
and from 20 to 100 parts by weight per 100 parts by weight of the overall solids in the film- forming composition of at least one near-infrared absorbing dye represented by the general formula (2):

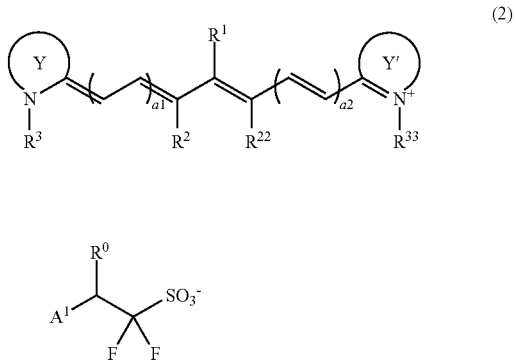

wherein $R^1$ is hydrogen, halogen, cyano or a straight, branched or cyclic $C_1$-$C_{20}$ monovalent hydrocarbon group which may contain a heteroatom, $R^2$ and $R^{22}$ are each independently hydrogen or a straight or branched $C_1$-$C_{10}$ monovalent hydrocarbon group, $R^2$ and $R^{22}$ may bond together to form a ring with the carbon atoms to which they are attached and the intervening carbon atom, $R^3$ and $R^{33}$ are each independently a straight, branched or cyclic $C_1$-$C_{20}$ monovalent hydrocarbon group which may contain a heteroatom, a1 and a2 are each independently an integer of 0 to 5, $A^1$ is hydrogen or trifluoromethyl, $R^0$ is hydroxyl or —OC(=O)—R' wherein R' is a straight, branched, or cyclic $C_1$-$C_{50}$ monovalent hydrocarbon group which may contain a heteroatom, and the partial structures in formula (2):

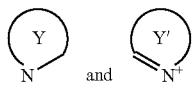

are each independently an aliphatic or aromatic nitrogen-containing heterocyclic compound of 4 to 15 carbon atoms which may contain a heteroatom, and wherein when the film-forming composition is coated, the resulting film containing the dye capable of absorbing radiation in a wavelength 800 to 1,200 nm.

2. The composition of claim 1, further comprising at least one component selected from among an acid generator, a crosslinker, and a surfactant.

3. A near-infrared absorptive film which is formed by coating the composition of claim 1 and evaporating off the solvent.

4. The composition of claim 1, wherein said polymer is a polyvinyl compound, a fluorinated resin, a polyamide, a polyimide, a polyurethane, a polypeptide, a polyester, a polycarbonate, a polyether, an epoxy resin, a polyvinyl alcohol, or a polyvinyl butyral.

5. The composition of claim 1, wherein said solvent is a ketone, an alcohol, an ether, an ester, or a lactone.

6. The composition of claim 1, wherein said near-infrared absorbing dye is represented by the general formula (4):

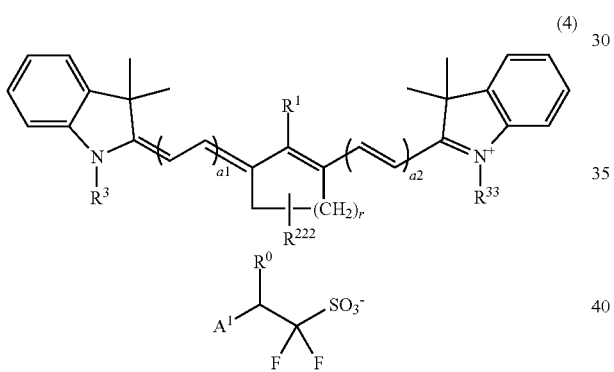

(4)

wherein $R^1$, $R^3$, $R^{33}$, a1, a2, $A^1$, $R^0$ are as defined above, $R^{222}$ is hydrogen or a straight, branched or cyclic $C_1$-$C_5$ monovalent hydrocarbon group, and r is 1 or 2.

7. The composition of claim 1, wherein said near-infrared absorbing dye is represented by the general formula (5):

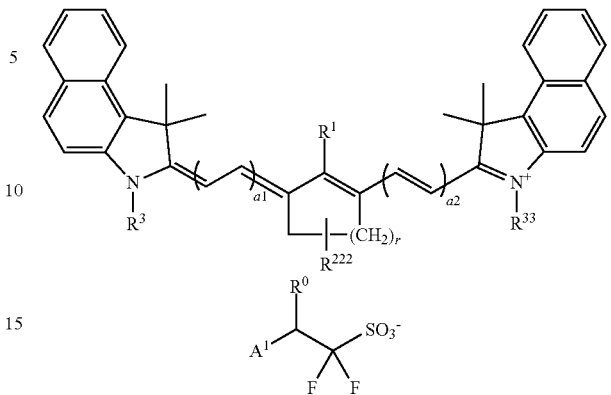

(5)

wherein $R^1$, $R^3$, $R^{33}$, a1, a2, $A^1$, $R^0$ are as defined above, $R^{222}$ is hydrogen or a straight, branched or cyclic $C_1$-$C_5$ monovalent hydrocarbon group, and r is 1 or 2.

8. The composition of claim 1, wherein said near-infrared absorbing dye is represented by the general formula (6):

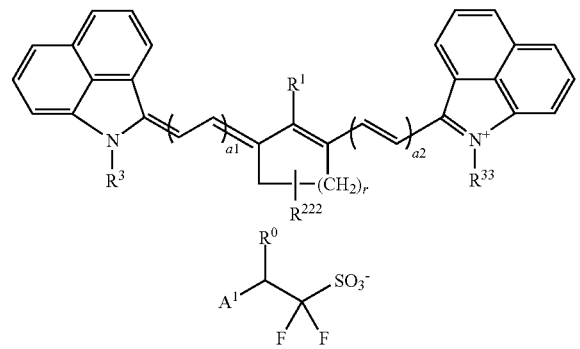

(6)

wherein $R^1$, $R^3$, $R^{33}$, a1, a2, $A^1$, $R^0$ are as defined above, $R^{222}$ is hydrogen or a straight, branched or cyclic $C_1$-$C_5$ monovalent hydrocarbon group, and r is 1 or 2.

* * * * *